(12) United States Patent
Leung et al.

(10) Patent No.: US 11,638,339 B2
(45) Date of Patent: Apr. 25, 2023

(54) LIGHT FIXTURES AND METHODS

(71) Applicant: IDEAL INDUSTRIES LIGHTING LLC, Racine, WI (US)

(72) Inventors: Michael Leung, Ventura, CA (US); Ben Jacobson, Chicago, IL (US); Eric Tarsa, Goleta, CA (US); James Ibbetson, Santa Barbara, CA (US); Claudio Girotto, Santa Barbara, CA (US); Bernd Keller, Santa Barbara, CA (US)

(73) Assignee: IDEAL INDUSTRIES LIGHTING LLC, Racine, WI (US)

( * ) Notice: Subject to any disclaimer, the term of this patent is extended or adjusted under 35 U.S.C. 154(b) by 0 days.

(21) Appl. No.: 17/120,802

(22) Filed: Dec. 14, 2020

(65) Prior Publication Data

US 2021/0095825 A1 Apr. 1, 2021

Related U.S. Application Data

(63) Continuation of application No. 16/667,239, filed on Oct. 29, 2019, now Pat. No. 10,900,621, which is a
(Continued)

(51) Int. Cl.
*H05B 45/20* (2020.01)
*F21V 33/00* (2006.01)
(Continued)

(52) U.S. Cl.
CPC ............. *H05B 45/20* (2020.01); *F21K 9/61* (2016.08); *F21S 8/006* (2013.01); *F21S 8/026* (2013.01);
(Continued)

(58) Field of Classification Search
CPC . H05B 45/10; H05B 45/20; F21K 9/61; F21S 8/006; F21S 8/026; F21S 19/005;
(Continued)

(56) References Cited

U.S. PATENT DOCUMENTS 6,142,645 A 11/2000 Han
6,528,782 B1 3/2003 Zhang
(Continued)

FOREIGN PATENT DOCUMENTS

CN 204114757 U 1/2015
EP 2 381 047 10/2011
(Continued)

OTHER PUBLICATIONS

Japanese Office Action (Application No. 2019-562214) dated Sep. 30, 2021 (with Global Dossier Translation and translation provided by Japanese law firm).
(Continued)

*Primary Examiner* — Alan B Cariaso
(74) *Attorney, Agent, or Firm* — J. Clinton Wimbish; Nexsen Pruet, PLLC

(57) ABSTRACT

A light fixture, e.g., as an artificial skylight, in which light within a region defined by x, y color coordinates (0.37, 0.34), (0.35, 0.38), (0.15, 0.20), and (0.20, 0.14) exits a first light engine, and light within a region defined by coordinates (0.29, 0.32), (0.32, 0.29), (0.41, 0.36), (0.48, 0.39), (0.48, 0.43), (0.40, 0.41), and (0.35, 0.38) exits a second light engine. Also, light fixtures in which a second light engine comprises a sidewall, and light exiting a first light engine passes through space defined by the sidewall; light fixtures in which first and second light engines are able to output light providing different CS values at a luminance; light fixtures in which light incident on a surface of the fixture and cumulative light exiting the fixture have different color
(Continued)

points; light fixtures in which light distribution characteristics of light engines differ; and/or other features. The invention also relates to corresponding methods.

19 Claims, 24 Drawing Sheets
(2 of 24 Drawing Sheet(s) Filed in Color)

Related U.S. Application Data continuation of application No. 15/419,538, filed on Jan. 30, 2017, now Pat. No. 10,502,374.

(51) Int. Cl.

| | | |
|---|---|---|
| F21S 19/00 | (2006.01) | |
| F21K 9/61 | (2016.01) | |
| F21S 8/00 | (2006.01) | |
| F21S 8/02 | (2006.01) | |
| F21V 7/04 | (2006.01) | |
| F21V 14/02 | (2006.01) | |
| A61N 5/06 | (2006.01) | |
| F21Y 113/17 | (2016.01) | |
| F21Y 115/10 | (2016.01) | |
| F21V 8/00 | (2006.01) | |

(52) U.S. Cl.
CPC .............. *F21S 19/005* (2013.01); *F21V 7/04* (2013.01); *F21V 14/02* (2013.01); *F21V 33/006* (2013.01); *A61N 2005/0663* (2013.01); *F21Y 2113/17* (2016.08); *F21Y 2115/10* (2016.08); *G02B 6/0051* (2013.01)

(58) Field of Classification Search
CPC .......... F21V 7/04; F21V 14/02; F21V 33/006; F21Y 2113/10; F21Y 2113/13; F21Y 2113/17
See application file for complete search history.

(56) References Cited

U.S. PATENT DOCUMENTS

| | | | |
|---|---|---|---|
| 9,030,103 B2 | 5/2015 | Pickard | |
| 9,039,746 B2 | 5/2015 | Van de Ven et al. | |
| 9,125,274 B1 | 9/2015 | Brunault | |
| 9,392,660 B2* | 7/2016 | Dias ........................ | H05B 45/22 |
| 9,425,172 B2 | 8/2016 | Van de Ven et al. | |
| 9,484,329 B2 | 11/2016 | Van de Ven et al. | |
| 9,488,327 B2 | 11/2016 | Van Gheluwe et al. | |
| 9,795,000 B1* | 10/2017 | Sooch .................... | H05B 47/16 |
| 9,915,775 B2 | 3/2018 | Krames | |
| 9,955,551 B2 | 4/2018 | Spero | |
| 9,974,138 B2 | 5/2018 | Allen | |
| 10,022,556 B1* | 7/2018 | Holbert ................ | A61N 5/0618 |
| 10,077,884 B2 | 9/2018 | Di Trapani et al. | |
| 2007/0139920 A1 | 6/2007 | Van de Ven | |
| 2008/0103561 A1 | 5/2008 | Moscovici | |
| 2008/0297027 A1* | 12/2008 | Miller .................... | H05B 45/20 313/498 |
| 2010/0103660 A1 | 4/2010 | Van de Ven et al. | |
| 2010/0127283 A1 | 5/2010 | Van de Ven et al. | |
| 2011/0084614 A1* | 4/2011 | Eisele .................. | H05B 47/105 315/297 |
| 2014/0185281 A1 | 7/2014 | Lee | |
| 2014/0301062 A1 | 10/2014 | David | |
| 2015/0062892 A1 | 3/2015 | Krames | |
| 2015/0195885 A1 | 7/2015 | Van de Ven et al. | |
| 2015/0327342 A1 | 11/2015 | Lu | |
| 2016/0227618 A1 | 8/2016 | Meerbeek | |
| 2016/0234911 A1 | 8/2016 | Schlangen | |
| 2016/0273723 A1 | 9/2016 | Van Gheluwe et al. | |
| 2016/0286616 A1 | 9/2016 | Van de Ven | |
| 2016/0320023 A1 | 11/2016 | Meerbeek et al. | |
| 2016/0363710 A1 | 12/2016 | Van Boven et al. | |
| 2018/0073712 A1 | 3/2018 | Baaijens | |
| 2018/0160491 A1 | 6/2018 | Biery | |

FOREIGN PATENT DOCUMENTS

| | | | |
|---|---|---|---|
| JP | 2011-138731 A1 | 7/2011 | |
| JP | 2016-514340 A1 | 5/2016 | |
| JP | 2016-536744 A1 | 11/2016 | |
| JP | 2016-540349 A1 | 12/2016 | |
| TW | 201029146 A | 8/2010 | |
| WO | WO-2008146219 A1 * | 12/2008 | ........... A61N 5/0618 |
| WO | 2009/010822 | 1/2009 | |
| WO | 2012/051095 | 4/2012 | |
| WO | 2014/076656 A | 5/2014 | |
| WO | 2015/055430 | 4/2015 | |
| WO | 2015/055430 A1 | 4/2015 | |
| WO | 2015/128201 | 9/2015 | |

OTHER PUBLICATIONS

U.S. Appl. No. 15/419,538; 2018/0216791 A1, filed Jan. 30, 2017; Aug. 2, 2018, Michael Leung et al.
U.S. Appl. No. 16/667,239, filed Oct. 29, 2019; Feb. 27, 2020, Michael Leung et al.
MS Rea PhD et al., *Modelling the spectral sensitivity of the human circadian system*, Lighting Res. Technol. 2012; 44: 386-396, 11 pages.
MS Rea PhD et al., *Circadian light*, Journal of Circadian Rhythms 2010, 8:2, pp. 1-10.
Robert J. Lucas et al., *Measuring and using light in the melanopsin age*, Trends Neurosci., Jan. 2014; 37(1): 1-9; Published online Nov. 25, 2013 doi: 10.1016/j.tins.2013.10.004, 13 pages.
Peter Mansbach, *Lux—Circadian Sleep Disorders Network—Advocating for people with misaligned body clocks*, downloaded on Oct. 19, 2016, 4 pages.
*Circadian Rhythm Lighting*, Circadian Lighting, Lighting's Impact on Circadian Rhythm/USAI, Mar. 2015, 6 pages.
*CoeLux: The $40,000 Artificial Skylight Everyone Will Want*, http://www.cepro.com/article/coelux_the_40000_fake_skylight_everyone_will_want, downloaded in 2016, 9 pages.
*CoeLux® Products*, http://www.coelux.com/en/products/index:, CoeLux® 45 LC, CoeLux® 45 Square, CoeLux® 45 HC, CoeLux® 60, downloaded in 2016, 4 pages.
Invitation to Pay Additional Fees and, Where Applicable, ProtestFee from a corresponding international patent application (PCT/US2018/015509) dated May 16, 2018, 20 pages.
International Search Report and Written Opinion of the International Searching Authority from a corresponding international patent application (PCT/US2018/015509) dated Jul. 11, 2018, 22 pages.
Taiwan Office Action (and translation provided by foreign counsel) from a corresponding Taiwan patent application (Taiwan Patent Application No. 107103272) dated May 17, 2019, 20 pages.
International Preliminary Report on Patentability from a corresponding international patent application (PCT/US2018/015 509) dated Aug. 8, 2019.
Taiwanese Office Action (with English translation) dated Mar. 17, 2020.
Korean Office Action (Application No. 10-2019-7024819) dated May 21, 2021 (with English translation).
English Translation of Korean Office Action dated May 21, 2021 provided by the Applicant.

* cited by examiner

LIGHT FIXTURES AND METHODS

CROSS-REFERENCE TO RELATED APPLICATIONS

This application is a continuation of U.S. patent application Ser. No. 16/667,239, filed Oct. 29, 2019 (now U.S. Pat. No. 10,502,374)(the entirety of which is incorporated herein by reference), which is a continuation of U.S. patent application Ser. No. 15/419,538, filed Jan. 30, 2017 (the entirety of which is also incorporated herein by reference).

FIELD OF THE INVENTIVE SUBJECT MATTER

The present inventive subject matter relates to light fixtures and methods of lighting. In some aspects, the present inventive subject matter relates to light fixtures (comprising one or more light sources and/or one or more light engines) that mimic the appearance and/or effects of a skylight, and/or that give an "outdoor" feeling to an indoor space, in some cases even with no exterior light from any windows or doors.

BACKGROUND

Skylights are used to provide natural light (i.e., daylight) in residential, commercial and other buildings, as well as in other structures.

Conventional skylights can pose numerous problems, including water leakage, heat loss, lack of light on overcast or stormy days, difficulty installing, or impossibility/impracticality of installing (e.g., in the first story of a multi-story structure. In addition, conventional skylights—like windows—typically get dirty, streaked and/or smeared, and as a result there is often a frequent desire (or need) to clean them. In addition, direct sunlight can sometimes produce a great deal of glare on work surfaces and other items, e.g., computer screens, and such glare is typically counterproductive and/or annoying (for example, glare can make it difficult or impossible for a worker to see his or her computer screen). Also, direct sunlight (and/or resulting glare) can increase eye strain (even after a short period of time, and more so during prolonged exposure, including continuous exposure as well as intermittent exposure over periods of time).

It would be beneficial to provide a skylight that overcomes such problems and that provides the benefits of conventional skylights, and/or that can enable there to be control over the light being provided.

BRIEF SUMMARY

In a first aspect, the present inventive subject matter relates to light fixtures (artificial skylights) that avoid problems with conventional skylights and that provide benefits that are provided by conventional skylights.

Conventional skylights provide a number of benefits including:
Light that is full spectrum (high quality or color rendering);
Light that is visually complex due to the combination of diffuse light from the sky and directional light from the sun, which generally have different colors;
Light that naturally varies with time (i.e., circadian, seasonal) and weather;
Thus, generally providing a visual connection with the outdoors that is pleasing, and that can improve mood and health.

In accordance with the first aspect of the present inventive subject matter, at least a portion of a first light engine resembles a sky (e.g., a surface of the first light engine looks like the sky to a viewer), and light exiting from a second light engine has one or more characteristics that resemble that (or those) of at least a portion of light emitted by (and received from) the sun.

In some light fixtures in accordance with the first aspect of the present inventive subject matter, many advantages are provided, including the ability to supply light (in residential buildings, commercial buildings, other buildings and other structures) while avoiding or reducing (in comparison to other devices, such as conventional skylights) water leakage, providing lower heat loss, providing light on overcast or stormy days, simplifying installation, providing the ability for installation (e.g., in locations where installation of a skylight would be problematic or impossible, e.g., in the first story of a multi-story structure, or in a building in which the roof is spaced a large distance from a ceiling), providing the ability to control light exiting from the device into an office, a room or any other space (e.g., controlling the brightness and/or the color of light exiting from the light fixture). In addition, light fixtures in accordance with the first aspect of the present inventive subject matter can simplify cleaning (e.g., devices can be more easily accessed, and/or can be removed from a structure on which they are mounted).

In a second aspect, the present inventive subject matter relates to light fixtures that comprise first and second light engines, in which the second light engine comprises a sidewall from which light exits.

In a third aspect, the present inventive subject matter relates to light fixtures that output light having specific characteristics. For example, some embodiments provide for light emission that can achieve specific biological effects, such as adjusting a person's biological melatonin levels in a desired way (e.g., during twenty-four-hour periods), for instance to adjust a person's circadian rhythm, to ameliorate a person's circadian rhythm disorders, and/or to adjust a person's alertness (e.g., to increase the person's alertness during some daily time periods and/or to increase the person's drowsiness during other daily time periods).

The present inventive subject matter further includes methods that comprise supplying electricity to any light fixture as described herein. In some of such embodiments, color and brightness of light exiting the light fixture are controlled independently to provide the illusion of natural daylight passing through a conventional skylight.

The present inventive subject matter further includes methods that comprise moving at least one light engine relative to another light engine in any light fixture as described herein.

The inventive subject matter may be more fully understood with reference to the accompanying drawings and the following detailed description of the inventive subject matter.

BRIEF DESCRIPTION OF THE DRAWING FIGURES

The patent or application file contains at least one drawing executed in color. Copies of this patent or patent application publication with color drawing(s) will be provided by the Office upon request and payment of the necessary fee.

Figure 4:
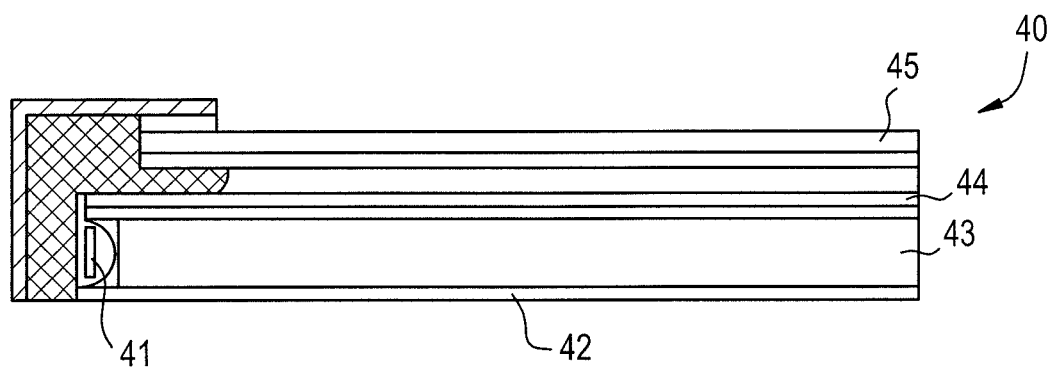

FIG. 4 schematically depicts a representative example of an edge-lit panel that can be used as a component in a light fixture in accordance with the present inventive subject matter.

Figure 5:
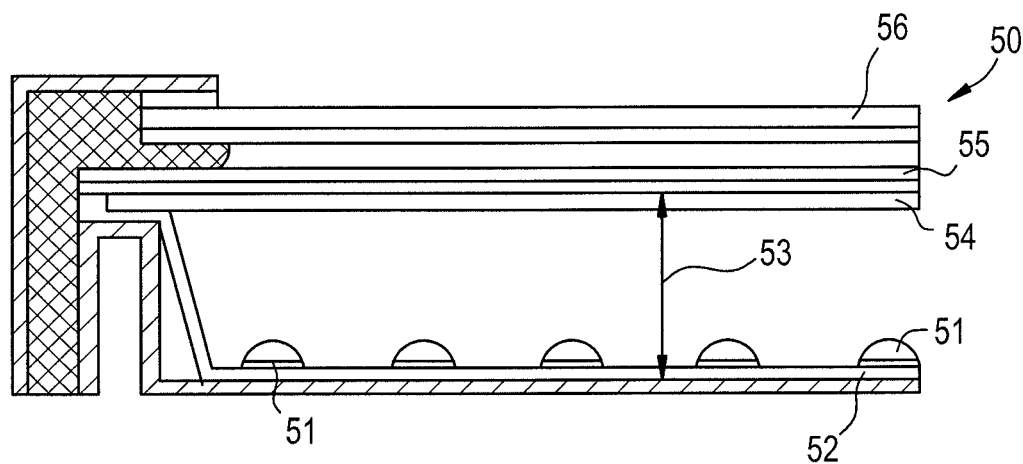

FIG. 5 schematically depicts a representative example of a back-lit panel that can be used as a component in a light fixture in accordance with the present inventive subject matter.

Figure 6:
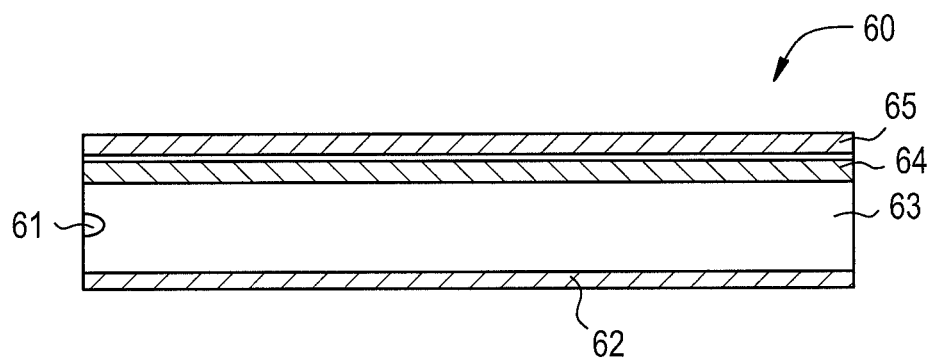

FIG. 6 schematically depicts a representative example of a side-lit panel that can be used as a component in a light fixture in accordance with the present inventive subject matter.

Figure 7:
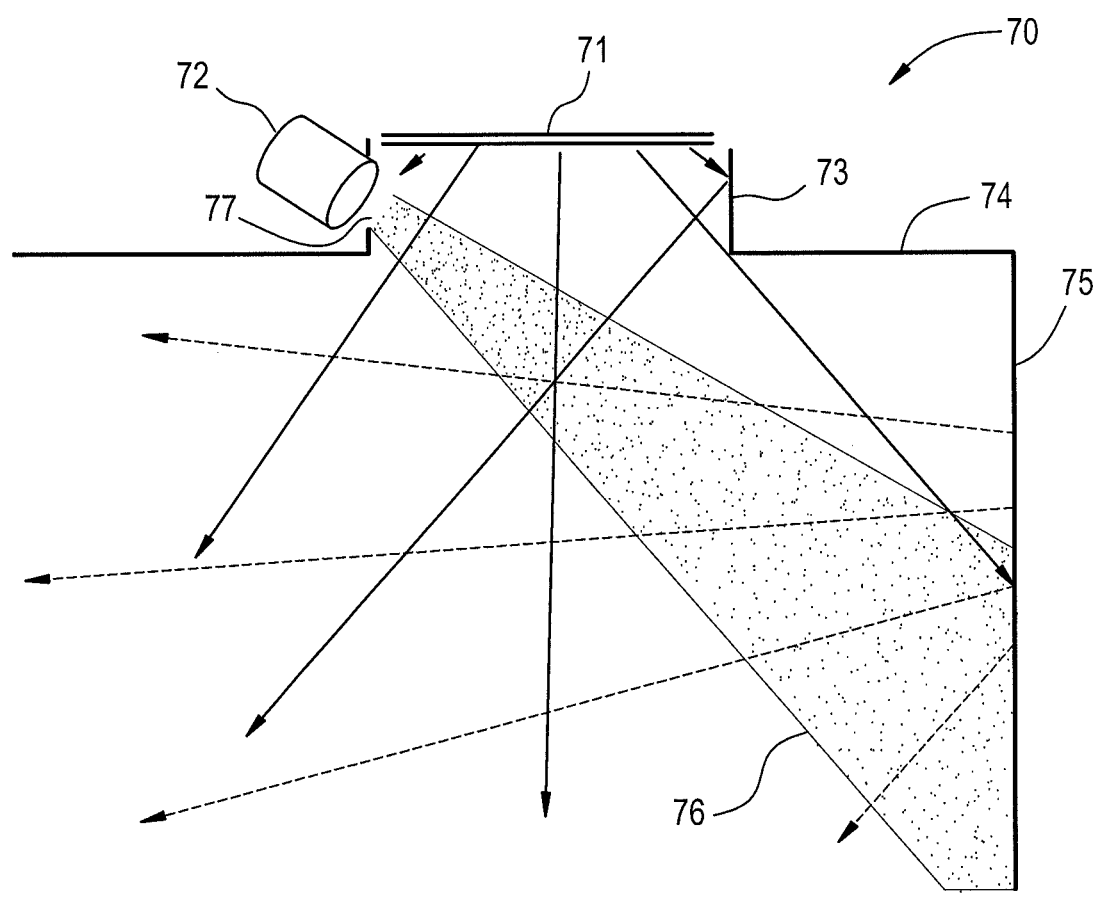

FIG. 7 is a schematic cross-sectional view of an embodiment of a light fixture in accordance with the present inventive subject matter, mounted in a ceiling.

Figure 8:
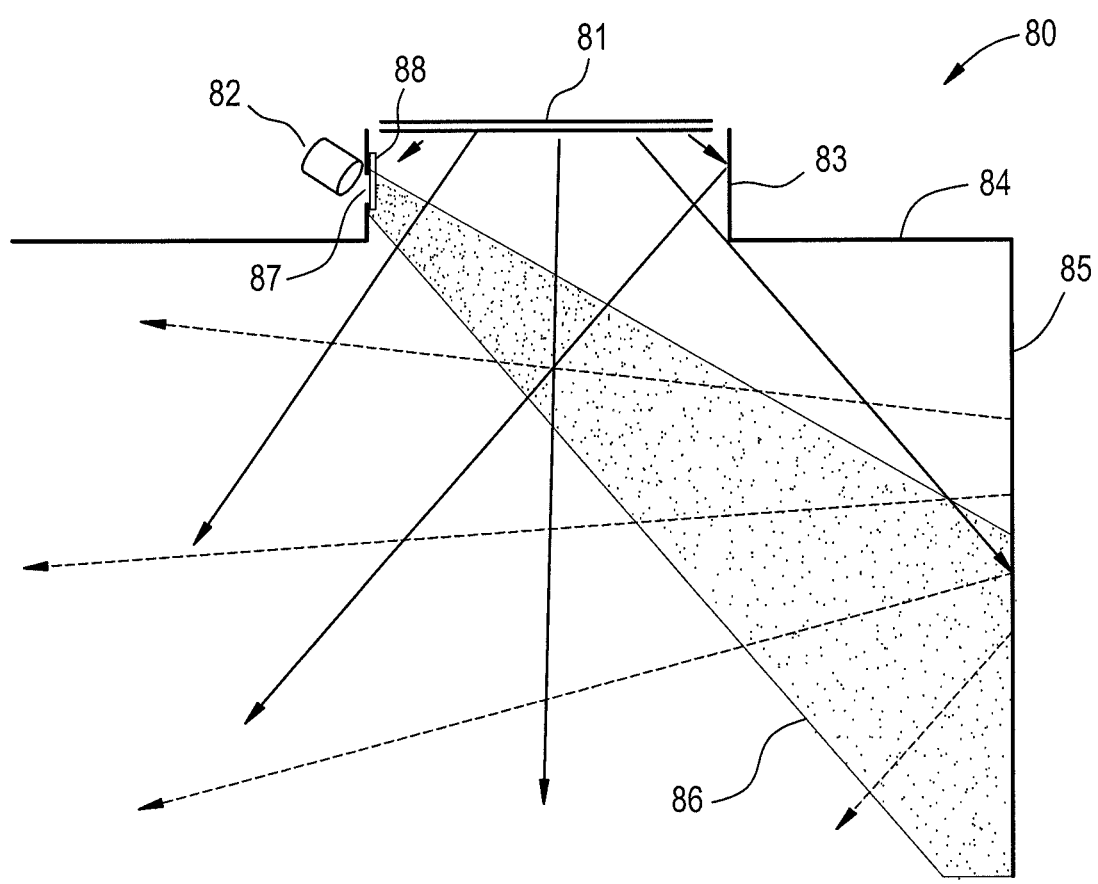

FIG. 8 is a schematic cross-sectional view of an embodiment of a light fixture in accordance with the present inventive subject matter, mounted in a ceiling.

Figure 9A:
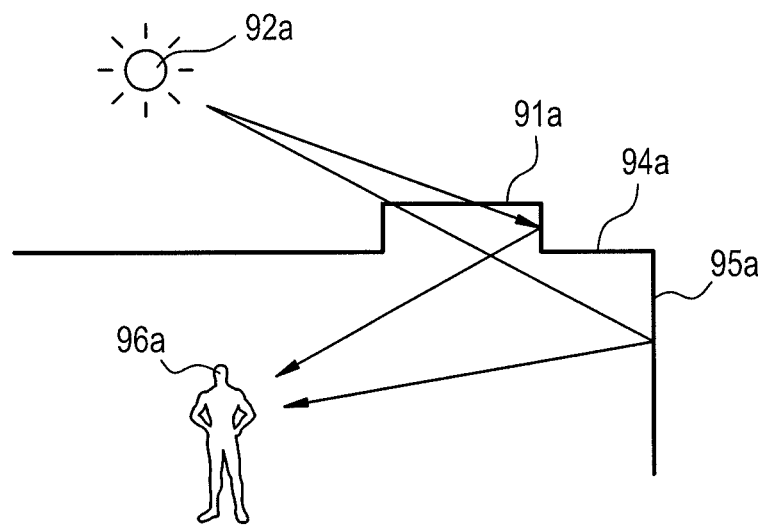
Figure 9B:
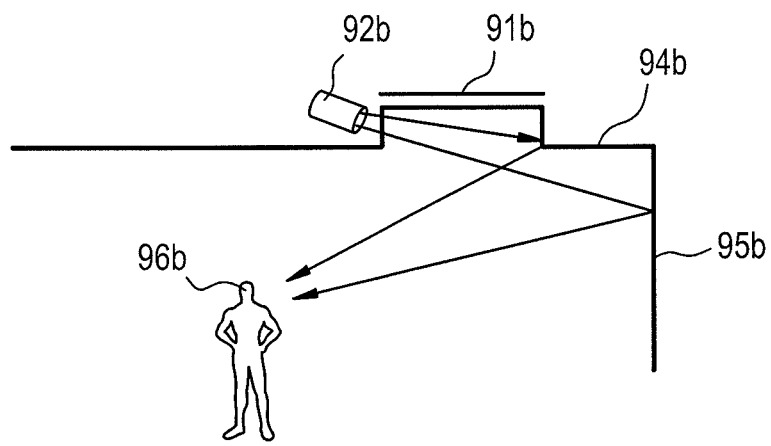
Figure 9C:
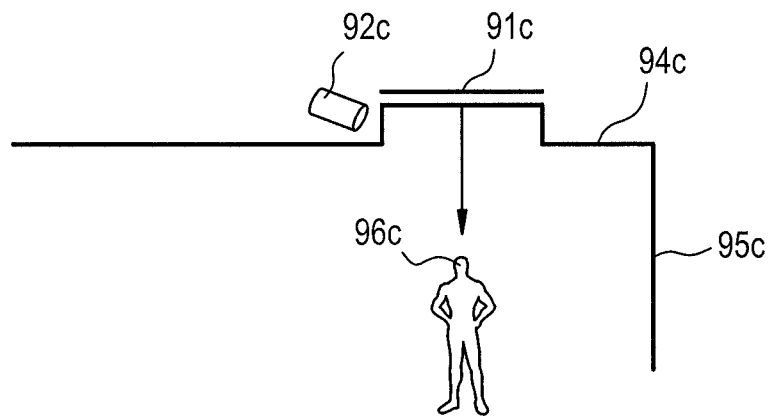

FIG. 9A schematically depicts the visual impression created by a conventional skylight, and FIGS. 9B and 9C depict the visual impression created by representative embodiments of light fixtures in accordance with the present inventive subject matter.

Figure 10:
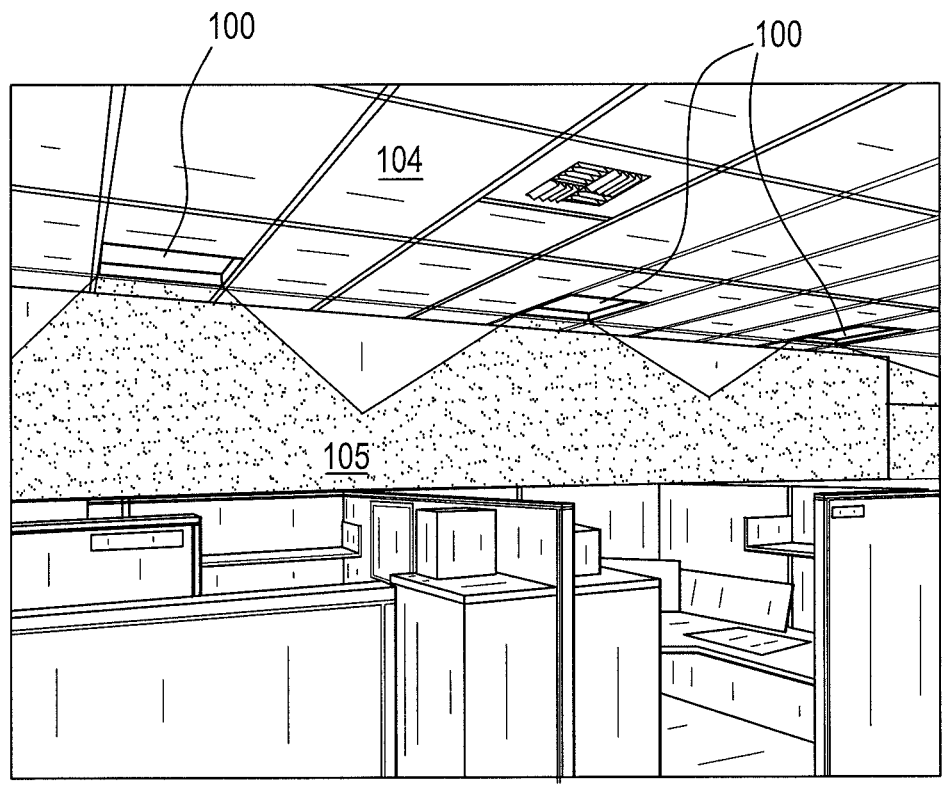

FIG. 10 depicts a room in which three light fixtures (each similar to the light fixture depicted in FIG. 7) are mounted in a ceiling.

Figure 11:
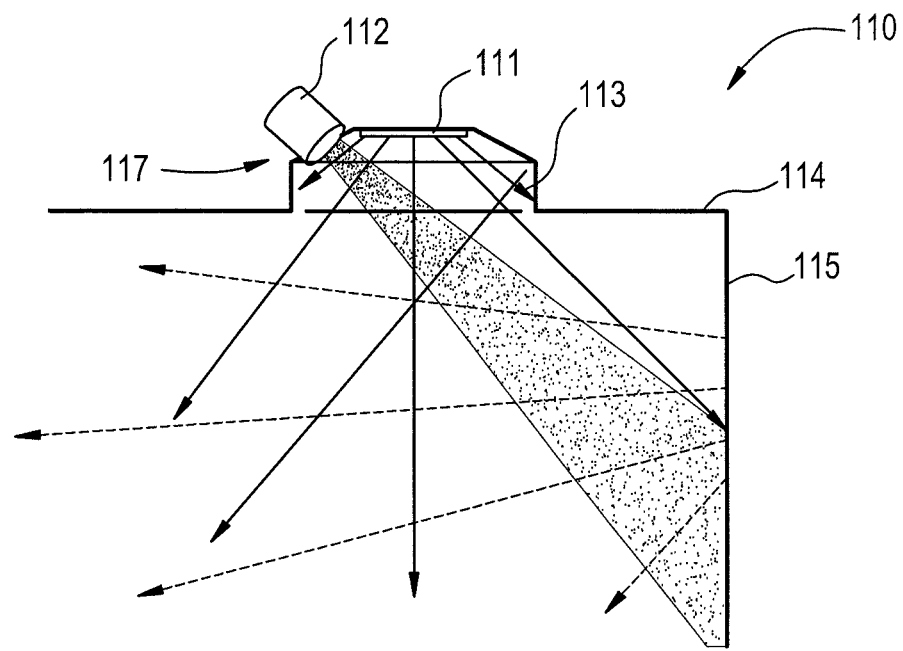

FIG. 11 is a schematic cross-sectional view of an embodiment of a light fixture in accordance with the present inventive subject matter, mounted in a ceiling.

Figure 12:
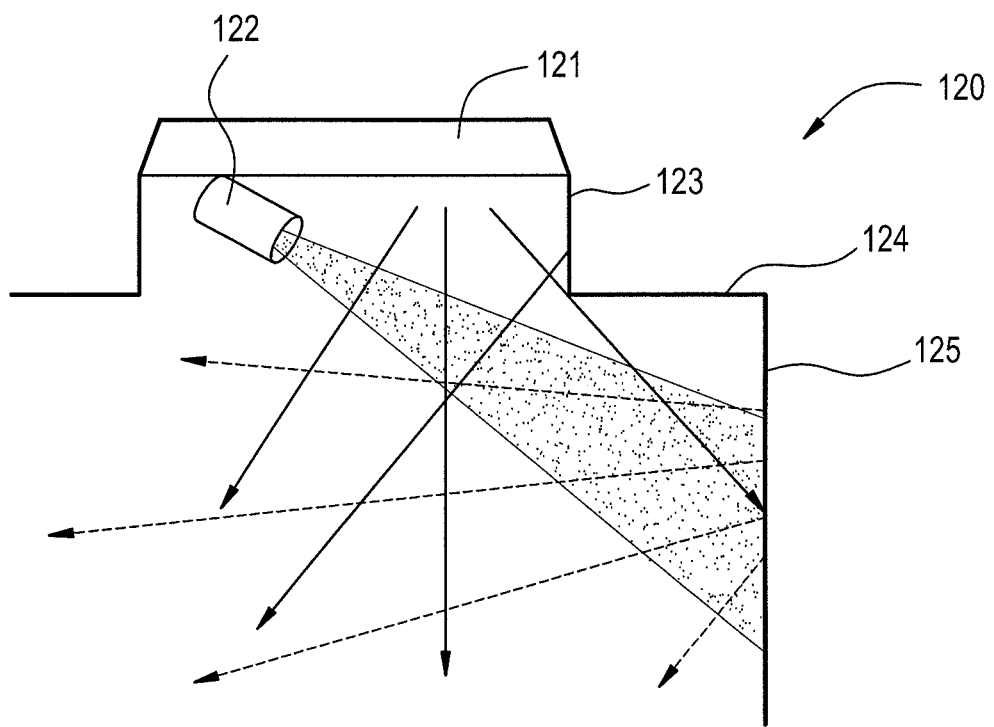

FIG. 12 is a schematic cross-sectional view of an embodiment of a light fixture in accordance with the present inventive subject matter, mounted in a ceiling.

Figure 13:
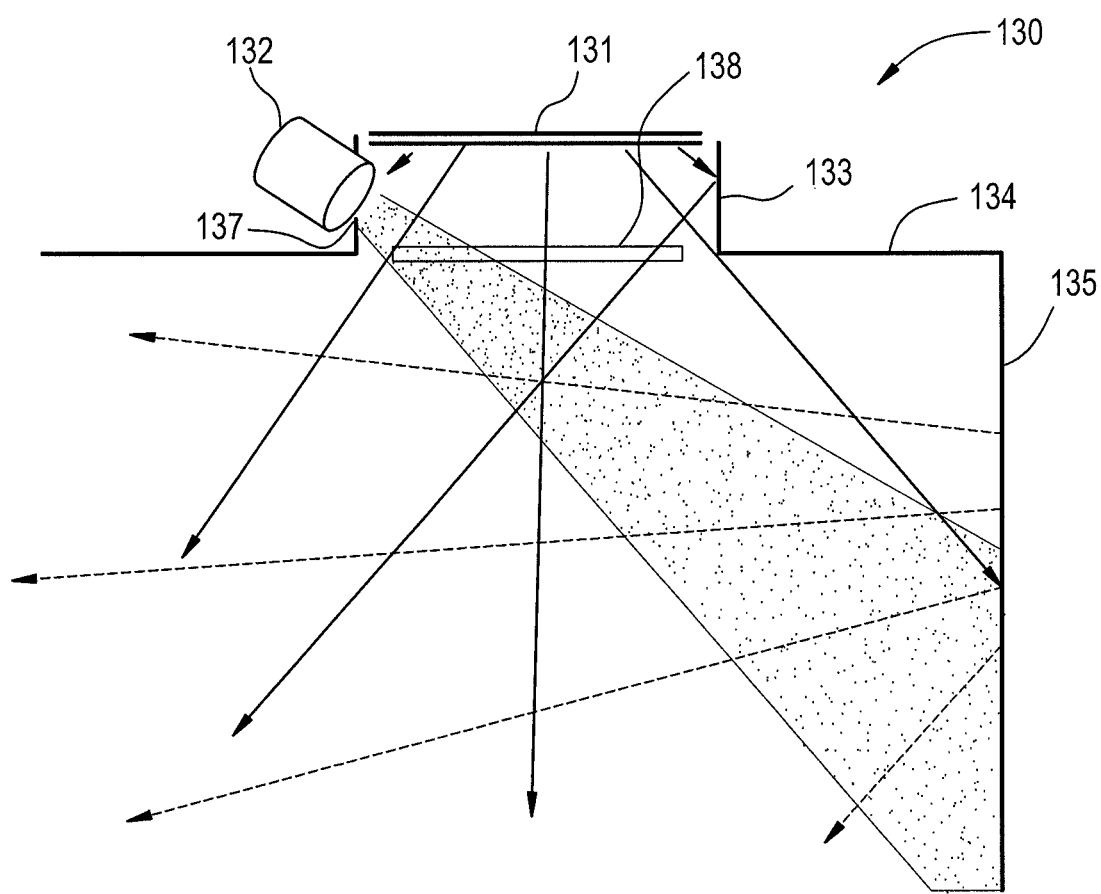

FIG. 13 is a schematic cross-sectional view of an embodiment of a light fixture in accordance with the present inventive subject matter, mounted in a ceiling.

Figure 14:
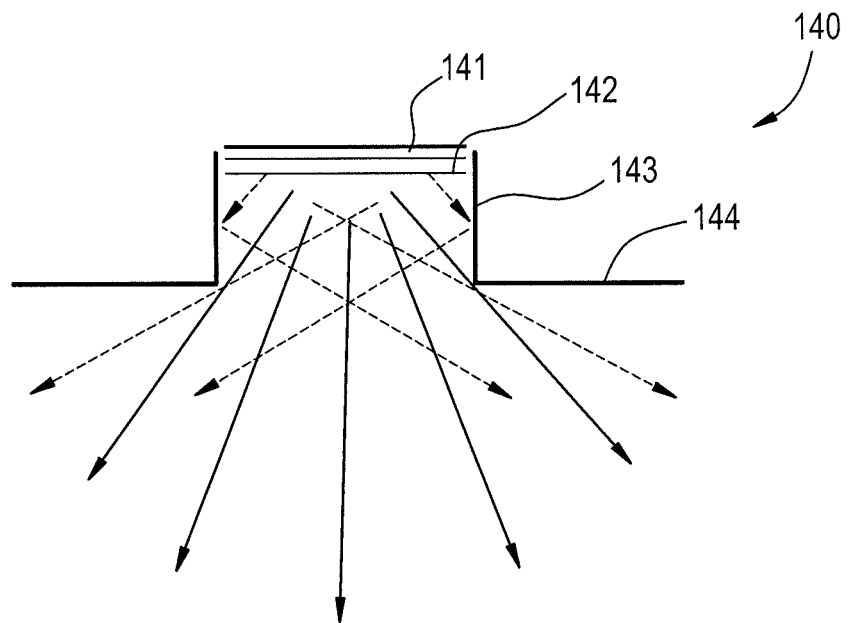

FIG. 14 is a schematic cross-sectional view of an embodiment of a light fixture in accordance with the present inventive subject matter, mounted in a ceiling.

Figure 15:
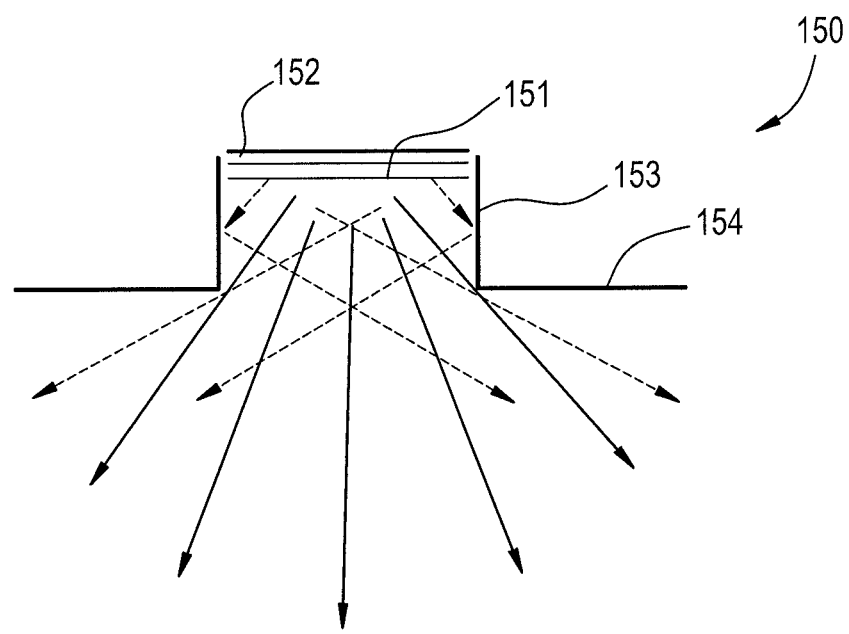

FIG. 15 is a schematic cross-sectional view of an embodiment of a light fixture in accordance with the present inventive subject matter, mounted in a ceiling.

Figure 16:
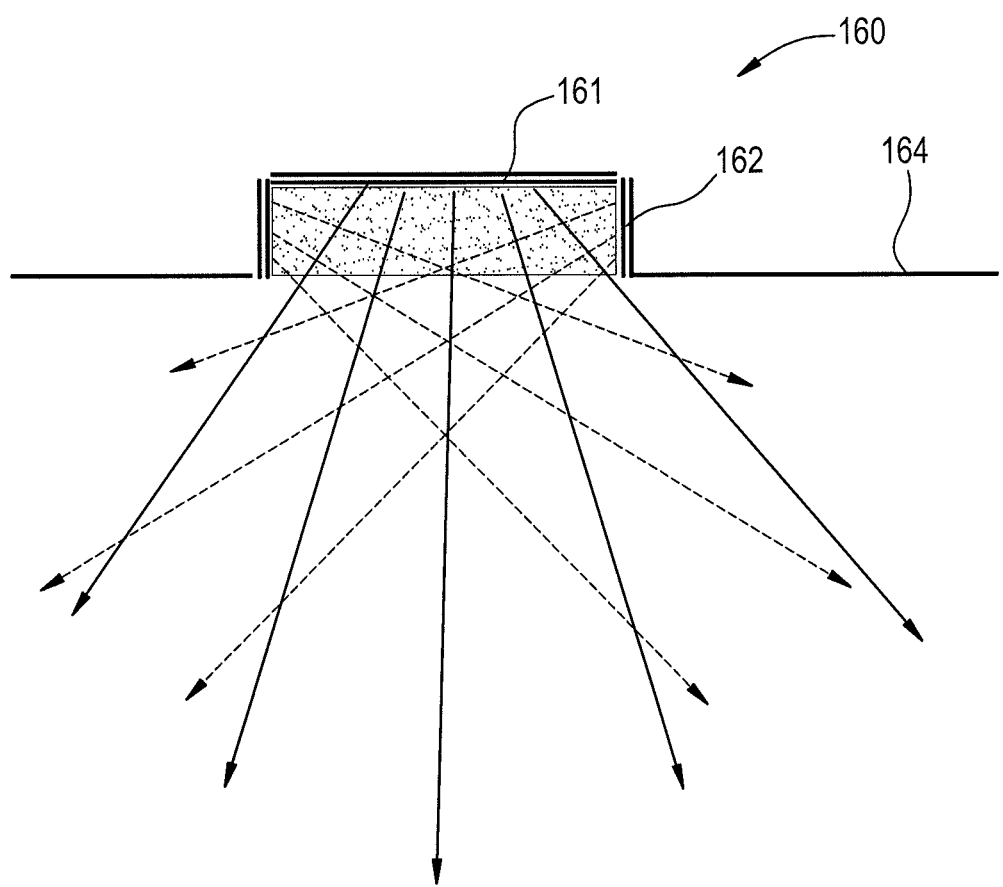

FIG. 16 is a schematic cross-sectional view of an embodiment of a light fixture in accordance with the present inventive subject matter, mounted in a ceiling.

Figure 17:
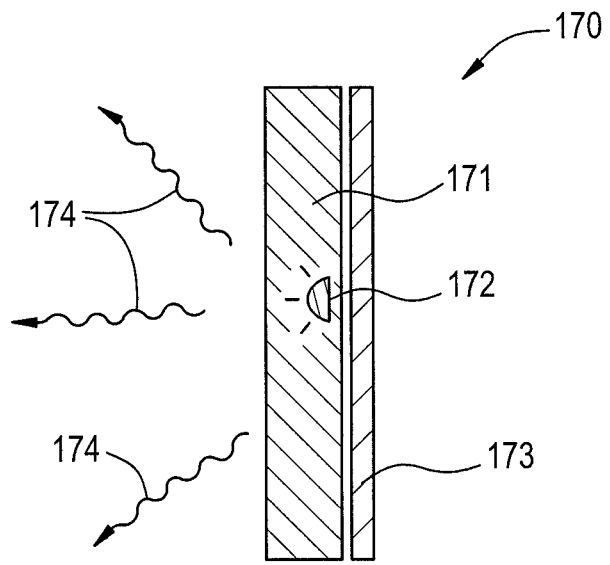

FIG. 17 schematically depicts a cross-sectional view of a portion of a sidewall that can be used as a component in a light fixture in accordance with the present inventive subject matter.

Figure 18:
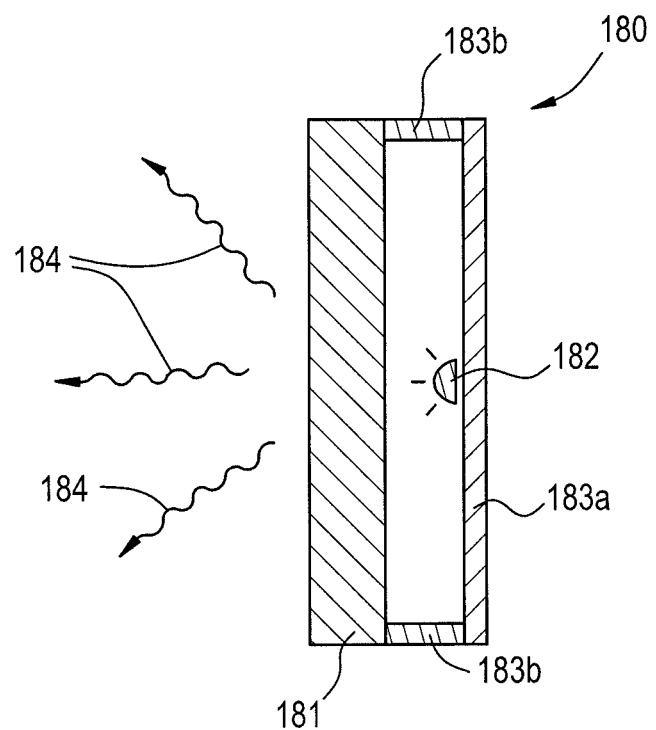

FIG. 18 schematically depicts a cross-sectional view of a portion of a sidewall that can be used as a component in a light fixture in accordance with the present inventive subject matter.

Figure 19:
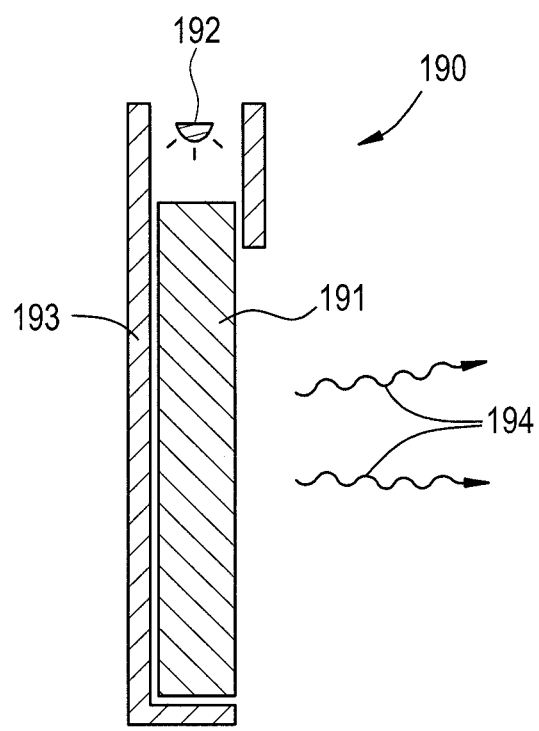

FIG. 19 schematically depicts a cross-sectional view of a portion of a sidewall that can be used as a component in a light fixture in accordance with the present inventive subject matter.

Figure 20:
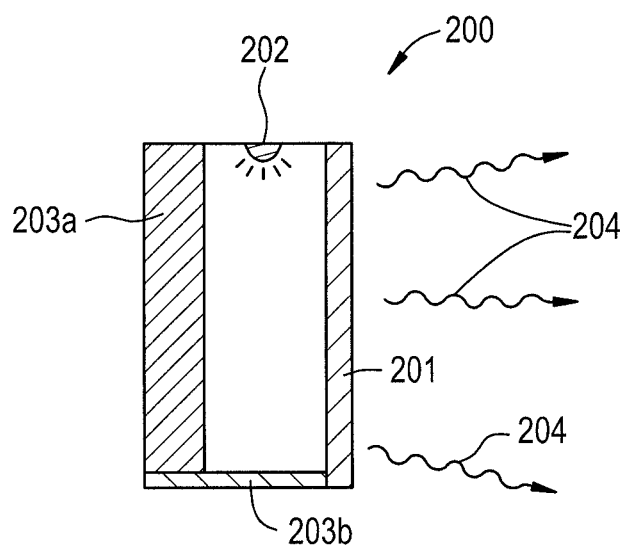

FIG. 20 schematically depicts a cross-sectional view of a portion of a sidewall that can be used as a component in a light fixture in accordance with the present inventive subject matter.

Figure 21:
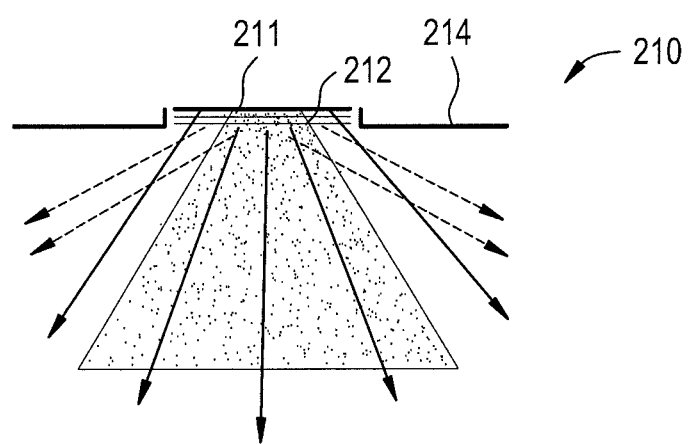

FIG. 21 is a schematic cross-sectional view of an embodiment of a light fixture in accordance with the present inventive subject matter, mounted in a ceiling.

Figure 22:
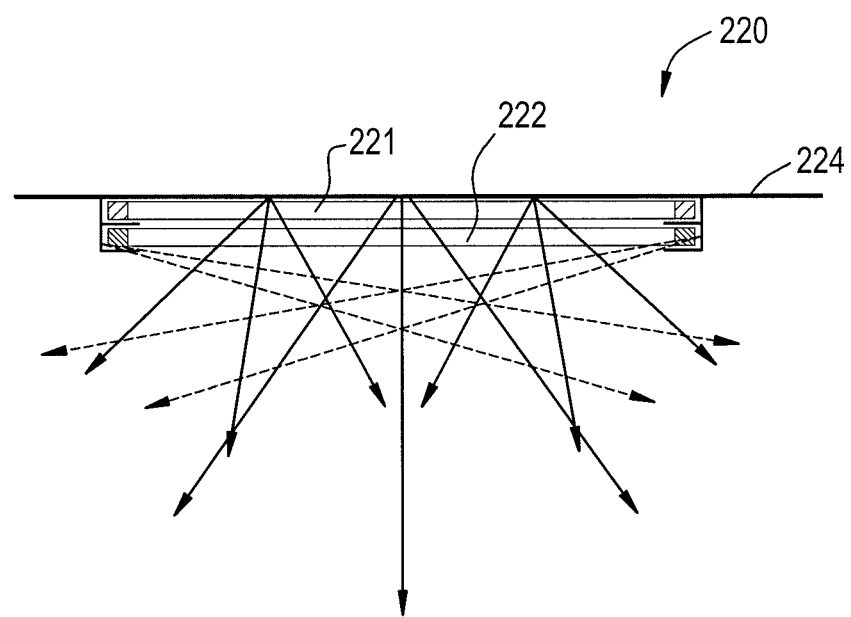

FIG. 22 is a schematic cross-sectional view of an embodiment of a light fixture in accordance with the present inventive subject matter, mounted on a ceiling.

Figure 23:
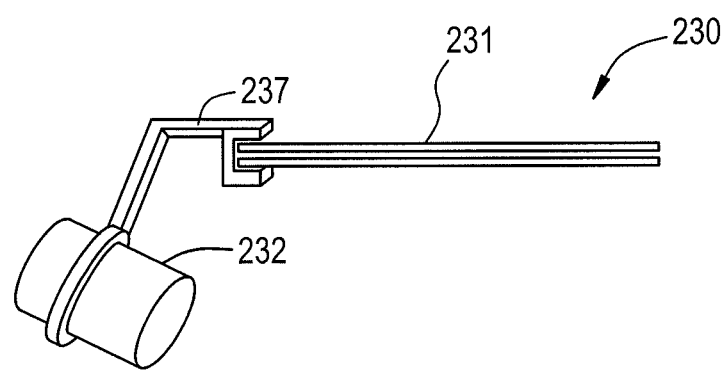

FIG. 23 is a schematic cross-sectional view of an embodiment of a light fixture in accordance with the present inventive subject matter.

Figure 24A:
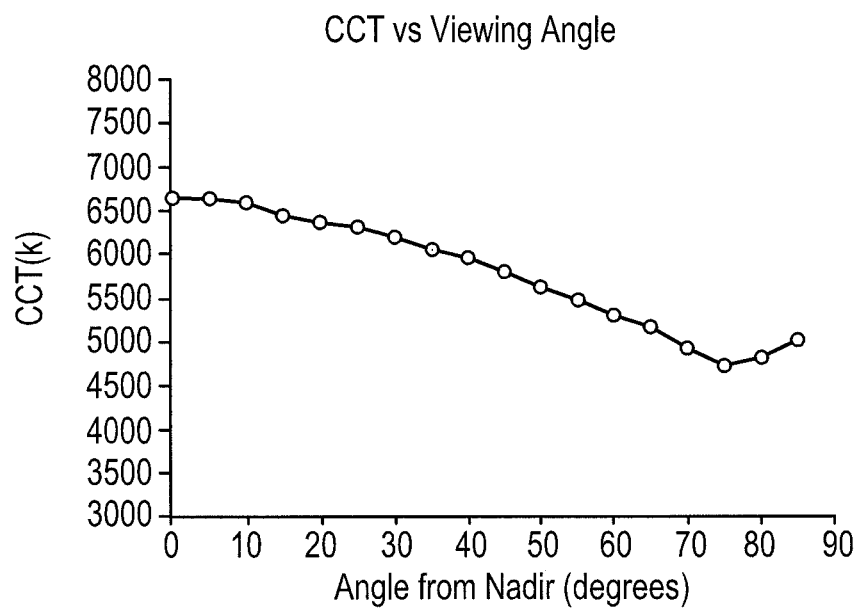

FIG. 24A shows a plot of CCT over viewing angle measured using a light fixture similar to the embodiment of a light fixture depicted in FIG. 16.

Figure 24B:
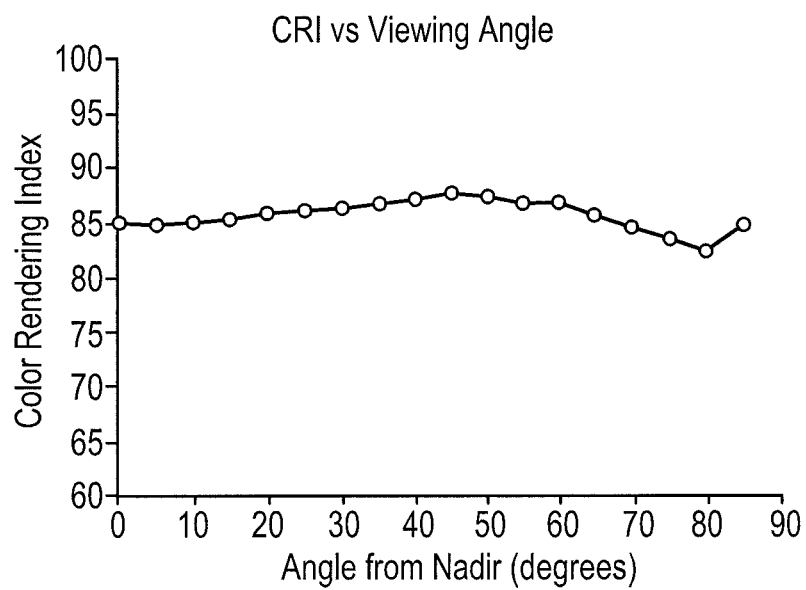

FIG. 24B shows a plot of measured CRI over viewing angle measured using a light fixture similar to the embodiment of a light fixture depicted in FIG. 16.

Figure 25:
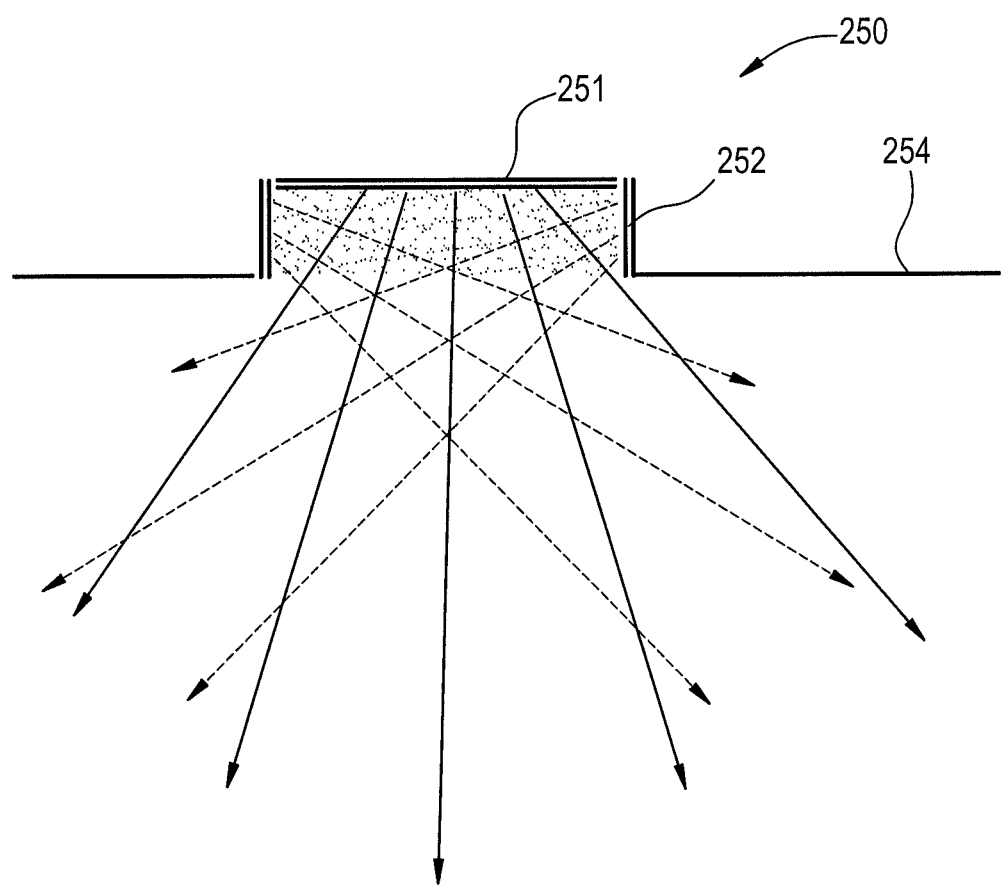

FIG. 25 is a schematic cross-sectional view of an embodiment of a light fixture in accordance with the present inventive subject matter, mounted in a ceiling.

Figure 26:
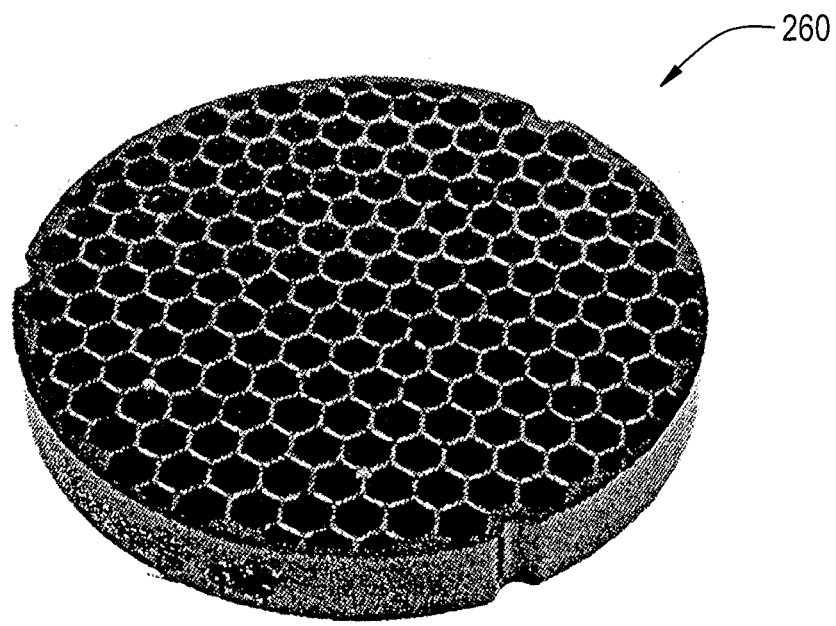

FIG. 26 schematically depicts a representative example of a baffle element 260 suitable for use in accordance with the present inventive subject matter.

Figure 27:
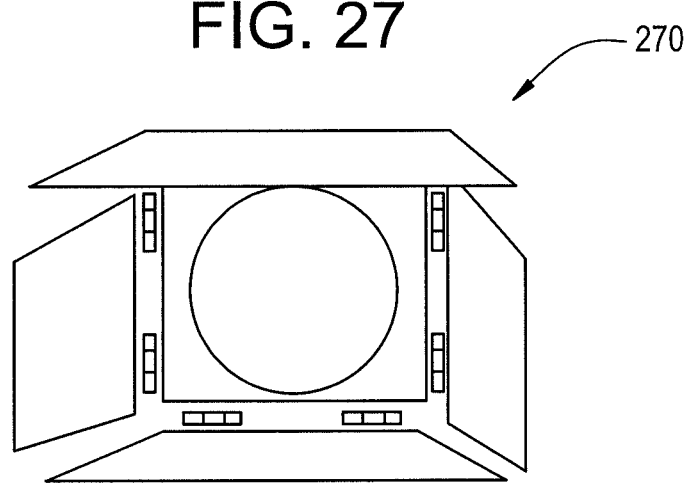

FIG. 27 schematically depicts a representative example of a baffle element 270 suitable for use in accordance with the present inventive subject matter.

Figure 28:
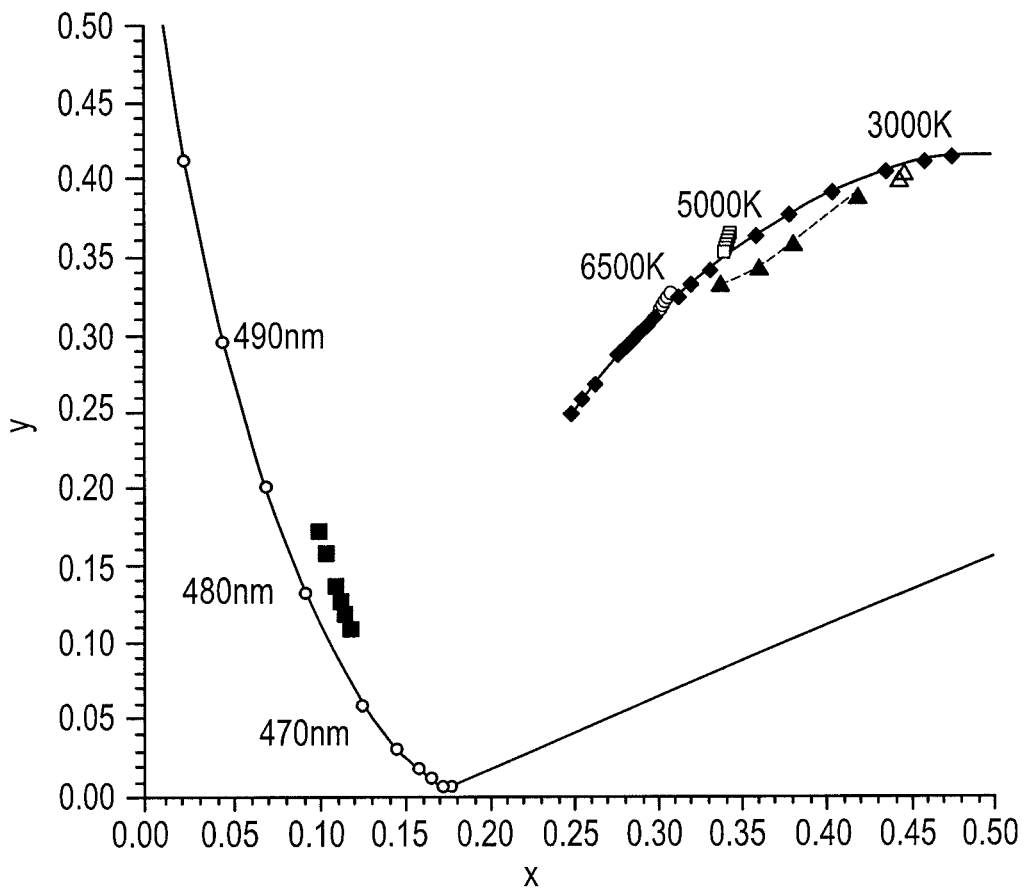

FIG. 28 shows the color points of light emitted by representative examples of the two types of LEDs used in the fabrication of the first light engine (the "sky"), and light emitted by the two types of LEDs used in the fabrication of the second light engine (the "sun") plotted on a portion of the CIE 1931 Chromaticity Diagram.

Figure 29:

FIG. 29 is a photo of an embodiment of an artificial skylight in accordance with the present inventive subject matter, where the sky ("first light engine") has a color point of (0.3135, 0.3237), and the sun ("second light engine") has a color point of (0.3451, 0.3516).

Figure 30:

FIG. 30 is a photo of an embodiment of an artificial skylight in accordance with the present inventive subject matter, where the sky ("first light engine") has a color point of (0.2383, 0.2472), and the sun ("second light engine") has a color point of (0.3451, 0.3516).

DETAILED DESCRIPTION

The present inventive subject matter will be described more fully hereinafter with reference to the accompanying drawings, in which embodiments of the inventive subject matter are shown. However, this inventive subject matter should not be construed as being limited to the embodiments set forth herein. Rather, these embodiments are provided so that this disclosure will be thorough and complete, and will fully convey the scope of the inventive subject matter to those skilled in the art. Like numbers refer to like elements throughout.

As used herein the term "and/or" includes any and all combinations of one or more of the associated listed items.

The term "plurality," as used herein, means two or more, i.e., it encompasses two, three, four, five, etc. For example, the expression "plurality of positions" encompasses two positions, three positions, four positions, etc.

The terminology used herein is for the purpose of describing particular embodiments only and is not intended to be limiting of the inventive subject matter. As used herein, the singular forms "a", "an" and "the" are intended to include the plural forms as well, unless the context clearly indicates otherwise.

The terms "comprises" and/or "comprising," when used in this specification, specify the presence of stated features, operations, elements, and/or components, but do not preclude the presence or addition of one or more other features, operations, elements, components, and/or groups thereof. A statement that something comprises an element (e.g., an element of a type or group) does not preclude the presence of additional elements of the same type (for instance, recitation that a light fixture "comprises a first light engine" does not preclude the light fixture from having a second light engine or other light engines). The term "include" (or the like, e.g., "including") also specify the presence of the listed item or items, but does not preclude the presence or addition of other items (e.g., "including" means including but not limited to).

When an element such as a layer, region or substrate is referred to herein as being "on" another element, it can be in or on the other element, and/or it can be directly on the other element, and it can be in direct contact or indirect contact with the other element (e.g., intervening elements may also be present). In contrast, when an element is referred to herein as being "directly on" another element, there are no intervening elements present. A statement that a first element is "on" a second element is synonymous with a statement that the second element is "on" the first element.

When an element is referred to herein as being "connected" to another element, it can be directly connected to the other element, or intervening elements may be present. In contrast, when an element is referred to herein as being "directly connected" to another element, there are no intervening elements present in at least one location where the elements are connected.

The expression "in contact with," as used herein, means that a first structure that is in contact with a second structure is in direct contact with the second structure or is in indirect contact with the second structure. The expression "in indirect contact with" means that the first structure is not in direct contact with the second structure, but that there are a plurality of structures (including the first and second structures), and each of the plurality of structures is in direct contact with at least one other of the plurality of structures (e.g., the first and second structures are in a stack and are separated by one or more intervening layers). The expression "direct contact", as used in the present specification, means that the first structure which is "in direct contact" with a second structure is touching the second structure and there are no intervening structures between the first and second structures at least at some location.

A statement herein that two components in a device are "electrically connected," means that there are no components electrically between the components that affect the function or functions provided by the device. For example, two components can be referred to as being electrically connected, even though they may have a small resistor between them which does not materially affect the function or functions provided by the device (indeed, a wire connecting two components can be thought of as a small resistor); likewise, two components can be referred to as being electrically connected, even though they may have an additional electrical component between them which allows the device to perform an additional function, while not materially affecting the function or functions provided by a device which is identical except for not including the additional component; similarly, two components which are directly connected to each other, or which are directly connected to opposite ends of a wire or a trace on a circuit board, are electrically connected. A statement herein that two components in a device are "electrically connected" is distinguishable from a statement that the two components are "directly electrically connected", which means that there are no components electrically between the two components.

Although the terms "first", "second", etc. may be used herein to describe various openings, light exit regions, edges, directions, light sources, color points, light engines, parts, major surfaces, sides, wavelength ranges and correlated color temperatures, these openings, light exit regions, edges, directions, light sources, color points, light engines, parts, major surfaces, sides, wavelength ranges and correlated color temperatures should not be limited by these terms. These terms are only used to distinguish one opening, light exit region, edge, direction, light source, color point, light engine, part, major surface, side, wavelength range and correlated color temperature from another opening, light exit region, edge, direction, light source, color point, light engine, part, major surface, side, wavelength range and correlated color temperature. Thus, a first opening, light exit region, edge, direction, light source, color point, light engine, part, major surface, side, wavelength range and correlated color temperature discussed below could be termed a second opening, light exit region, edge, direction, light source, color point, light engine, part, major surface, side, wavelength range and correlated color temperature without departing from the teachings of the present inventive subject matter.

Relative terms, such as "front", "back", "behind", etc., are used herein to describe spatial relationships among elements or structures. Such relative terms are intended to encompass different orientations of the device in addition to the orientation described. For example, if a device is turned 180 degrees, an element in front of the light fixture (or in front of another component) would in the back of the light fixture (or behind the other component) from the same perspective prior to turning the device 180 degrees.

The expression "defines (or at least partly defines)", e.g., as used in the expression "The sidewall defines (or at least partly defines) a space" means that the element or feature that is defined, or at least partly defined by the structure (e.g., the sidewall in this example) is defined by that structure or is defined by that structure in combination with one or more additional structures.

The expression "defines at least part", e.g., as used in the expression "the sidewall comprises a second edge that defines at least part of a second edge-defined region" means that the element or feature that is defined, or at least part of which is defined by the structure, (e.g., the sidewall in this example) is defined by that structure or is defined by that structure in combination with one or more additional structures.

The expression "axis of light distribution", as used herein in connection with light output from one or more light sources (and/or light one or more light engines), means an axis of the light from a light source (and/or from a light engine), a direction of maximum brightness of a distribution of light, or a mean direction of a distribution of light. In other words, in the case of "a mean direction of a distribution of light," (1) if there is provided a light source (or a light engine) in which the distribution of the brightness of emitted light (or light exiting the light engine) is non-Lambertian, the axis of light distribution might coincide with the an axis of the light source or light engine (e.g., because the mean direction of the maxima lies on the axis of the light source or light engine), even though the maximum directions of brightness do not themselves lie on the axis of the light source or light engine, or (2) if the maximum brightness is in a first direction, a brightness in a second direction ten degrees to one side of the first direction is larger than a brightness in a third direction ten degrees to an opposite side of the first direction, the mean direction of light emission would be moved somewhat toward the second direction as a result of the brightnesses in the second direction and the third direction.

The expression "correlated color temperature" ("CCT") is used according to its well known meaning to refer to the temperature of a blackbody that is nearest in color, in a well-defined sense (i.e., can be readily and precisely determined by those skilled in the art). Persons of skill in the art are familiar with correlated color temperatures, and with Chromaticity diagrams that show color points to correspond to specific correlated color temperatures and areas on the diagrams that correspond to specific ranges of correlated color temperatures. Light can be referred to as having a correlated color temperature even if the color point of the light is on the blackbody locus (i.e., its correlated color temperature would be equal to its color temperature); that is, reference herein to light as having a correlated color temperature does not exclude light having a color point on the blackbody locus.

The term "edge" of a structure (e.g., "bottom edge of the first sidewall"), means any portion (or portions) of the structure where there is a non-flat topography (e.g., a location where a surface ends, a location where a first planar surface meets a second planar surface, or a location where a curved or other non-planar surface meets a planar surface, or a location where a first non-planar surface meets a second non-planar surface, etc.).

A "light engine" can be any structure (or combination of structures) from which light exits. In many cases, a light engine consists of one or more light sources plus one or more mechanical elements, one or more optical elements and/or one or more electrical elements. In many cases, a light engine is a component of a light fixture, i.e., it is not a complete light fixture, but it can be a discrete group or set of LEDs that is spatially segregated and controlled as a unit. In some embodiments, for instance, a light engine in a light fixture can be a discrete set of LEDs (e.g., an array of LEDs) mounted to a board (e.g., a printed circuit board) that is separate from one or more other light engines in the light fixture. In some embodiments, a larger board can comprise different sets or groups of LEDs occupying different portions of the board, and thereby comprise multiple light engines. A light engine can, for example, comprise chip-on-board, packaged LEDs, secondary optics and/or control/drive circuitry. In some embodiments, a light fixture can comprise a first light engine comprising multiple LEDs on a first board, and a second light engine comprising multiple LEDs on a second board. In some embodiments, a light engine can comprise multiple LEDs spaced from each other (in the aggregate) in one dimension, in two dimensions or in three dimensions. For example, a first light engine can be mounted adjacent or spaced laterally from but on the same plane with a second light engine and thereby spaced in one dimension. A first light engine can be positioned adjacent or spaced from a second light engine but positioned at an angle or on a second plane from the second light engine and thereby in two dimensions. A first light engine can be offset from a second light engine in two or three dimensions. A first light engine can be offset or positioned relative to two, three or more dimensions of one or more other light engines. In some embodiments, a light engine can comprise a single light source (e.g., a single LED), or an array of light sources (e.g., a plurality of LEDs, a plurality of other light sources, or a combination of one or more LEDs and/or one or more other light sources). In some embodiments, a plurality of light sources (e.g., a plurality of LEDs) can be on a board and controlled together, for example, a control device (that controls color point of a mixture of light from the plurality of light sources, and/or that controls brightness of light emitted from one or more of the plurality of light sources, etc.) can control a plurality of light sources on a board (and/or can control all of the light sources on a board).

The expression "light exit region" (e.g., "at least a first light exit region is at a boundary of the space"), means any region through which light passes (e.g., as it travels from a space which is to one side of the light exit region to the other side of the light exit region, i.e., as it exits the space through the light exit region). For example, if a light fixture has a cylindrical surface that defines an internal space (closed at the top and open at the bottom), light can exit the space by traveling through the circular light exit region at the bottom of the cylindrical surface (i.e., such circular light exit region is defined by the lower edge of the cylindrical surface). Such a light exit region can be open, or it can be partially or completely occupied by a structure that is at least partially light-transmitting (e.g., transparent or translucent). For example, a light exit region can be an opening in an opaque structure (through which light can exit), a light exit region can be a transparent region in an otherwise opaque structure, a light exit region can be an opening in an opaque structure that is covered by a lens or a diffuser, etc.

The expression "defining a space" (e.g., in the expression "the first sidewall defines a space") means that portions of the structure which is being described as defining the space objectively define an identifiable space. As purely representative examples for illustration, a cylindrical surface defines a cylindrical space inside the cylindrical surface; likewise, a surface that is cylindrical except for not having closed ends (i.e., not having circular regions at the top and bottom) and having holes and/or gaps can define a cylindrical space; likewise, a series of planar surfaces extending around a region can define a space (e.g., four planar regions having respective edges that abut two neighbors on either side to define right angles can together define a rectangular prismatic or a square prismatic space); likewise, one or more irregular, non-flat surfaces can together define a space where each point in the space is along a line segment connecting respective points on one or more of the surfaces, etc.

The expression "boundary of the space" means any portion of an exterior of a space. For example, in the case of a cylindrical space, a "boundary of the space" can be either of the circular regions at the exterior of the space, or it can be the curved side of the exterior of the space (i.e., the entire exterior except for the two circular regions), or any portion of either of the circular regions or any portion of the curved side. Similarly, in the case of a space in the shape of a square prism or a rectangular prism, a "boundary of the space" can be any of the sides of the prism or any portion of any of the sides of the prism.

The expression "substantially flat," as used herein (e.g., in the expression "the first light exit surface can be substantially flat and rectangular") means that at least 90% of the points in a surface of the structure that is being characterized as substantially flat are located between a pair of planes which are parallel and which are spaced from each other by a distance of not more than 25% of the largest dimension of the surface (and in some cases, not more than 15%, not more than 10% or not more than 5% of the largest dimension of the surface).

The expression "visibly distinct color" means that a human with normal vision would be able to detect a difference in color between lights (e.g., between light that exits from a first light engine and light that exits from a second light engine).

The expression "light that exits a light engine is of a first color point" (and similar or analogous expressions) means the color point of light (or a mixture of light) exiting the light engine, i.e., if light that exits the light engine is all of a single color point (e.g., if the light engine includes only a single light source), the light that exits the light engine is of that color point, and if light that exits the light engine is a mixture of light of different color points (e.g., if the light engine includes two or more light sources that emit light of different color points), the light that exits the light engine is of the color point that the mixture of light is.

Unless otherwise defined, all terms (including technical and scientific terms) used herein have the same meaning as commonly understood by one of ordinary skill in the art to which this inventive subject matter belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein. It will also be appreciated by those of skill in the art that references to a structure or feature that is disposed "adjacent" another feature may have portions that overlap or underlie the adjacent feature.

The color of visible light emitted by a light source, and/or the color of a mixture visible light emitted by a plurality of light sources can be represented on either the 1931 CIE (Commission International de l'Eclairage) Chromaticity Diagram or the 1976 CIE Chromaticity Diagram. Persons of skill in the art are familiar with these diagrams, and these diagrams are readily available (e.g., by searching "CIE Chromaticity Diagram" on the internet).

The CIE Chromaticity Diagrams map out the human color perception in terms of two CIE parameters, namely, x and y (in the case of the 1931 diagram) or u' and v' (in the case of the 1976 diagram). Each point (i.e., each "color point") on the respective Diagrams corresponds to a particular hue. For a technical description of CIE chromaticity diagrams, see, for example, "Encyclopedia of Physical Science and Technology", vol. 7, 230-231 (Robert A Meyers ed., 1987). The spectral colors are distributed around the boundary of the outlined space, which includes all of the hues perceived by the human eye. The boundary represents maximum saturation for the spectral colors.

The 1931 CIE Chromaticity Diagram can be used to define colors as weighted sums of different hues. The 1976 CIE Chromaticity Diagram is similar to the 1931 Diagram, except that similar distances on the 1976 Diagram represent similar perceived differences in color.

The expression "hue", as used herein, means light that has a color shade and saturation that correspond to a specific point on a CIE Chromaticity Diagram, i.e., a point that can be characterized with x, y coordinates on the 1931 CIE Chromaticity Diagram or with u', v' coordinates on the 1976 CIE Chromaticity Diagram.

In the 1931 Diagram, deviation from a point on the Diagram (i.e., "color point") can be expressed either in terms of the x, y coordinates or, alternatively, in order to give an indication as to the extent of the perceived difference in color, in terms of MacAdam ellipses (or plural-step MacAdam ellipses). For example, a locus of points defined as being ten MacAdam ellipses (also known as "a ten-step MacAdam ellipse") from a specified hue defined by a particular set of coordinates on the 1931 Diagram consists of hues that would each be perceived as differing from the specified hue to a common extent (and likewise for loci of points defined as being spaced from a particular hue by other quantities of MacAdam ellipses).

A typical human eye is able to differentiate between hues that are spaced from each other by more than seven MacAdam ellipses (and is not able to differentiate between hues that are spaced from each other by seven or fewer MacAdam ellipses).

Since similar distances on the 1976 Diagram represent similar perceived differences in color, deviation from a point on the 1976 Diagram can be expressed in terms of the coordinates, u' and v', e.g., distance from the point=$(\Delta u'^2 + \Delta v'^2)'$. This formula gives a value, in the scale of the u' v' coordinates, corresponding to the distance between points. The hues defined by a locus of points that are each a common distance from a specified color point consist of hues that would each be perceived as differing from the specified hue to a common extent.

A series of points that is commonly represented on the CIE Diagrams is referred to as the blackbody locus. The chromaticity coordinates (i.e., color points) that lie along the blackbody locus correspond to spectral power distributions that obey Planck's equation: $E(\lambda)=A\lambda^{-5}/(e^{(B/T)}-1)$, where E is the emission intensity, $\lambda$ is the emission wavelength, T is the temperature of the blackbody and A and B are constants. The 1976 CIE Diagram includes temperature listings along the blackbody locus. These temperature listings show the color path of a blackbody radiator that is caused to increase to such temperatures. As a heated object becomes incandescent, it first glows reddish, then yellowish, then white, and finally bluish. This occurs because the wavelength associated with the peak radiation of the blackbody radiator becomes progressively shorter with increased temperature, consistent with the Wien Displacement Law. Illuminants that produce light that is on or near the blackbody locus can thus be described in terms of their color temperature.

The expression "dominant wavelength", is used herein according to its well known and accepted meaning to refer to the perceived color of a spectrum, i.e., the single wavelength of light which produces a color sensation most similar to the color sensation perceived from viewing light emitted by the light source, as opposed to "peak wavelength", which is well known to refer to the spectral line with the greatest power in the spectral power distribution of the light source. Because the human eye does not perceive all wavelengths equally (it perceives yellow and green better than red and blue), and because the light emitted by many solid state light emitters (e.g., light emitting diodes) is actually a range of wavelengths, the color perceived (i.e., the dominant wavelength) is not necessarily equal to (and often differs from) the wavelength with the highest power (peak wavelength). A truly monochromatic light such as a laser has a dominant wavelength that is the same as its peak wavelengths.

The expression "peak intensity angle" is used herein according to its well known and accepted meaning to refer to an angle, relative to a plane, that a largest illuminance of light emitted from a light source (or light sources) is travelling, i.e., for each angle (e.g., whole numbers, i.e., 0 degrees, 1 degree, 2 degrees . . . 89 degrees and 90 degrees) relative to a defined plane, the illuminance of light travelling at such angle relative to the plane is determined, and the angle for which the largest illuminance is determined is the "peak intensity angle."

A statement that "light output from a first light engine provides a first CS value" (or the like) means that the light output from the first light engine would, in the absence of any other light, provide the first CS value. That is, such a statement does not indicate that the light output from the first light engine does not mix with other light from one or more other light engines, or that the total light output from a light fixture that comprises the first light engine provides such first CS value (e.g., the light output from the light fixture can comprise light output from at least a second light engine, and a mixture of light output from the first light engine and the second light engine can have an aggregate CS value that differs from the first CS value.

It is well known that light sources that emit light of respective differing hues (two or more) can be combined to generate mixtures of light that have desired hues (e.g., non-white light corresponding to desired color points or white light of desired color temperature, etc.). It is also well known that the color point produced by mixtures of colors can readily be predicted and/or designed using simple geometry on a CIE Chromaticity Diagram. It is further well known that starting with the notion of a desired mixed light color point, persons of skill in the art can readily select light sources of different hues that will, when mixed, provide the desired mixed light color point. For example, persons of skill in the art can select a first light engine (e.g., comprising a light emitting diode and phosphor), plot the color point of the light exiting from the first light engine (i.e., a first color point) on a CIE Chromaticity Diagram, plot a desired range of color points (or a single desired color point) for mixed light, and draw one or more line segments through the desired range of color points (or the single color point) for the mixed light such that the line segment(s) extend beyond the desired color point(s). Each line segment drawn in this way will have one end at the first color point, will pass through the range for the desired mixed light color point (or the desired single color point), and will have its other end at a second color point. A second light engine can be provided from which light of the second color point exits, and when the first light engine and a second light engine are energized so that light exits from them, the color point of the mixed light will necessarily lie along a line segment connecting the first color point and the second color point, and the location of the color point of the mixed light along the line segment will be dictated by (namely, proportional to) the relative brightnesses of the respective light that exits from the first and second light engines. That is, the greater the proportion of the mixed light that is from the second light engine, the closer the color point of the mixed light is to the second color point; this relationship is geometrically proportional, i.e., the fraction of the length of the line segment that the color point of the mixed light is spaced from the first color point is equal to the fraction of the mixed light that is from the second light engine (and vice-versa), or, in geometric terms, the ratio of (1) the distance from the first color point to the color point of the mixed light, divided by (2) the distance from the first color point to the second color point will be equal to the ratio of the brightness (in lumens) of the first light engine divided by the brightness (in lumens) of the combination of light in the mixed light. Accordingly, once one identifies light sources (or light engines) that provide the endpoints of a line segment that extends through the desired mixed light color point, the desired mixed light color point can be obtained by calculating the relative brightnesses of the first and second light sources (or light engines) necessary to arrive at the desired mixed light color point.

Where more than two light sources (and/or light engines) are used (e.g., where there are mixed light of a first color point from a first light source, light of a second color point from a second light source, and light of a third color point from a third light source), the geometrical relationships can be used to ensure that the desired mixed light color point is obtained (e.g., conceptually, the color point of a sub-mixture of light from the first light source (or the first light engine) and the second light source (or the second light engine) can be determined, and then the color point of a mixture of sub-mixture (having a brightness of the combined brightnesses of the first light source (or the first light engine) and the second light source (or the second light engine)) and the third light source (or the third light engine) can be determined, and the range of mixed light color points that can be reached is defined by the perimeter obtained from drawing lines connecting the respective color points of the light sources (and/or light engines).

As noted above, in accordance with a first aspect of the present inventive subject matter, there are provided light fixtures (artificial skylights), in which at least a portion of a first light engine resembles a sky (e.g., a surface of the first light engine looks like the sky to a viewer), and light exiting from a second light engine has one or more characteristics that resemble that (or those) of at least a portion of light emitted by (and received from) the sun.

Figure 1:
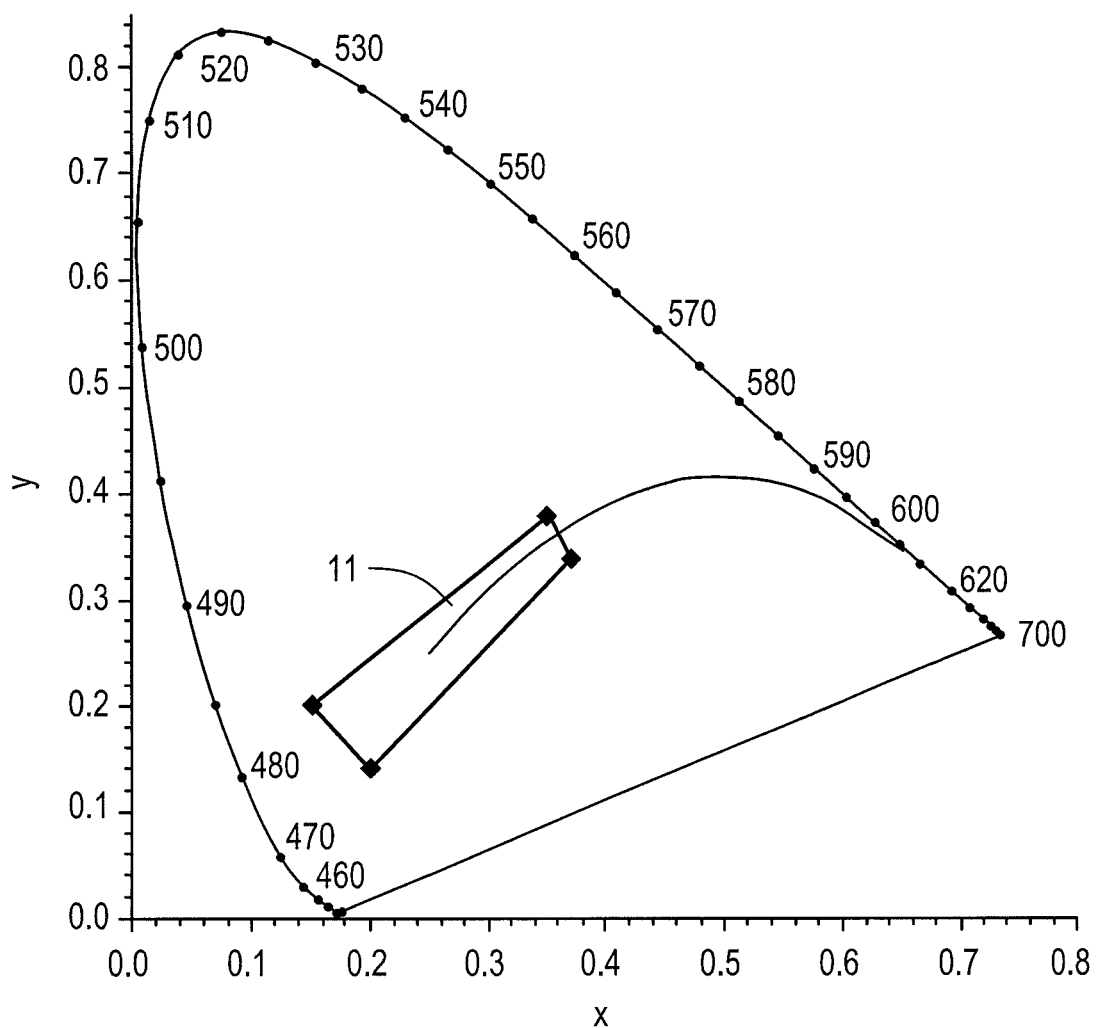
FIG. 1 depicts (on a 1931 CIE Chromaticity Diagram) a region within which is located a first representative range of color points for a first light engine for use in light fixtures in accordance with the present inventive subject matter.
Figure 2:
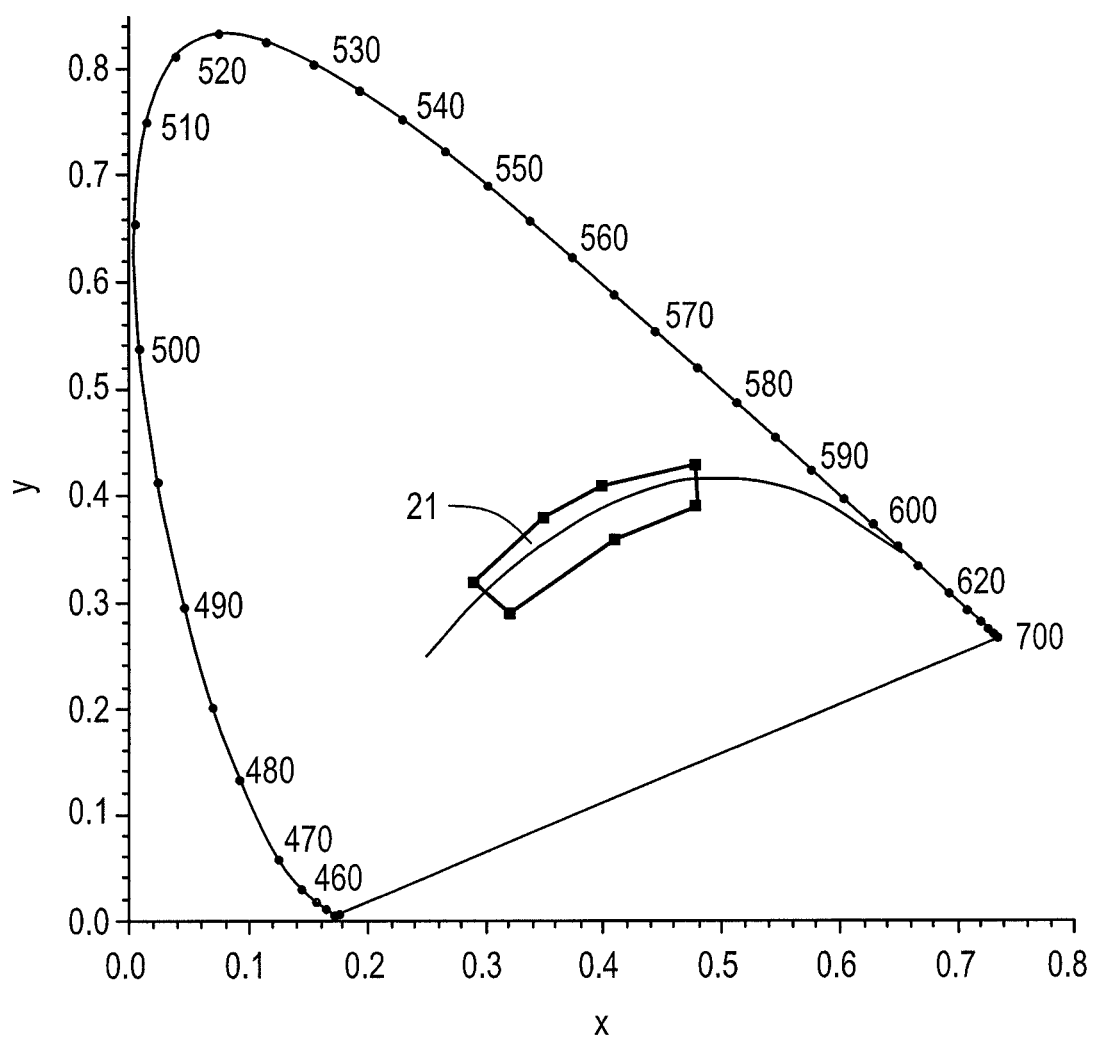
FIG. 2 depicts (on a 1931 CIE Chromaticity Diagram) a region within which is located a first representative range of color points for a second light engine for use in light fixtures in accordance with the present inventive subject matter.
Figure 3A:
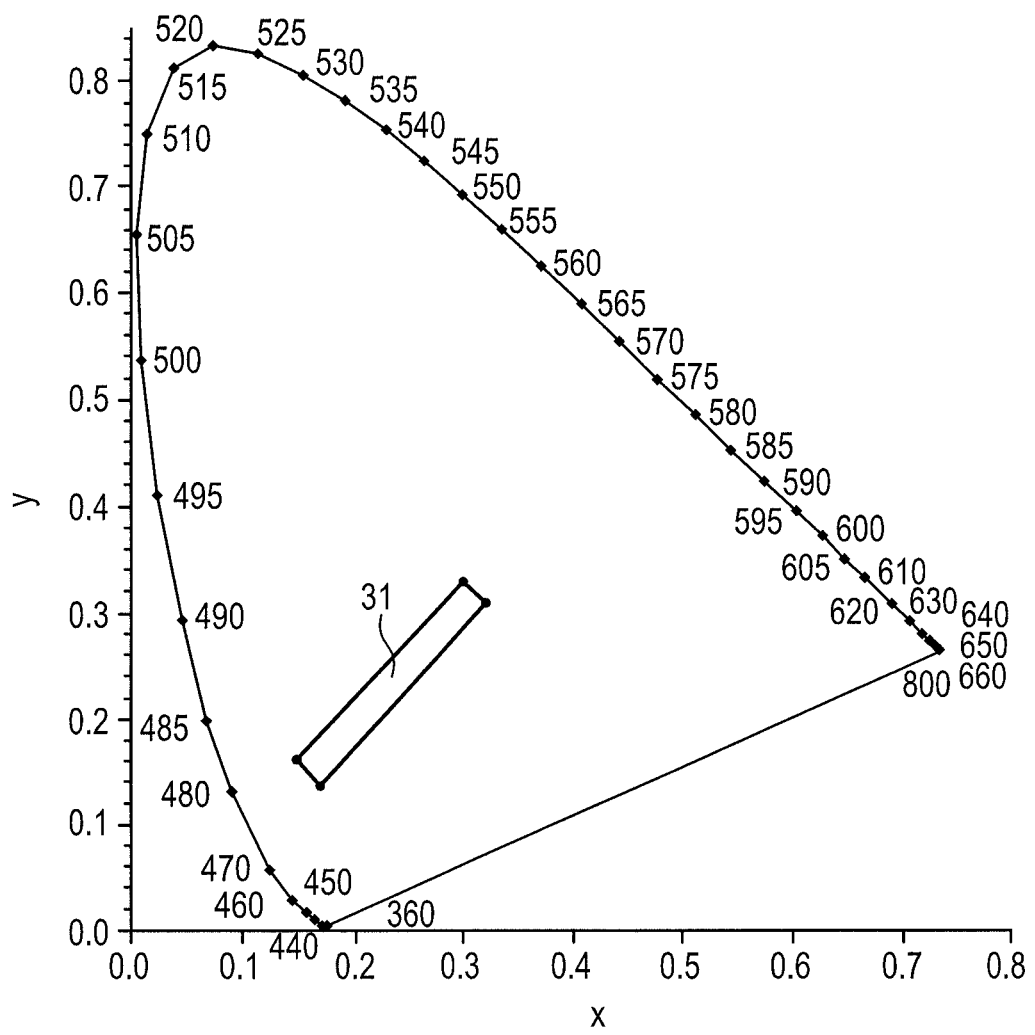
FIG. 3A depicts (on a 1931 CIE Chromaticity Diagram) a region within which is located a second representative range of color points for a first light engine for use in light fixtures in accordance with the present inventive subject matter.
Figure 3B:
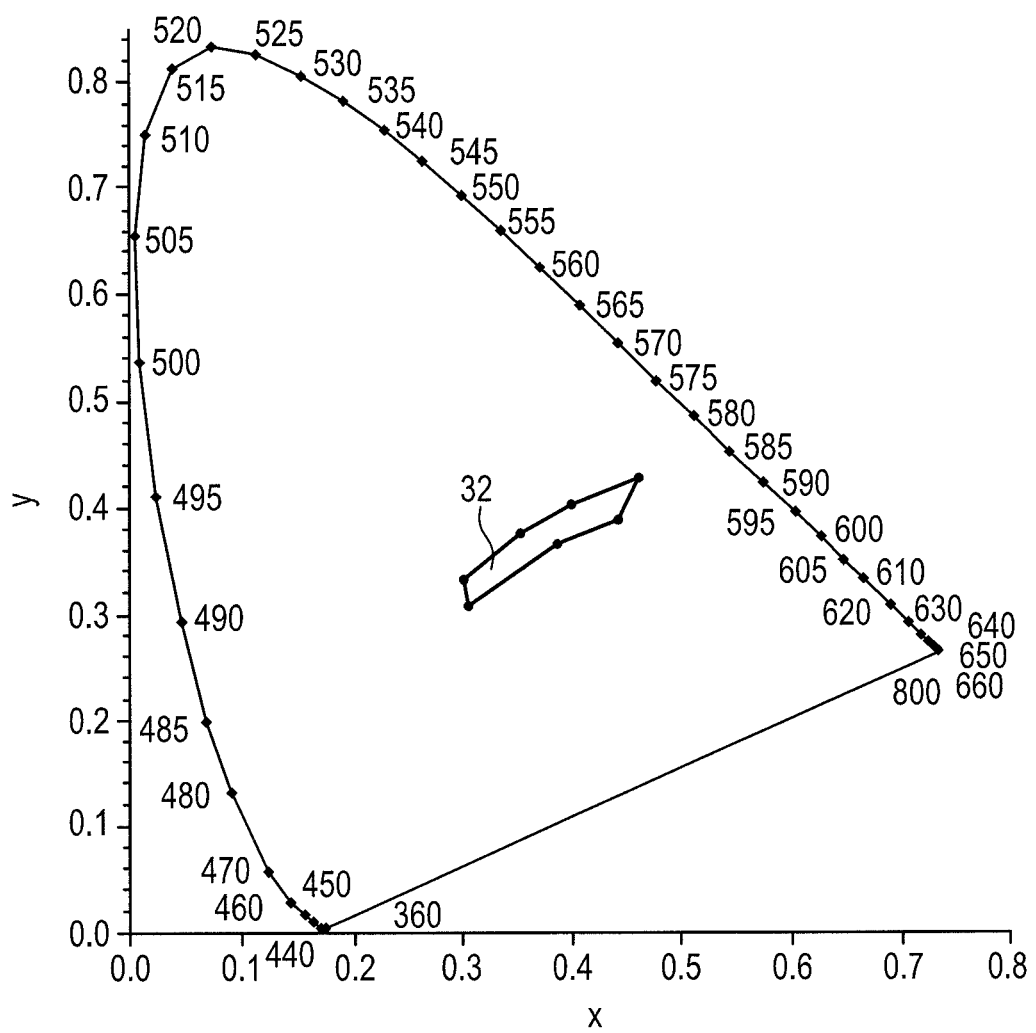
FIG. 3B depicts (on a 1931 CIE Chromaticity Diagram) a region within which is located a second representative range of color points for a second light engine for use in light fixtures in accordance with the present inventive subject matter.

In some embodiments of light fixtures in accordance with the first aspect of the present inventive subject matter, including some embodiments that include or do not include any of the features described herein:

the light fixture comprises at least a first light engine and a second light engine;

light exiting the first light engine (i.e., upon supplying electricity to a light source of the first light engine) has x, y color coordinates which define a point on a 1931 CIE Chromaticity Diagram which is within a quadrilateral area with vertices having x, y coordinates of (0.37, 0.34), (0.35, 0.38), (0.15, 0.20), and (0.20, 0.14) (FIG. 1 is a plot, on a 1931 CIE Chromaticity Diagram, of a region 11 defined as such, i.e., the quadrilateral area with vertices having such x, y coordinates) (and in some embodiments, within a quadrilateral area with vertices having x, y coordinates of (0.32, 0.31), (0.30, 0.33), (0.15, 0.17), and (0.17, 0.14), FIG. 3a being a plot, on a 1931 CIE Chromaticity Diagram, of a region 31 defined as such);

light exiting the second light engine (i.e., upon supplying electricity to a light source of the second light engine) has x, y color coordinates which define a point on a 1931 CIE Chromaticity Diagram which is within an area with vertices having x, y coordinates of (0.29, 0.32), (0.32, 0.29), (0.41, 0.36), (0.48, 0.39), (0.48, 0.43), (0.40, 0.41), and (0.35, 0.38) (FIG. 2 is a plot, on a 1931 CIE Chromaticity Diagram, of a region 21 defined as such, i.e., the area with vertices having such x, y coordinates) (and in some embodiments, within an area with vertices having x, y coordinates of (0.30, 0.34), (0.30, 0.30), (0.39, 0.36), (0.45, 0.39), (0.47, 0.43), (0.40, 0.41), and (0.35, 0.38), FIG. 3b being a plot, on a 1931 CIE Chromaticity Diagram, of a region 32 defined as such); and the color point (i.e., the combination of x, y color coordinates) of the light exiting the first light engine may be but typically is not the same as the color point of the light exiting the second light engine.

A first group of embodiments within the first aspect of the present inventive subject matter includes light fixtures that comprise at least first and second light engines and a first sidewall, in which:

the first light engine comprises at least a first light exit surface;

the first sidewall defines a space;

at least a first light exit region is at a boundary of the space;

the first light engine is positioned and oriented such that at least some light that exits the first light exit surface passes through at least part of the space and exits the space through the first light exit region; and the second light engine is positioned and oriented such that at least some light that exits the second light engine exits the space through the light exit region.

A second group of embodiments within the first aspect of the present inventive subject matter includes light fixtures that comprise a first light engine and at least a first sidewall, in which:

the first light engine comprises at least a first light exit surface;

the first sidewall comprises at least a second light exit surface;

the first sidewall defines a space;

at least a first light exit region is at a boundary of the space;

the first light engine is positioned and oriented such that at least some light that exits the first light exit surface passes through at least part of the space and exits the space through the first light exit region; and the first sidewall is positioned and oriented such that at least some light that exits the second light exit surface exits the space through the light exit region.

A third group of embodiments within the first aspect of the present inventive subject matter includes light fixtures that comprise at least first and second light engines, in which:

the first light engine comprises at least a first light exit surface;

the first and second light engines are positioned and oriented such that at least some light that exits the first light exit surface travels to a region (e.g., in an office or a room) to which at least some light that exits the second light engine travels.

As noted above, each of the first, second and third groups of embodiments in accordance with the first aspect of the present inventive subject matter comprises a first light engine that comprises at least a first light exit surface, and at least a portion of the first light engine (namely, the first light exit surface) resembles a view of the sky, e.g., a blue sky.

In addition, as noted above, in some embodiments in accordance with the first aspect of the present inventive subject matter, light exiting the first light engine (i.e., upon supplying electricity to a light source of the first light engine) has x, y color coordinates which define a point on a 1931 CIE Chromaticity Diagram which is within a quadrilateral area with vertices having x, y coordinates of (0.37, 0.34), (0.35, 0.38), (0.15, 0.20), and (0.20, 0.14) (such area is plotted in FIG. 1) (and in some embodiments, within a quadrilateral area with vertices having x, y coordinates of (0.32, 0.31), (0.30, 0.33), (0.15, 0.17), and (0.17, 0.14)).

Light fixtures in accordance with the first aspect of the present inventive subject matter can, in some embodiments, have only a single light engine that has at least one light exit surface that resembles a view of the sky (i.e., part of the sky), or they can have any number of such light engines. Accordingly, each light engine that comprises a light exit surface that resembles a view of the sky (in light fixtures that comprise more than one such light engine) can have any of the features of a "first light engine" as described herein. In some embodiments, the first light engine is not extremely bright, is blue-ish, is substantially uniform, and the illumination pattern it creates in space beyond the light exit region is substantially non-directional.

Any "first light engine" (i.e., a light engine that comprises at least a first light exit surface that resembles a view of the sky) can have a single light exit surface that resembles a view of the sky or any number of light exit surfaces that each resemble a view of the sky. Accordingly, each light exit surface that resembles a view of the sky (in light engines that comprise more than one such light exit surface) can have any of the features of a "first light exit surface" as described herein.

The first light engine, and the first light exit surface (or surfaces) of the first light engine, can each be of any suitable shape and size, and persons of skill in the art can readily select a suitable shape for the first light engine and a suitable shape for the first light exit surface. For example, the first light engine and/or the first light exit surface can be any combination of flat (or substantially flat), curved (e.g., concave, convex, or a combination of concave regions and convex regions; dome-shaped, elliptical, parabolic), square, rectangular, circular, oval, stepped, of a shape that has a repeating pattern, irregular or random, mosaic, moth's eye, or any other shape. For example, the first light exit surface can be substantially flat and rectangular, substantially flat and square, substantially flat and circular, dome-shaped and rectangular, dome-shaped and square, dome-shaped and circular, etc.

The first light engine can comprise any suitable light engine structure, and persons of skill in the art can readily select such suitable light engine structures. The visible surface of the first light engine can be diffuse, specular or any combination thereof. The expression "specular" is used in accordance with its well known meaning to refer to mirror-like reflectivity, whereas "diffuse" (in the context of reflectivity) is used to refer to non-mirror-like reflectivity. In some preferred embodiments in accordance with the present inventive subject matter, including some embodiments that include or do not include any of the features described herein, the visible surface of the first light engine has a specular glass-like finish, similar to a clear window pane.

One representative example of a suitable light engine that can be employed as a first light engine in accordance with the first aspect of the present inventive subject matter is a troffer. Persons of skill in the art are familiar with a wide variety of troffers, and any suitable troffer can be employed. Troffers typically comprise a housing that has one or more reflective surfaces (and/or on which a reflective material is coated, or to which one or more reflective layers is laminated, etc.) and to which one or more light sources is attached. Such troffers often comprise one or more reflective surfaces that are slanted or curved to re-direct light (i.e., by reflecting incident light) in a favorable distribution.

Another representative example of a suitable light engine that can be employed as a first light engine in accordance with the first aspect of the present inventive subject matter is an edge-lit panel. Persons of skill in the art are familiar with a wide variety of edge-lit panels, and any suitable edge-lit panel can be employed. As is well known, edge-lit panels typically comprise [1] a reflective housing and/or a reflective surface, [2] a substantially flat waveguide having first and second major surfaces on opposite sides, the waveguide configured to allow light to exit from one major surface more readily than from the other major surface, and [3] a plurality of light sources arranged along one or more of the edges of the waveguide, such that the light sources emit light into the waveguide and the light exits the waveguide through the major surface that faces away from the reflective housing and/or reflective surface (in some cases, including some light that exits the waveguide through a surface other than the major surface that faces away from the reflective housing and/or reflective surface, and [a] is reflected or back into the waveguide, and eventually exits the waveguide through the major surface that faces away from the reflective housing and/or reflective surface, or [b] is reflected away from the waveguide). A representative example of an edge-lit panel is similar to a backlight for a computer monitor or a cell phone backlight, and comprises one or more light sources (e.g., light emitting diodes) that emit light of any color or colors, a back reflector, a light guide panel, optionally one or more diffusion films and optionally one or more optical films (see also the discussion below in connection with FIG. 4); in some embodiments in accordance with the present inventive subject matter, such an edge-lit panel can be modified by removing the back reflector, whereby light can travel through the edge-lit panel, i.e., entering through a back surface of the edge-lit panel and exiting through a front surface of the edge-lit panel, in addition to light emitted by light sources (e.g., light emitting diodes) along an edge or edges of the panel (e.g., where a first light engine is positioned between a second light engine and a first light exit region as defined herein). In any light fixture in accordance with the present inventive subject matter in which an edge-lit panel is employed, a diffusion film (or plural diffusion films) is/are optional and an optical film (or plural optical films) is/are optional (unlike in the case of displays where diffusion films and optical films are essential).

In addition, in light fixtures in accordance with the present inventive subject matter in which an edge-lit panel is employed, light extraction elements that serve in the role of diffusion films (i.e., that provide or enhance diffusion) can optionally be fabricated directly into a light guide panel, and/or onto one or more surfaces of a light guide panel. A representative example of an edge-lit panel that is suitable for use in light fixtures in accordance with the present inventive subject matter is an Essentia flat panel available from Cree, Inc., Durham, N.C. (modified to include LEDs selected in accordance with the present description).

FIG. 4 schematically depicts a representative example of an edge-lit panel 40. Referring to FIG. 4, the edge-lit panel 40 comprises a plurality of LEDs 41, a back reflector 42, a light guide panel 43, a plurality of diffusion films 44 (optional) and a plurality of optical films 45 (optional).

In general, in light fixtures in accordance with the present inventive subject matter in which an edge-lit panel is employed and in which extraction elements are provided, extraction elements in/on the light guide panel and the films may be engineered in ways known to skilled practitioners so as to deliver any desired light distribution. In the case of the first light engine (i.e. the sky) especially desirable light distributions include Lambertian distributions or distributions oriented more perpendicular to the panel.

Another representative example of a suitable light engine that can be employed as a first light engine in accordance with the first aspect of the present inventive subject matter is a direct-lit panel, also known as a back-lit panel. Persons of skill in the art are familiar with a wide variety of direct-lit panels, and any suitable direct-lit panel can be employed. A representative example of a direct-lit panel comprises one or more light sources (e.g., LEDs) that emit light of any color or colors, a back reflector, an optical gap, a diffuser plate, optionally one or more diffusion films and optionally one or more optical films (see also the discussion below in connection with FIG. 5).

Representative examples of back-lit panels that are suitable for use in light fixtures in accordance with the present inventive subject matter are back-lit panels in the LR series available from Cree, Inc., Durham, N.C. (modified to include LEDs selected in accordance with the present description).

FIG. 5 schematically depicts a representative example of a back-lit panel 50. Referring to FIG. 5, the back-lit panel 50 comprises a plurality of LEDs 51, a back reflector 52, an optical gap 53, a diffuser plate 54, a plurality of diffusion films 55 (optional) and a plurality of optical films 56 (optional).

In any light fixture in accordance with the present inventive subject matter in which a back-lit panel is employed, a diffusion film (or plural diffusion films) is/are optional and an optical film (or plural optical films) is/are optional.

Another representative example of a suitable light engine that can be employed as a first light engine in accordance with the first aspect of the present inventive subject matter is a side-lit panel. Persons of skill in the art are familiar with a wide variety of side-lit panels, and any suitable side-lit panel can be employed. A representative example of a side-lit panel comprises one or more light sources (e.g., LEDs) that emit light of any color or colors, a back reflector, an optical gap, a diffuser plate, optionally one or more diffusion films and optionally one or more optical films.

FIG. 6 schematically depicts a representative example of a side-lit panel 60. Referring to FIG. 6, the side-lit panel 60 comprises a plurality of LEDs 61, a back reflector 62, an optical gap 63, a diffuser plate 64, a plurality of diffuser films 65 (optional) and/or a plurality of optical films 65 (optional).

In any light fixture in accordance with the present inventive subject matter in which a side-lit panel is employed, a diffusion film (or plural diffusion films) is/are optional and an optical film (or plural optical films) is/are optional.

As noted above, in some embodiments in accordance with the first aspect of the present inventive subject matter, the first light engine comprises at least a first light exit surface that resembles a sky, e.g., a blue sky. In some embodiments in accordance with the present inventive subject matter, including some embodiments that include or do not include any of the features described herein, the first light engine comprises at least a first light exit surface that resembles a sky that is other than a typical blue sky, e.g., the first light exit surface can resemble a light blue sky, a deep blue sky, an overcast sky, a partly cloudy sky, a stormy sky, etc.

In some embodiments in accordance with the first aspect of the present inventive subject matter, including some embodiments that include or do not include any of the features described herein, the color point of light that exits from the first light engine (or from a region or from respective regions thereof) can be changeable, e.g., based on the time of day, user input or actual conditions (e.g., a user can input a color point) of light to be delivered by the first light engine, or by one or more respective regions of the first light engine), and/or the color point (of the first light engine or respective regions of the first light engine) can automatically change over the course of a day. For example, the first light engine, or respective regions of the first light engine, can deliver light, the color point(s) of which automatically change, over the course of a day, along a curve on a CIE Chromaticity Diagram, e.g., along the blackbody locus (or near it), for example decreasing the correlated color temperature over the course of the day or altering other color characteristics of light delivery.

In some embodiments in accordance with the present inventive subject matter, including some embodiments that include or do not include any of the features described herein, the image of a sky that is viewable can be changeable, e.g., based on the time of day, user input, input from one or more sensors, or any other input. For example, the appearance of the first light exit surface of a first light engine can be adjusted (e.g., selected from among a number of designed images) based on sensing of actual conditions, based on user input (e.g., a user can input a type of sky image to be displayed), based on the time of day (e.g., the sky image can automatically change over the course of a day, such as from morning sky, to mid-day sky, to afternoon sky, to late-afternoon sky, to dusk, etc.), based on a report of actual conditions (e.g., actual conditions can be reported wirelessly or via a wired connection to the light fixture to cause the first light engine to present a sky image that correlates to actual conditions), based on images captured by a camera (e.g., a remote camera can capture images which are transmitted by wire or wirelessly to the light fixture and those actual images can be reproduced by the first light engine), etc. There exist a wide variety of components, apparatus or systems that are configured so as to have one or more light exit surfaces that display an image (which can be unchanging or which can change with any desired frequency). Representative examples of such components, apparatus or systems include (and are not limited to) LED panels with LED backlighting, plasma displays, LED displays, OLED displays, CRT displays, rear-projection screens, etc.

As noted above, each of the first, second and third groups of embodiments in accordance with the first aspect of the present inventive subject matter comprises a second light engine, and light exiting from the second light engine has one or more characteristics that resemble that (or those) of at least a portion of light emitted by (and received from) the sun.

Light fixtures in accordance with the first aspect of the present inventive subject matter can, in some embodiments, have only a single light engine that has one or more characteristics that resemble that (or those) of at least a portion of light emitted by (and received from) the sun, or they can have any number of such light engines. Accordingly, each light engine that has one or more characteristics that resemble that (or those) of at least a portion of light emitted by (and received from) the sun can have any of the features of a "second light engine" as described herein. Thus, light fixtures in accordance with the first aspect of the present inventive subject matter can have two or more light engines that have features of a "second light engine" as described herein.

As noted above, in some embodiments in accordance with the first aspect of the present inventive subject matter, light exiting the second light engine (i.e., upon supplying electricity to a light source of the second light engine) has x, y color coordinates which define a point on a 1931 CIE Chromaticity Diagram which is within an area with vertices having x, y coordinates of (0.29, 0.32), (0.32, 0.29), (0.41, 0.36), (0.48, 0.39), (0.48, 0.43), (0.40, 0.41), and (0.35, 0.38) (such area is plotted in FIG. 2 (and in some embodiments, within an area having vertices having x, y coordinates of (0.30, 0.34), (0.30, 0.30), (0.39, 0.36), (0.45, 0.39), (0.47, 0.43), (0.40, 0.41), and (0.35, 0.38)). That is to say, the light exiting the second light engine is yellow-ish to orange-ish white, and thus resembling the sun.

The second light engine can be of any suitable shape, and persons of skill in the art can readily select a suitable shape for the second light engine.

The second light engine can be any suitable size, and persons of skill in the art can readily select a suitable size.

The second light engine can comprise any suitable structure from which light exits, and persons of skill in the art can readily select such suitable structures.

In some embodiments in accordance with the present inventive subject matter, the second light engine has directionality, i.e., the direction or directions in which at least a portion of light that exits the second light engine is selected by features of elements in the second light engine and/or by orientation of such features (and/or by features of one or more other components in the light fixture that achieve selected directionality for light that exits the second light engine). Persons of skill in the art are familiar with, and are readily capable of, providing light engines that achieve specific directionality characteristics for exiting light (as well as components for altering directionality characteristics for light that has exited such light engines), and all such light engines and components are encompassed in the present description.

A representative example of a suitable device that can be employed as a second light engine in accordance with some embodiments of the present inventive subject matter is a downlight (e.g., a flood light or a spotlight). Persons of skill in the art are familiar with a wide variety of downlights, and any suitable downlight can be employed.

Another representative example of a suitable device that can be employed as a second light engine in accordance with some embodiments of the present inventive subject matter is an edge-lit panel (see the above discussion of edge-lit panels, as well as the discussion below in reference to FIG. 4). Such edge-lit panels can provide selected directionality for light that exits the second light engine, e.g., as discussed above with regard to FIG. 4, edge-lit panels can include specific elements, such as waveguides and/or films, to provide specific directionality features, i.e., to deliver one or more portions of light in particular directions and/or to achieve specific directional characteristics. In some embodiments in accordance with the present inventive subject matter, such an edge-lit panel can be modified by removing the back reflector, whereby light can travel through the edge-lit panel, i.e., entering through a back surface of the edge-lit panel and exiting through a front surface of the edge-lit panel, in addition to light emitted by light sources (e.g., LEDs) along an edge or edges of the panel (e.g., where a second light engine is positioned between a first light engine and a first light exit region as defined herein).

Another representative example of a suitable device that can be employed as a second light engine in accordance with some embodiments of the present inventive subject matter is a direct-lit panel (see the above discussion of direct-lit panels, as well as the discussion below in reference to FIG. 5).

Another representative example of a suitable device that can be employed as a second light engine in accordance with some embodiments of the present inventive subject matter is a side-lit panel (see the above discussion of side-lit panels, as well as the discussion below in reference to FIG. 6).

In some embodiments in accordance with the present inventive subject matter, including some embodiments that include or do not include any of the features described herein, the color point of light and/or wavelength distribution (e.g., selected from among a number of designed wavelength distributions) exiting from the second light engine (or from a region or from respective regions thereof) is changeable, e.g., based on the time of day, user input, input from one or more sensors, or any other input. For example, the color point and/or wavelength distribution of light exiting the second light engine can be adjusted based on sensing of actual conditions, based on user input (e.g., a user can input a color point and/or a wavelength distribution to be delivered), based on the time of day (e.g., the color point and/or wavelength distribution can automatically change over the course of a day). For example, the second light engine, or respective regions of the second light engine, is/are such that the color point(s) and/or wavelength distribution of light that exits therefrom automatically change, over the course of a day, according to one or more designed programs.

As discussed above, some embodiments of light fixtures in accordance with the first aspect of the present inventive subject matter comprise at least a first sidewall.

Some embodiments of light fixtures in accordance with the first aspect of the present inventive subject matter have no sidewall, some have only a single sidewall, and some have more than one sidewall. The sidewall in any light fixtures that have a single sidewall, or any of the sidewalls in any light fixtures that have two or more sidewalls, can have any of the features of a "first sidewall" as described herein. Since some embodiments have no sidewall, reference herein to "the first sidewall" or the like relates only to embodiments that have at least a first sidewall, and does not indicate that every embodiment has a sidewall.

The first sidewall can comprise only a single sidewall element, or it can comprise any number of sidewall elements (in such cases, the first sidewall is the combination of such multiple sidewall elements).

The first sidewall can be of any suitable size and shape.

In some embodiments in accordance with the present inventive subject matter, including some embodiments that include or do not include any of the features described herein, the first sidewall is annular. The expression "annular", as used herein, means a structure that extends around an unfilled region, and which can otherwise be of any general shape, and any cross-sections can be of any shape. For example, "annular" encompasses ring-like shapes which can be defined by rotating any shape about an axis in the same plane as, but spaced from, the shape (one example being where the shape is a rectangle with rounded edges, and a center of the rectangle is a constant distance from a single point on the axis throughout the entire rotation, and where at each stage during the rotation, the rectangle lies in a plane in which the axis also lies; such a shape would be a "circular annular" shape with a uniform substantially rectangular cross-section). "Annular" likewise encompasses shapes which can be defined by rotating a square (or any other two-dimensional shape) about an axis in the same plane as, but spaced from, the square. "Annular" likewise encompasses shapes that can be defined by moving any shape from a first position and orientation, through space along any path without ever moving to a position where part of the shape occupies a space previously occupied by any part of the shape, and eventually returning to the first position and orientation. "Annular" likewise encompasses shapes that can be defined by moving any shape from a first position and orientation, through space along any path without ever moving to a position where part of the shape occupies a space previously occupied by any part of the shape, and eventually returning to the first position and orientation, and where the shape and size of the shape being moved can be altered at any location, and any number of times, during its movement.

In some embodiments in accordance with the present inventive subject matter, including some embodiments that include or do not include any of the features described herein, the first sidewall can be substantially rectangular annular and of substantially uniform rounded rectangular cross-section (edges where surfaces meet are rounded, i.e., such that a cross-section has four rounded corners, i.e., a shape that resembles a rectangular cardboard box with the top and bottom removed).

In some embodiments in accordance with the present inventive subject matter, including some embodiments that include or do not include any of the features described herein, the first sidewall can be substantially rectangular annular and of substantially uniform rectangular cross-section (cross-section has four substantially non-rounded corners, e.g., about 90 degrees each).

In some embodiments in accordance with the present inventive subject matter, including some embodiments that include or do not include any of the features described herein, the first sidewall (or portions of the first sidewall, or sidewall elements that together make up the first sidewall) is substantially vertical, and/or cross-sections of at least a portion of the first sidewall taken perpendicular to a vertical axis (or to any line segment) are substantially uniform, and/or a space defined by the first sidewall would have first and second surfaces that are parallel to each other and perpendicular to regions of the sidewall (e.g., a cubical or orthorhombic space).

In other embodiments in accordance with the present inventive subject matter, including some embodiments that include or do not include any of the features described herein, the first sidewall (or portions of the first sidewall, or sidewall elements that together make up the first sidewall) is slanted (angled) or curved, e.g., the first sidewall defines a three-dimensional space that is a truncated cone, a truncated pyramid, etc., or cross-sections of at least a portion of the first sidewall taken perpendicular to a vertical axis (or to any line segment) increase linearly, geometrically or non-linearly in one direction along the axis or line segment.

In some embodiments in accordance with the present inventive subject matter, including some embodiments that include or do not include any of the features described herein, the first sidewall is configured to be mounted in any suitable space, e.g., a hole in a ceiling structure (or the first sidewall is connected to a housing or is part of a housing that can be mounted in any suitable space), e.g., the external shape of the first sidewall corresponds to the internal shape of a hole in a conventional ceiling structure. In some situations, a hole in a ceiling structure can be made to be of any suitable size.

In some embodiments in accordance with the present inventive subject matter, including some embodiments that include or do not include any of the features described herein, the first sidewall is configured to be mounted in a ceiling of a commercial building, e.g., in a two foot by one foot space or in a one foot by one foot space (or multiples, e.g., two one foot by one foot housings can be mounted in a one foot by two foot space, etc.)(or the first sidewall is connected to a housing or is part of a housing that is configured to be mounted in such a ceiling.

The first sidewall defines (or at least partly defines) a space. In other words, at least a portion of the boundary of the space is defined by at least a portion of the first sidewall. In some embodiments in accordance with the present inventive subject matter, including some embodiments that include or do not include any of the features described herein, at least some points within the space are along respective line segments that connect respective points on the first sidewall (e.g., on opposite sides of the space). In some embodiments in accordance with the present inventive subject matter, including some embodiments that include or do not include any of the features described herein, the first sidewall is annular, and the space comprises every point that is located between a respective pair of points on the first sidewall (e.g., if the first sidewall is circular annular, the space is cylindrical; if the first sidewall is rectangular annular, the space is a rectilinear prism, etc.). In some embodiments in accordance with the present inventive subject matter, including some embodiments that include or do not include any of the features described herein, the first sidewall and one or more other structure(s) define the space, i.e., each point in the space is between two respective points, each of which is on the first sidewall or on one of the one or more other structure(s).

The first sidewall can comprise [1] one or more regions from which light exits into the space, [2] one or more regions that reflect light and/or [3] one or more regions that do not substantially reflect light and from which light does not exit (e.g., a sidewall can be partially transmitting and partially reflecting). That is, the first sidewall can reflect light, transport light, transmit light and/or emit light.

In some embodiments in accordance with the present inventive subject matter, to an observer, a majority of the light exiting the light fixture appears to come from the sidewall (in other words, the sidewall appears to be illuminated). In some of such embodiments, the sidewall appears to have a significantly different color from light that exits from the first light engine (i.e., resembling the sky). This contrast can be very effective in providing the illusion of a skylight.

As noted above, in accordance with a first aspect of the present inventive subject matter, there are provided light fixtures (artificial skylights), in which at least a portion of a first light engine resembles a sky (e.g., a surface of the first light engine looks like the sky to a viewer), and light exiting from a second light engine has one or more characteristics that resemble that (or those) of at least a portion of light emitted by (and received from) the sun; and:

[1] a first group of embodiments within the first aspect of the present inventive subject matter includes light fixtures that comprise at least first and second light engines and a first sidewall, in which:

the first light engine comprises at least a first light exit surface;

the first sidewall defines a space;

at least a first light exit region is at a boundary of the space;

the first light engine is positioned and oriented such that at least some light that exits the first light exit surface passes through at least part of the space and exits the space through the first light exit region; and the second light engine is positioned and oriented such that at least some light that exits the second light engine exits the space through the light exit region;

[2] a second group of embodiments within the first aspect of the present inventive subject matter includes light fixtures that comprise a first light engine and at least a first sidewall, in which:

the first light engine comprises at least a first light exit surface;

the first sidewall comprises at least a second light exit surface;

the first sidewall defines a space;

at least a first light exit region is at a boundary of the space;

the first light engine is positioned and oriented such that at least some light that exits the first light exit surface passes through at least part of the space and exits the space through the first light exit region; and the first sidewall is positioned and oriented such that at least some light that exits the second light exit surface exits the space through the light exit region, and

[3] a third group of embodiments within the first aspect of the present inventive subject matter includes light fixtures that comprise at least first and second light engines, in which:

the first light engine comprises at least a first light exit surface;

the first and second light engines are positioned and oriented such that at least some light that exits the first light exit surface travels to a region (e.g., in an office or a room) to which at least some light that exits the second light engine travels.

In some embodiments in accordance with the first group of embodiments within the first aspect of the present inventive subject matter, the first sidewall comprises an interior wall that extends around and defines a space, and the entirety of the surface (or surfaces) of the interior wall of the first sidewall is/are substantially reflective; in some embodiments in accordance with the first group or the third group within the first aspect of the present inventive subject matter, light exits from a portion of the first sidewall into the space, i.e., the space defined at least in part by the first sidewall; in some embodiments in accordance with the first or the third group within the first aspect of the present inventive subject matter, light exits (into a space) from the entirety of a surface of the first sidewall that extends around and defines the space; in some embodiments in accordance with the first group or the third group within the first aspect of the present inventive subject matter, one portion of an interior wall of the first sidewall (that defines an internal space) is reflective, and light exits from another portion of the first sidewall into the space, etc.

There are many ways that a sidewall can be configured such that it has one or more light exit surface (i.e., such that light exits from at least part of its surface or from at least part of one of its surfaces). For example, a sidewall can be configured such that it has one or more light exit surfaces by:

the sidewall being light-transporting (e.g., translucent or transparent) and comprising one or more light sources within the sidewall (e.g., embedded in it) or behind the sidewall;

the sidewall comprising one or more waveguides to which light can be delivered, the sidewall comprising one or more waveguides and one or more light sources that deliver light to such waveguide(s);

the sidewall being light-transporting and comprising one or more waveguides (to which light can be delivered) within the sidewall or behind the sidewall;

the sidewall being light-transporting, the sidewall comprising one or more waveguides within the sidewall or behind the sidewall, and the sidewall comprising one or more light sources that deliver light to the one or more waveguides, etc.

Representative examples of suitable sidewalls that have one or more light exit surface (or sidewall elements making up such sidewalls, or components in such sidewalls) include:

waveguides (to which light is delivered), optionally with one or more translucent films, translucent coatings and/or paint compositions applied to any portion or portions thereof;

any suitable transparent or translucent material or materials (i.e., a material or materials that permits/permit at least some incident light to pass through, e.g., transparent acrylic, a diffuser sheet, frosted glass or acrylic, painted/coated glass or acrylic, and laminates) through which light is delivered;

a coating (in some cases a white coating) or a film (in some cases a white film), so that light exiting from the sidewall is distributed more evenly and so that, from outside the light fixture, the light that exits from the sidewall looks like "reflected" light from the sun (rather than light from an artificial light source);

a light-emitting panel (e.g., an OLED panel);

any suitable light sources or light sources; and any combinations thereof (e.g., a combination of a waveguide and a light source that delivers light to the waveguide; a combination of an acrylic sheet, a white coating on the acrylic sheet and a light source behind the acrylic sheet; etc.).

Light that exits from a light exit surface of a sidewall can have any suitable characteristics. In some embodiments in accordance with the present inventive subject matter, including some embodiments that include or do not include any of the features described herein, light that exits from a light exit surface of a sidewall has one or more characteristics that are described herein for the light that exits from the second light engine (including characteristics such as its color point as well as how it can be adjusted).

There are many ways that a sidewall can be configured such that it is reflective in at least part of its surface. Such reflectivity can be diffuse, specular or any combination thereof. The expression "specular" is used in accordance with its well known meaning to refer to mirror-like reflectivity, whereas "diffuse" (in the context of reflectivity) is used to refer to non-mirror-like reflectivity. Persons of skill in the art are familiar with a wide variety of reflective materials, laminates, coatings, etc., e.g., MCPET (i.e., foamed sheets made of extra-fine, foamed polyethylene terephthalate (PET) available from Furukawa Electric in Japan), and so a detailed discussion of the various reflective materials that can be employed is not necessary. In some embodiments in accordance with the present inventive subject matter, including some embodiments that include or do not include any of the features described herein, the first sidewall, or at least a portion of the first sidewall, can comprise plasterboard or drywall (e.g., Sheetrock).

A sidewall can affect the far-field illumination pattern from the first and/or second light engines in a way that helps create the illusion of light originating from elsewhere (i.e., from the outside sky and sun).

The light sources employed in light fixtures in accordance with the present inventive subject matter (e.g., for a first light engine, a second light engine, or a sidewall in a light fixture in accordance with the first aspect of the present inventive subject matter (including the first group of embodiments, discussed above, and the second and third groups of embodiment, discussed below) or the second aspect of the present inventive subject matter (discussed below), or for generating light in accordance with the third aspect of the present inventive subject matter) can comprise any suitable light source (or light sources). Persons of skill in the art are familiar with, and have ready access to, a wide variety of light sources that emit light in different respective colors, and any suitable light sources can be employed. In any light fixtures, that comprise more than one light source, the light sources can be similar or different, or can include some light sources that are similar and some that are not). Representative examples of types of light sources include light emitting diodes (LEDs), (inorganic or organic, including polymer light emitting diodes (PLEDs)), incandescent lights, fluorescent lamps, laser diodes, thin film electroluminescent devices, light emitting polymers (LEPs), halogen lamps, high intensity discharge lamps, electron-stimulated luminescence lamps, etc.

Although the invention could be made using any of these light sources, or a combination of these light sources, LEDs are particularly convenient light sources because LEDs are (a) available in many colors of interest to the invention, (b) compact, (c) energy efficient.

Many of the embodiments are described as comprising LEDs, and much other disclosure below refers to LEDs, but the present inventive subject matter is not limited to any particular type of light source, i.e., as noted above, lighting fixtures in accordance with the present inventive subject matter can comprise any suitable light source (or light sources).

Embodiments in accordance with the present inventive subject matter are described herein in detail in order to provide exact features of representative embodiments that are within the overall scope of the present inventive subject matter. The present inventive subject matter should not be understood to be limited to such detail.

Embodiments in accordance with the present inventive subject matter are also described with reference to cross-sectional (and/or plan view) illustrations that are schematic illustrations of idealized embodiments of the present inventive subject matter. As such, variations from the shapes of the illustrations as a result, for example, of manufacturing techniques and/or tolerances, are to be expected. Thus, embodiments of the present inventive subject matter should not be construed as being limited to the particular shapes of regions illustrated herein but are to include deviations in shapes that result, for example, from manufacturing. For example, a molded region illustrated or described as a rectangle will, typically, have rounded or curved features. Thus, the regions illustrated in the figures are schematic in nature and their shapes are not intended to illustrate the precise shape of a region of a device and are not intended to limit the scope of the present inventive subject matter.

FIGS. 7, 8, 11-16 and 21-23 schematically depict various embodiments within the scope of the first aspect of the present inventive subject matter. In each of these embodiments, the light fixture is depicted (cross-sectionally) mounted in a ceiling, such that the mean distribution of light exiting the light fixture is generally downward, and the descriptions of spatial relationships is described herein in reference to such orientation (e.g., with terms such as "bottom," "upper," "below," "above," etc.). The light fixtures depicted in FIGS. 7, 8, 11-16 and 21-23 (like all the light fixtures in accordance with the present inventive subject matter) can be mounted in any orientation (and in any suitable structure), e.g., in a vertical wall, in a floor, in a slanted structure, etc., and spatial relationships in such situations would be altered accordingly (e.g., a first structure that is below a second structure if the light fixture is mounted in a ceiling with the mean distribution of light exiting the light fixture generally downward would instead be above the second structure if the light fixture were mounted in a floor with the mean distribution of light exiting the light fixture generally upward).

In addition, in each of the embodiments depicted in FIGS. 7, 8, 11-16 and 21-23, light rays are depicted. The depictions of light rays are not intended to be specific, and are instead intended merely to indicate that light is exiting from respective light engines, and that it travels into the room schematically depicted below each of the light fixtures. Characteristics of light distribution with respect to some specific embodiments are described textually in more detail herein.

The expression "group of embodiments," as used herein, refers to any and all embodiments that have the combination elements and/or features specified. For example, the "first group of embodiments within the first aspect of the present inventive subject matter" refers to embodiments that are light fixtures (artificial skylights), that comprise at least first and second light engines and a first sidewall, in which:

at least a portion of the first light engine resembles a sky (e.g., a surface of the first light engine looks like the sky to a viewer), light exiting from the second light engine has one or more characteristics that resemble that (or those) of at least a portion of light emitted by (and received from) the sun, the first light engine comprises at least a first light exit surface, the first sidewall defines a space, at least a first light exit region is at a boundary of the space, the first light engine is positioned and oriented such that at least some light that exits the first light exit surface passes through at least part of the space and exits the space through the first light exit region, and the second light engine is positioned and oriented such that at least some light that exits the second light engine exits the space through the light exit region.

Similarly, the second group of embodiments within the first aspect of the present inventive subject matter, the third group of embodiments within the first aspect of the present inventive subject matter, etc., encompass any and all embodiments that have the respective combination of features specified.

As discussed above, a first group of embodiments within the first aspect of the present inventive subject matter includes light fixtures that comprise at least first and second light engines and a first sidewall, in which the first sidewall defines a space. FIGS. 7, 8 and 11-15 schematically depict various embodiments within the scope of the first group within the first aspect of the present inventive subject matter.

Referring to FIG. 7, there is shown a light fixture 70 that comprises a first light engine 71, a second light engine 72 and a first sidewall 73 that defines a space (in the form of the recessed box, i.e., a horizontal plane through the first sidewall 73 would intersect the sidewall 73 in a hollow square pattern). The light fixture 70 is mounted in a ceiling 74 which adjoins a wall 75. A beam of light 76 exits from the second light engine 72.

The first light engine 71 comprises an edge-lit panel (or a direct-lit panel), and the second light engine 72 comprises a downlight. The first sidewall 73 comprises at least a first sidewall aperture 77. The second light engine 72 is positioned and oriented such that at least a portion of it extends through the first sidewall aperture 77 and/or light that exits the second light engine 72 passes through the first sidewall aperture 77.

In some embodiments that comprise one or more sidewall apertures, including some embodiments that include or do not include any of the features described herein, one or more screen structure(s) is/are provided to block from view at least part of the second light engine(s). Such screen structure(s), if provided, can be of any suitable material and can be of any suitable size and shape. In embodiments that comprise one or more screen structure(s), the screen structure(s) can cover as much of the second light engine(s) as desired, and/or the screen structure(s) can partially or completely cover the sidewall aperture(s).

FIG. 8 depicts a light fixture 80 that is similar to the light fixture 70 depicted in FIG. 7, except that the light fixture 80 also comprises a screen 88 that covers a sidewall aperture 87, and the light fixture 80 comprises a second light engine 82 that is behind the screen 88, i.e., no portion of the second light engine 82 extends through the sidewall aperture 87. Thus, the light fixture 80 comprises a first light engine 81, the second light engine 82 and a first sidewall 83 that defines a space in the form of the recessed box. The light fixture 80 is mounted in a ceiling 84 which adjoins a wall 85. A beam of light 86 exits from the second light engine 82. The first light engine 81 comprises an edge-lit panel (or a direct-lit panel or a side-lit panel), and the second light engine 82 comprises a downlight. The first sidewall 83 comprises the sidewall aperture 87. The second light engine 82 is positioned and oriented such that at least some light that exits the second light engine 82 passes through the first sidewall aperture 87 and through the screen 88.

In embodiments in which one or more screen structure(s) is/are provided, the screen structure can have any suitable properties. In some embodiments in which one or more screen structure(s) is/are provided, the screen structure allows passage of a large percentage of light within a first wavelength range and allows passage of a much lower percentage of light within a second wavelength range, e.g., the screen structure filters very little of the light that exits the second light engine and it filters a high percentage of light of other wavelengths. In some embodiments, a screen structure can be provided which reduces glare of light that exits from the second light engine.

The bottom surface of the first light engine 71 can be any desired distance above the ceiling 74 (e.g., about six to about ten inches above the ceiling 74—in respective exemplary embodiments corresponding to this embodiment, the bottom surface of the first light engine 71 can be about six inches above the ceiling 74, the bottom surface of the first light engine 71 can be about ten inches above the ceiling 74, or the bottom surface of the first light engine 71 can be any distance between about six inches and about ten inches above the ceiling 74).

The beam of light 76 that exits from the second light engine 72 provides a sharp shadow and illuminates a portion of the wall 75 (providing an effect in the nature of a wall wash).

The overall visual impression created by some embodiments in accordance with the present inventive subject matter, e.g., the embodiment depicted in FIG. 7 (and other embodiments herein) is similar to the visual impression created by light delivered from a conventional skylight on a sunny day. FIG. 9A schematically depicts the visual impression created by a conventional skylight, and FIGS. 9B and 9C depict the visual impression created by representative embodiments of light fixtures in accordance with the present inventive subject matter (e.g., the embodiment depicted in FIG. 7), from a location below and to the side of the light fixture (FIG. 9B) and from a location below the light fixture (FIG. 9C). Additional similarities between [1] the visual impression created by light delivered from some embodiments of light fixtures in accordance with the present inventive subject matter and [2] the visual impression created by light delivered from conventional skylights can include:

light from the second light engine delivers yellow-ish white light and/or shadows (on a nearby wall or walls) in a way that is similar to yellowish-white light and/or shadows (on a nearby wall or walls) delivered from the sun in a conventional skylight;

a bottom surface of the light fixture (e.g., the bottom of the first light engine 71 in the embodiment depicted in FIG. 7) when viewed directly appears uniform, blue-ish white, similar to a view if looking at the sky through a conventional skylight;

overall (i.e., average) color of light delivered to the room from the light fixture is less yellow and more white in comparison the light delivered to a nearby wall (or walls), similar to the light delivered from a mixture of light from the sun and the sky through a conventional skylight.

FIG. 10 depicts a room in which three light fixtures 100 (each similar to the light fixture 70 depicted in FIG. 7) are mounted in a ceiling 104, providing illumination in a work space and also on a wall 105. The illuminance on table tops in the work space is about 600 lux, and the illuminance on the brightly-lit parts of the wall is about 2700 lux.

FIG. 11 depicts a light fixture 110 that comprises a first light engine 111, a second light engine 112 and a first sidewall 113 that defines a space (in the form of the recessed box). The light fixture 110 is mounted in a ceiling 114 which adjoins a wall 115. The first light engine 111 comprises a troffer, and the second light engine 112 comprises a downlight. In this embodiment, the first light engine 111 is configured to deliver sky blue light.

The troffer 111 comprises at least a first troffer aperture 117. The second light engine 112 is positioned and oriented such that at least a portion of it extends through the first troffer aperture 117 and/or light that exits the second light engine 112 passes through the first troffer aperture 117.

In some embodiments that comprise one or more troffer apertures, including some embodiments that include or do not include any of the features described herein, one or more screen structure(s) is/are provided to block from view at least part of the second light engine(s). The description of screen structures above in connection with FIG. 7 is applicable to screen structures that can be employed with regard to troffer apertures, e.g., in the embodiment depicted in FIG. 11.

FIG. 12 depicts a light fixture 120 that comprises a first light engine 121, a second light engine 122 and a first sidewall 123 that defines a space (in the form of the recessed box). The light fixture 120 is mounted in a ceiling 124 which adjoins a wall 125. The first light engine 121 comprises an edge-lit panel or a direct-lit panel, and the second light engine 121 comprises a downlight, and is mounted within the space defined by the first sidewall 123. In this embodiment, the first light engine 121 is configured to deliver sky blue light.

FIG. 13 depicts a light fixture 130 that comprises a first light engine 131, a second light engine 132, a first sidewall 133 that defines a space (in the form of the recessed box), and a diffuser 138. The light fixture 130 is mounted in a ceiling 134 which adjoins a wall 135.

The first light engine 131 comprises an edge-lit panel (or a direct-lit panel), and the second light engine 132 comprises a downlight.

The first sidewall 133 comprises at least a first sidewall aperture 137. The second light engine 132 is positioned and oriented such that at least a portion of it extends through the first sidewall aperture 137 and/or light that exits the second light engine 132 passes through the first sidewall aperture 137. The light fixture 130 is similar to the light fixture 70 depicted in FIG. 7, except that the light fixture 130 comprises a diffuser 138. In some embodiments, the diffuser reduces glare and softens shadows by expanding the distribution of light from the second light engine 132.

In FIG. 13, the diffuser 138 is depicted as being oriented substantially flush with the bottom edge of the first sidewall 133, as having top and bottom substantially flat surfaces, and as being oriented substantially horizontally. The diffuser 138 can instead be mounted in any other suitable orientation, and can be of any other suitable shape (e.g., it can be recessed from the ceiling, i.e., raised somewhat relative to the sidewall). Persons of skill in the art are familiar with a wide variety of diffusers, and any such diffusers can be used in light fixtures in accordance with the present inventive subject matter.

One or more diffusers can be added to any of the embodiments depicted in FIGS. 8, 11 and 12, in a manner similar to the manner in which the diffuser 138 is added to the embodiment depicted in FIG. 7, or in any manner as described above in connection with FIG. 13.

FIG. 14 depicts a light fixture 140 that comprises a first light engine 141, a second light engine 142 and a first sidewall 143 that defines a space (in the form of the recessed box). The light fixture 140 is mounted in a ceiling 144. The first light engine 141 comprises a first edge-lit panel (or a direct-lit panel), and the second light engine 142 comprises a second edge-lit panel with its back reflector removed. In this embodiment, the first light engine 141 is configured to deliver sky blue light. The second light engine 142 is configured to deliver sun-like yellow-ish white light.

In some embodiments in accordance with the present inventive subject matter (including the embodiment depicted in FIG. 14), the far-field light distribution characteristics of the first and second light engines are different from each other. In a representative example of a preferred embodiment, light exiting at high angles (i.e., relative to vertical in FIG. 14) is more yellow-ish white compared to the light directly below the fixture, which is more blue-ish white. In some embodiments, providing a far-field light distribution for the first light engine that differs from a far-field light distribution for the second light engine can be achieved by having different light extraction elements in the first and second light engines, and skilled practitioners are familiar with ways to achieve such differing far-field light distribution (including with different light extraction elements), all of such ways to achieve differing far-field light distribution being included in the present disclosure.

FIG. 15 depicts a light fixture 150 that comprises a first light engine 151, a second light engine 152 and a first sidewall 153 that defines a space (in the form of the recessed box). The light fixture 150 is mounted in a ceiling 154. The first light engine 151 comprises a first edge-lit panel, and the second light engine 152 comprises a second edge-lit panel (or a direct-lit panel). In this embodiment, the first light engine 151 is configured to deliver sky blue light, and has its back reflector removed. Thus, the light fixture 150 is analogous to the light fixture 140, except that in the light fixture 150, the first light engine and the second light engine are switched (i.e., in the light fixture 150, the first light engine is below the second light engine, whereas in the light fixture 140, the second light engine is below the first light engine).

One or more diffusers can be added to either of the embodiments depicted in FIGS. 14 and 15, in a manner similar to the manner in which the diffuser 138 is added to the embodiment depicted in FIG. 7, or in any manner as described above in connection with FIG. 13.

Each of the embodiments depicted in FIGS. 7, 8 and 11-15 comprises a sidewall that does not comprise any light exit surfaces. Any of the sidewalls (and any portion or portions thereof) in any of the light fixtures depicted in FIGS. 7, 8 and 11-15, like the sidewalls in any light fixture disclosed herein that comprises one or more sidewalls, can comprise one or more light exit surfaces, i.e., the sidewall (or one or more of the sidewalls) can be part of a light engine (or parts of light engines), within which light is emitted and such light (or at least part of such light) exits through the light exit surface(s).

In some of the first group of embodiments of light fixtures in accordance with the first aspect of the present inventive subject matter:

light exiting the first light engine has a first peak intensity angle relative to a first plane defined by at least three points on the first light exit region, light exiting the second light engine has a second peak intensity angle relative to the first plane; and the first peak intensity angle differs from the second peak intensity angle.

As discussed above, a second group of embodiments within the first aspect of the present inventive subject matter includes light fixtures that comprise at least a first light engine and a first sidewall, in which:

the first light engine comprises at least a first light exit surface;

the first sidewall comprises at least a second light exit surface (i.e., the first sidewall has one or more light exit surfaces);

the first sidewall defines a space;

at least a first light exit region is at a boundary of the space;

the first light engine is positioned and oriented such that at least some light that exits the first light exit surface passes through at least part of the space and exits the space through the first light exit region; and the first sidewall is positioned and oriented such that at least some light that exits the second light exit surface exits the space through the light exit region.

As noted above, the first sidewall comprises at least a second light exit surface. That is, the first sidewall has one or more surfaces through which light exits, e.g., the first sidewall can be part of a light engine within which light is emitted, and such emitted light (or at least part of such emitted light) exits through the light exit surface(s) into the space, and/or the first sidewall can comprise a light-transporting structure (or part of a light-transporting structure) from which light exits into the space, and/or the first sidewall can comprise a light-transmitting structure (or part of a light-transmitting structure) from which light exits into the space. In some preferred embodiments in accordance with the present inventive subject matter, including some embodiments that include or do not include any of the features described herein, the visible surface of the first sidewall has a matte appearance, similar to frosted glass or a matte white-painted surface.

FIG. 16 schematically depicts an embodiment within the scope of the second group within the first aspect of the present inventive subject matter.

FIG. 16 depicts a light fixture 160 that comprises a first light engine 161 and a second light engine in the form of a first sidewall 162 which comprises four light exit surfaces that define an internal space. The light fixture 160 is mounted in a ceiling 164.

The first sidewall 162 is in the form of the recessed box comprising four surfaces, each of which is, in its entirety, a light exit surface.

The first light engine 161 comprises an edge-lit panel (or a direct-lit panel). The first light engine 161 is configured to deliver sky blue light, and the second light engine is configured to deliver light that has one or more characteristics that resemble that (or those) of at least a portion of light emitted by (and received from) the sun.

In representative embodiments that correspond to FIG. 16, the first sidewall 162 can comprise (or be part of) a light engine that comprises one or more light emitters, and light emitted by such light emitter(s) exit through the first sidewall 162 into the space, and/or the first sidewall can comprise a light-transporting structure (or part of a light-transporting structure) from which light exits into the space, and/or the first sidewall can comprise a light-transmitting structure (or part of a light-transmitting structure) from which light exits into the space.

One or more diffusers can be added to any of the embodiments depicted in FIG. 16 (or in any other embodiment in accordance with the second group within the first aspect of the present inventive subject matter), in a manner similar to the manner in which the diffuser 138 in FIG. 13 is added to the embodiment depicted in FIG. 7, or in any manner as described above in connection with FIG. 13.

In the embodiment depicted in FIG. 16, the far-field light distribution characteristics of the first and second light engines are different from each other. In a preferred embodiment corresponding to FIG. 16, the light exiting at high angles (i.e., relative to vertical in the orientation depicted) from the fixture 160, which is mostly light from the second light engine(s) by virtue of geometry, is more yellow-ish white, whereas the light exiting nearer vertical (in the orientation depicted), which is mostly light from the first light engine(s) by virtue of geometry, is more blue-ish white. In addition to the main geometric effects, the light distribution from one or both light engines can be engineered by having different light extraction elements in the first and/or second light engines, and skilled practitioners are familiar with ways to achieve such differing far-field light distribution (including with different light extraction elements), all of such ways to achieve differing far-field light distribution being included in the present disclosure.

In some of the second group of embodiments of light fixtures in accordance with the first aspect of the present inventive subject matter:

light exiting the first light engine has a first peak intensity angle relative to a first plane defined by at least three points on the first light exit region, light exiting the at least a first sidewall has a second peak intensity angle relative to the first plane; and the first peak intensity angle differs from the second peak intensity angle.

In the embodiment depicted in FIG. 16, the first sidewall 162, which comprises four light exit surfaces, can provide to the light fixture the following advantageous properties:

the first sidewall 162 has substantially uniform luminance (i.e., there is no obviously artificial light source, e.g., there are no hot spots or patterns of light);

the first sidewall 162 appears as if it is illuminated from afar, rather than comprising an artificial light source (i.e., the first sidewall 162 appears as if sunlight were incident on it from outside a skylight); and light exiting from the first sidewall 162 has a color that is distinctly different from the color of light exiting from the first light engine (which resembles the sky).

In some preferred embodiments, for each surface of the first sidewall, the ratio of the maximum luminance to the minimum luminance is 2.5:1 or less (for example, for each surface of the sidewall, if such surface is conceptually divided into 1000 regions of equal size, the largest luminance in any of such regions is not more than two and a half times the luminance in any other of such regions), and/or the ratio of the maximum luminance of each surface of the first sidewall to the average luminance (averaged across the surface) is 2:1 or less.

In some preferred embodiments, one or more of the four surfaces of the first sidewall may emit little or even no light directly (i.e. only light reflected from elsewhere) to enhance the visual illusion that the first sidewall is being illuminated obliquely by the sun (i.e. one or more of the surfaces appears to be in the shade while the remainder are illuminated.)

FIG. 17 schematically depicts a cross-sectional view of a portion of a sidewall 170 that comprises a first translucent element 171, a light source 172 within the first translucent element 171, and an opaque reflective back panel 173. Emitted light 174 exits from the sidewall 170 (in the embodiment depicted in FIG. 17, the emitted light 174 exits from a side of the sidewall 170 opposite to the side on which the reflective back panel 173 is provided.

FIG. 18 schematically depicts a cross-sectional view of a portion of a sidewall 180 that comprises a first translucent element 181, a light source 182 behind the first translucent element 181, an opaque reflective back wall 183a and opaque reflective side walls 183b, such that light 184 that exits from the light source 182 passes through the first translucent element 181 (and in the embodiment depicted in FIG. 18, light 184 exits from a side of the sidewall 180 that is opposite the opaque reflective back wall 183a).

FIG. 19 schematically depicts a cross-sectional view of a portion of a sidewall 190 that comprises a first waveguide 191, a light source 192 that delivers light to the first waveguide 191, and an opaque reflective back panel 193, such that light 194 exits from the sidewall 190 (and in the embodiment depicted in FIG. 19, light 194 exits from a side of the sidewall 190 that is opposite the opaque reflective back panel 193).

FIG. 20 schematically depicts a cross-sectional view of a portion of a (side-lit direct lit) sidewall 200 that comprises a first translucent element 201, a light source 202 adjacent to the translucent element 201, an opaque reflective back wall 203a, and opaque reflective side walls 203b, such that light 204 exits from the sidewall 200 (and in the embodiment depicted in FIG. 20, light 204 exits from a side of the sidewall 200 that is opposite the opaque reflective back wall 203a).

In FIGS. 17-20, while a single light source is depicted, multiple light sources may be employed.

As discussed above, a third group of embodiments within the first aspect of the present inventive subject matter includes light fixtures that comprise at least a first and second light engines, in which:

the first light engine comprises at least a first light exit surface;

the first and second light engines are positioned and oriented such that at least some light that exits the first light exit surface travels to a region (e.g., in an office or a room) to which at least some light that exits the second light engine travels.

FIGS. 21-23 schematically depict embodiments within the scope of the third group within the first aspect of the present inventive subject matter.

FIG. 21 depicts a light fixture 210 that comprises a first light engine 211 and a second light engine 212. The light fixture 210 is similar to the light fixture 140 depicted in FIG. 14, except that in the light fixture 140, the lower surface of the second light engine 142 is recessed relative to the ceiling 144, whereas in the light fixture 210 depicted in FIG. 21, the lower surface of the second light engine 212 is substantially flush with the ceiling 214.

In some embodiments in which a surface of a second light engine is substantially flush with a ceiling (or other structure), the far-field light distribution characteristics of the first and second light engines are different from each other. The differing far-field light distribution characteristics of such embodiments are particularly important in such embodiments, because otherwise the combination of blue-ish and yellow-ish light would simply be white and no different from a conventional panel light. In a preferred embodiment in accordance with the present inventive subject matter, light exiting at high angles (i.e., relative to an axis of the light fixture, e.g., relative to vertical from the fixture 210 as depicted in FIG. 21) is mostly light from the second light engine(s) and is more yellow-ish white, whereas the light exiting nearer vertical (as depicted in FIG. 21) is mostly light from the first light engine and is more blue-ish white. In some embodiments, light distribution from one or both light engines can be engineered by having different light extraction elements in the first and/or second light engines, and skilled practitioners are familiar with ways to achieve such differing far-field light distribution (including with different light extraction elements), all of such ways to achieve differing far-field light distribution being included in the present disclosure.

Another embodiment is similar to the embodiment depicted in FIG. 21, except that the first light engine 211 and the second light engine 212 are switched (and the back reflector is removed from the first light engine 211 instead of the second light engine 212.

FIG. 22 depicts a light fixture 220 that comprises a first light engine 221 and a second light engine 222. The light fixture 220 is similar to the light fixture 210 depicted in FIG. 21, except that in the light fixture 210 depicted in FIG. 21, the lower surface of the second light engine 212 is substantially flush with the ceiling 214, whereas in the light fixture 220 depicted in FIG. 22, the first light engine 221 and the second light engine 222 are mounted on the surface of the ceiling 224.

In some embodiments in which a first light engine and a second light engine are mounted on a surface of a ceiling (or other structure), the far-field light distribution characteristics of the first and second light engines are different from each other. The differing far-field light distribution characteristics of such embodiments is particularly important in such embodiments, because otherwise the combination of blue-ish and yellow-ish light would simply be white and no different from a conventional panel light. In a preferred embodiment in accordance with the present inventive subject matter, light exiting at high angles (i.e., relative to an axis of the light fixture, e.g., relative to vertical from the fixture 220 as depicted in FIG. 22) is mostly light from the second light engine(s) and is more yellow-ish white, whereas the light exiting nearer vertical (as depicted in FIG. 22) is mostly light from the first light engine and is more blue-ish white. In some embodiments, light distribution from one or both light engines can be engineered by having different light extraction elements in the first and/or second light engines, and skilled practitioners are familiar with ways to achieve such differing far-field light distribution (including with different light extraction elements), all of such ways to achieve differing far-field light distribution being included in the present disclosure.

Another embodiment is similar to the embodiment depicted in FIG. 22, except that the first light engine 221 and the second light engine 222 are switched (and the back reflector is removed from the first light engine 221 instead of the second light engine 222.

FIG. 23 depicts a light fixture 230 that comprises a first light engine 231, a second light engine 232 and a bracket 237 that holds the second light engine 232 in place relative to the first light engine 231. The bracket 237 (or a bracket in any other embodiment within the scope of the present inventive subject matter) can be of any suitable size, shape and material, and persons of ordinary skill in the art can readily select suitable materials, sizes and shapes for such brackets.

An embodiment as depicted in FIG. 23 can, e.g., be used in an existing sidewall (or in combination with a sidewall that can be installed, or a sidewall that has been installed), to provide any one or more of the features as described herein.

One or more diffusers can be added to any of the embodiments depicted in FIGS. 21-23 (or in any other embodiment in accordance with the third group within the first aspect of the present inventive subject matter), in a manner similar to the manner in which the diffuser 138 in FIG. 13 is added to the embodiment depicted in FIG. 7, or in any manner as described above in connection with FIG. 13.

In some embodiments in accordance with the present inventive subject matter, including some embodiments that include or do not include any of the features described herein, the far-field distribution of light that exits the first light engine differs from the far-field distribution of light that exits from a second light engine and/or light that exits from a sidewall (including any first light engines, second light engines and/or sidewalls described herein).

In one aspect of the respective far-field distributions of light, the distribution of light that exits from the first light engine is closer to perpendicular to a plane defined by a light exit region from the space defined by the sidewall than the distribution of light that exits from the second light engine (e.g., in each of the embodiments depicted in FIGS. 7 and 11-15, the distribution of light that exits from the first light engine is closer to vertical than the distribution of light that exits from the second light engine).

Representative examples where light that exits from a first light engine is closer to a particular direction than light that exits from a second light engine include:

[1] where 60% of light that exits from a first light engine defines an angle between 0 degrees and 45 degrees relative to such direction and 40% of light that exits from the first light engine defines an angle between 45 degrees and 90 degrees relative to such direction, and 30% of light that exits from a second light engine defines an angle between 0 degrees and 45 degrees relative to such direction and 70% of light that exits from the second light engine defines an angle between 45 degrees and 90 degrees relative to such direction, or

[2] where 30% of light that exits from a first light engine defines an angle between 0 degrees and 25 degrees relative to such direction and 65% of light that exits from the first light engine defines an angle between 25 degrees and 90 degrees relative to such direction, and 20% of light that exits from a second light engine defines an angle between 0 degrees and 25 degrees relative to such direction and 80% of light that exits from the second light engine defines an angle between 25 degrees and 90 degrees relative to such direction, etc.

In some embodiments, a distribution of light that exits from a second light engine having a larger angle relative to perpendicular to a light exit region than light that exits from a first light engine contributes to an illusion of comparatively bright sunlight being reflected and the sky being visible and not as bright.

In another aspect of the respective far-field distributions of light, the distribution of light that exits from the first light engine is closer to perpendicular to a plane defined by a light exit region from the space defined by the sidewall than the distribution of light that exits from the sidewall (e.g., in the embodiment depicted in FIG. 16, the distribution of light that exits from the first light engine is closer to vertical than the distribution of light that exits from the sidewall).

In the above discussion, the distribution of light is described in relation to perpendicular to a plane defined by a light exit region from the space defined by the sidewall. In some embodiments, the distribution of light would be described in relation to perpendicular to a plane defined by a largest periphery of the light fixture, or in relation to an axis of rotational symmetry, or in relation to the intersection of two planes of symmetry, or in relation to perpendicular to a plane defined by a light exit surface of the first light engine, or in relation to perpendicular to a plane that is tangential to a curved or dome-shaped light exit surface of the first light engine, or in relation to a plane defined by a surface in which the light fixture is mounted, e.g., a ceiling, a wall, a floor, a slanted structure, etc.

In another aspect of the respective far-field distributions of light, the distribution of light that exits from the first light engine is closer to perpendicular to a plane defined by a light exit surface of the first light engine (or a plane that is tangential to a curved or dome-shaped light exit surface of the first light engine) than the distribution of light that exits from the second light engine (e.g., in each of the embodiments depicted in FIGS. 21-23, the distribution of light that exits from the first light engine is closer to vertical than the distribution of light that exits from the second light engine).

In some of the third group of embodiments of light fixtures in accordance with the first aspect of the present inventive subject matter:

light exiting the first light engine has a first peak intensity angle relative to a first plane defined by at least three points on the first light exit surface, light exiting the second light engine has a second peak intensity angle relative to the first plane; and the first peak intensity angle differs from the second peak intensity angle.

In some embodiments of light fixtures and/or methods in accordance with the present inventive subject matter, including some embodiments that include or do not include any of the features described herein, there is at least some variation in light color among light exiting a light fixture, e.g., the color point of light traveling at a first angle relative to the axis of light distribution differs from the color point of light traveling at a second angle relative to the axis of light distribution. Such differences in color point can be relatively small or relatively large, e.g., a 10-step MacAdam ellipse, a 20-step MacAdam ellipse, at least 0.05 units on a 1931 CIE Chromaticity Diagram, at least 0.10 (or 0.15, 0.20. 0.25. 0.30. 0.35, 0.40, 0.45 or 0.50) units on a 1931 CIE Chromaticity Diagram.

In some of such embodiments (i.e., embodiments in which there is at least some variation in light color among light exiting a light fixture), at least a portion of such color point variance results from different far-field distribution contributions from a first light engine (resembling the sky) and from a second light engine (resembling the sun). The present specification includes a number of descriptions relating to light fixtures and methods in which the far-field light distribution characteristics of first and second light engines are different from each other.

For conventional lights, color variation over angle (i.e., lighting in which there is a significant difference in the color point of light traveling at different angles relative to an axis of light distribution differs from the color point of light traveling at a second angle relative to the axis of light distribution) is generally not a desirable feature. However, color variation is an important element of natural skylights and therefore is desirable for creating or enhancing the illusion of an artificial skylight. Due to (1) the basic geometry of typical skylights (i.e. a recessed box in ceiling with central window), (2) the sun being visible only at specific angles depending on time of day, and (3) the sky being visible over a relatively large range of angles, the light delivered into a space from a skylight will typically have regions of high CCT (i.e. bluish white) and regions of low CCT (i.e. yellowish light). Some embodiments of the present invention provide this feature.

FIG. 24A shows a plot of CCT over viewing angle measured using a light fixture similar to FIG. 16 and a gonio-spectrophotometer arrangement where the detector is located about 6.5 feet away from the fixture. At an angle of zero degrees, which corresponds to directly below the fixture if it were in a ceiling, the CCT is approximately 6500K. The CCT decreases to about 4700K at a viewing angle of 75 degrees. Broadly speaking such characteristics are similar to light from a natural skylight when the sun is low in the sky. These CCT values and ranges are representative—the present inventive subject matter is not limited to these CCT values and ranges, and persons of skill in the art will recognize that the present inventive subject matter encompasses other CCT ranges, and a variety of CCT ranges can be employed and are desirable.

Another feature of natural daylight is that it generally provides very high quality light having a color rendering index (CRI) of approximately 100. This is because daylight is typically full spectrum light (and also reflects the definition of CRI). Moreover, very high CRI is maintained regardless of the CCT. Thus, a desirable feature of an artificial skylight is that it delivers light having high CRI.

FIG. 24B shows a plot of the measured CRI over viewing angle measured using the same set-up as described above. The delivered light has high CRI (about 85) at all viewing angles, irrespective of the CCT. As a result, the quality of light as perceived in the space being lit is high, which adds to the illusion of a skylight. In some embodiments in accordance with the present inventive subject matter, the CRI of the light delivered by the light fixtures is at least 80 at all angles (and in some of those embodiments, the CRI of the light delivered by the light fixtures is at least 85). Alternative color quality metrics to CRI can also be used (e.g. those described in TM30-15.)

Persons of skill in the art are familiar with ways to achieve high CRI values, and selecting suitable components (e.g., LED components) to achieve high CRI values is straightforward, and therefore discussion of the many ways to achieve such high CRI values is not necessary.

As noted above, in a second aspect, the present inventive subject matter relates to light fixtures that comprise first and second light engines, in which the second light engine comprises at least a first sidewall from which light exits.

In some embodiments in accordance with the second aspect, the at least a first sidewall defines a space, the first light engine delivers light to the space, and at least a first light exit region is at a boundary of the space.

In some embodiments of light fixtures in accordance with the second aspect of the present inventive subject matter, including some embodiments that include or do not include any of the features described herein, the first light engine comprises a light exit surface that defines a first plane, the light exit region defines a second plane, the first plane and the second plane are substantially parallel, and:
    the first plane is spaced from the second plane by at least three inches, and in some embodiments at least four inches, and in some embodiments at least six inches, and/or
    at least one surface of the first sidewall defines a plane that defines an angle of at least 75 degrees (and in some embodiments at least 80 degrees, and in some embodiments at least 85 degrees, and in some embodiments about 90 degrees) relative to the first plane and relative to the second plane.

In some embodiments of light fixtures in accordance with the second aspect of the present inventive subject matter, including some embodiments that include or do not include any of the features described herein, the first light engine comprises a light exit surface, a first plane is tangential to the light exit surface, the light exit region defines a second plane, the first plane and the second plane are substantially parallel, and:
    the first plane is spaced from the second plane by at least three inches, and in some embodiments at least four inches, and in some embodiments at least six inches, and/or
    at least one surface of the first sidewall defines a plane that defines an angle of at least 75 degrees (and in some embodiments at least 80 degrees, and in some embodiments at least 85 degrees, and in some embodiments about 90 degrees) relative to the first plane and relative to the second plane.

In relation to the second aspect of the present inventive subject matter, the respective characteristics of light that exits from the first light engine and light that exits from the second light engine are not limited to the descriptions above of the respective characteristics of light that exits from the first light engine and light that exits from the second light engine. The descriptions above of components and materials that are suitable for making a sidewall that has one or more light exit surfaces in accordance with the first aspect of the present inventive subject matter are applicable to the sidewall that has one or more light exit surfaces in accordance with the second aspect of the present inventive subject matter.

FIG. 25 schematically depicts a representative embodiment in accordance with the second aspect of the present inventive subject matter. FIG. 25 depicts a light fixture 250 that comprises a first light engine 251 and a first sidewall 252 which comprises four light exit surfaces. The light fixture 250 is mounted in a ceiling 254.

The first sidewall 252 is in the form of the recessed box comprising four surfaces, each of which is, in its entirety, a light exit surface.

The first light engine 251 comprises an edge-lit panel (or a direct-lit panel).

One or more diffusers can be added to the embodiment depicted in FIG. 25 (or in any other embodiment in accordance with the second group within the first aspect of the present inventive subject matter), in a manner similar to the manner in which the diffuser 138 in FIG. 13 is added to the embodiment depicted in FIG. 7, or in any manner as described above in connection with FIG. 13.

In some embodiments in accordance with the first aspect or the second aspect of the present inventive subject matter, including some embodiments that include or do not include any of the features described herein, a periphery of the first light engine is substantially similar to a periphery of the sidewall (or at least a portion of a periphery of the first light engine is substantially similar to a periphery of the sidewall, or a portion of a periphery of the sidewall). For example, in some embodiments in accordance with the present inventive subject matter, including some embodiments that include or do not include any of the features described herein, the sidewall is substantially rectangular annular and a periphery of the first light engine is substantially rectangular (e.g., such that the first light engine covers substantially all of the space defined by the annular sidewall, except for a relatively thin peripheral border of the space defined by the annular sidewall); in some embodiments in accordance with the present inventive subject matter, including some embodiments that include or do not include any of the features described herein, the sidewall is substantially circular annular and a periphery of the first light engine is substantially circular.

In some embodiments in accordance with the first aspect or the second aspect of the present inventive subject matter, including some embodiments that include or do not include any of the features described herein, the sidewall defines (and in some cases extends around) the sides of a space, the sidewall has a first edge that defines (and in some cases extends around) a top boundary of the space and the sidewall has a second edge that defines (and in some cases extends around) a bottom boundary of the space (recognizing that top and bottom are relative, and the sidewall could be in any orientation, such that orientations of the "top" and "bottom" would be affected accordingly). In such embodiments, the bottom boundary can be the light exit region (through which light that exits from the first light engine and light that exits from the second light engine passes), and the top boundary can be space in which the first light engine can be accommodated (e.g., the first light engine is partially within the space), and/or through which light that exits the first light engine can enter the space (e.g., the first light engine is partially or completely outside the space), and/or within which the first light engine is positioned (e.g., the first light engine is completely in the space).

As is evident from the discussion above, in some embodiments in accordance with the first aspect or the second aspect of the present inventive subject matter, including some embodiments that include or do not include any of the features described herein, at least some of the dimensions of the first light engine bear a relation to some of the dimensions of the sidewall, and/or the dimensions of the space defined (at least in part) by the sidewall.

In some embodiments of light fixtures in accordance with the first aspect or the second aspect of the present inventive subject matter, including some embodiments that include or do not include any of the features described herein, the first light engine can be positioned relative to the sidewall in any suitable position In some embodiments of light fixtures in accordance with the first aspect or the second aspect of the present inventive subject matter, including some embodiments that include or do not include any of the features described herein, the light fixture can further comprise a back wall, i.e., a structure that partially or completely covers the "top" boundary of the space (and in such embodiments, the first light engine can be partially or completely inside the space).

In some embodiments of light fixtures in accordance with the first aspect or the second aspect of the present inventive subject matter, including some embodiments that include or do not include any of the features described herein, the light fixture can further comprise one or more heat dissipation structures and/or one or more heat transfer structures, e.g., heat fins or heat pins can be provided on the side of a back wall (if included) opposite to the space.

The light exit surface of the first light engine can be recessed by any suitable or desired distance relative to the light exit region and/or the sidewall. For example, a ratio of the distance the first light engine is recessed relative to the overall size of the first light engine or the light fixture is not limited. In addition, as noted below, the light fixtures of the present inventive subject matter are scalable (i.e., the size of the light fixtures, or any portion or portions thereof, can be modified by being magnified or shrunk to any degree—see the definition and discussion of "scalable" below). As representative distances of recess, in some embodiments in accordance with the present inventive subject matter, including some embodiments that include or do not include any of the features described herein, the light exit surface of the first light engine is recessed about one inch to about 40 inches or more (particularly in view of the scalability, the distance of recess can be much larger), in some cases about three inches to about nine inches (e.g., about five inches), for example, the distance between the light exit surface of the first light engine and the light exit region in some embodiments is about three inches to about nine inches, and in some embodiments about five inches, about six inches, about seven inches, about three inches to about five inches, about three inches to about seven inches, or about five inches to about seven inches.

In some embodiments of light fixtures in accordance with the first aspect or the second aspect of the present inventive subject matter, including some embodiments that include or do not include any of the features described herein, the "top" boundary of the space is of a shape and/or size that is substantially similar to a shape of the "bottom" boundary of the space, and/or the "top" boundary of the space is substantially aligned with the "bottom" boundary of the space (e.g., vertical planes that bisect the "top" of the boundary also bisect the "bottom" of the boundary).

In some embodiments in accordance with the first aspect or the second aspect of the present inventive subject matter, including some embodiments that include or do not include any of the features described herein, the light fixture can further comprise at least one baffle element. In such embodiments, the baffle element is positioned and oriented such that it increases collimation of light that exits from the second light engine. In embodiments in which one or more baffle element(s) is/are provided, the baffle element(s) can be of any suitable shape (e.g., in a rectilinear grid pattern, in a substantially cylindrical shape, and/or in a honeycomb shape), and can, if desired, be reflective or light-absorbing (for example, in some instances, a baffle element can be colored (or painted) black, so that off-angle light will be absorbed and only light that is substantially parallel (e.g., aligned with an axis of light distribution) will pass through the baffle element. Additionally, reflectors can be used to limit or cut off spill light. Representative examples of baffle elements are depicted in FIGS. 26 and 27.

FIG. 26 schematically depicts a representative example of a baffle element 260 suitable for use in accordance with the present inventive subject matter.

FIG. 27 schematically depicts a representative example of a baffle element 270 suitable for use in accordance with the present inventive subject matter.

As mentioned above, in a third aspect, the present inventive subject matter relates to light fixtures that output light having specific characteristics. As discussed in more detail below, the third aspect of the present inventive subject matter (i.e., the "third aspect") relates in general to any light fixtures that comprise the features described herein in relation to the third aspect and/or that provide the effects described herein in relation to the third aspect. Some of the light fixtures described herein in relation to the first and second aspects of the present inventive subject matter (as well as the fourth through seventh aspects of the present inventive subject matter, discussed below) comprise such features and/or provide such effects, but the third aspect is not limited to only light fixtures in accordance with the first and second aspects (or the fourth through seventh aspects). That is, the scope of the light fixtures in accordance with the third aspect is not limited to any of the features of the first and second aspects of the present inventive subject matter (or the fourth through seventh aspects of the present inventive subject matter).

Light fixtures in accordance with the third aspect of the present inventive subject matter are capable of providing light output that can achieve specific biological effects, such as adjusting a person's biological melatonin levels in a desired way (e.g., during twenty-four-hour periods), for instance to adjust a person's circadian rhythm, to ameliorate a person's circadian rhythm disorders, and/or to adjust a person's alertness (e.g., to increase the person's alertness during some daily time periods and/or to increase the person's drowsiness during other daily time periods).

In animals, circulating levels of the hormone melatonin (N-acetyl-5-methoxytryptamine) typically vary in a daily cycle. The melatonin signal forms part of the system that regulates the sleep-wake cycle by chemically causing drowsiness and lowering body temperature.

Lux is a measure of the intensity of illumination as distinguished by the human eye. This value does not correlate to an objective value of energy radiated or reflected, because different wavelengths within the visible spectrum are perceived with varying sensitivity by the eye. Lux is quantified by evaluating light intensity in consideration of this variable.

The apparent sensitivity of the human circadian system differs from the luminosity function used in determining lux.

While not wishing to be bound by any theories, some have correlated relative suppression of melatonin production in humans vs. wavelength of light to which subjects are exposed. One representative example of such a correlation might be that:

light of wavelength of about 410 nm provides a relative melatonin suppression in humans of about 0.35;
light of wavelength of about 425 nm provides a relative melatonin suppression in humans of about 0.7;
light of wavelength in the range of from about 437 to about 462 nm provides a relative melatonin suppression in humans of about 0.95;
light of wavelength of about 475 nm provides a relative melatonin suppression in humans of about 0.8;
light of wavelength of about 500 nm provides a relative melatonin suppression in humans of about 0.4; and
light of wavelength of about 600 nm provides a relative melatonin suppression in humans of about 0.

An example of a plot of relative suppression of melatonin production in humans vs. wavelength of light to which subject are exposed can be found in Rea et al., *Journal of Circadian Rhythms*, 2010, 8:2 (http://www.jcircadianrhythms.com/content/8/1/2) (see FIG. 3).

CS value ("circadian stimulus value") for a light source is a measure of the percentage of melatonin suppression when exposed (i.e., illuminance received at the eye) to the light source (i.e., a CS value of 0.2 correlates to 20% melatonin suppression, a CS value of 0.4 correlates to 40% melatonin suppression, a CS value of 0.6 correlates to 60% melatonin suppression, a CS value of 0.8 correlates to 80% melatonin suppression, etc. CS values are described in M. S. Rea et al, "Modeling the spectral sensitivity of the human circadian system," 2012; see also online link to calculator http://www.lrc.rpi.edu/programs/lightHealth/index.asp.

Circadian rhythm disorders have been associated by some with change in nocturnal activity (e.g., nighttime shift workers), change in longitude (e.g., jet lag), and/or seasonal change in light duration (e.g., seasonal affective disorder, with symptoms including depression). In 2007, the World Health Organization named late-night shift work as a probable cancer-causing agent.

Aspects that relate to melatonin levels and the human circadian cycle are described in U.S. Pat. Nos. 9,030,103, 9,039,746, U.S. Patent Application Publication No. 2015/0195855 and U.S. patent application Publication Ser. No. 14/669,739 (now U.S. Pat. No. 9,681,510), the entireties of which are incorporated herein by reference as if set forth fully herein.

In accordance with the third aspect of the present inventive subject matter, there is provided a light fixture that comprises at least a first light engine and a second light engine, in which:

the first light engine has the ability to output light that provides a first CS value at a given illuminance,
the second light engine has the ability to output light that provides a second CS value at the same illuminance, and
the first CS value is different from the second CS value.

In some embodiments in accordance with the third aspect of the present inventive subject matter, there is provided a light fixture that comprises one or more light engines that output light that provides strong suppression of melatonin (and/or a high CS value) at a given photopic illuminance, as well as one or more light engines that output light that does not (and/or a light fixture that comprises one or more light engines that can be controlled or adjusted to selectively output (1) light that provides strong suppression of melatonin (and/or a high CS value), e.g., at a given photopic illuminance and (2) light that does not provide strong suppression of melatonin), e.g., at said given photopic illuminance. The present inventive subject matter also comprises methods that comprise exposing a subject, e.g., a human, to light output from such light fixtures. In some embodiments in accordance with the third aspect of the present inventive subject matter, controls are provided to adjust the light output by the light fixture to adjust the degree of melatonin suppression provided to a person subjected to the light output by the light fixture (and/or to adjust the CS value provided by such light). For example, light fixtures can have multiple melatonin suppression settings (and/or CS value settings), incremental melatonin suppression settings (and/or CS value settings), or a substantially continuous range of melatonin suppression capabilities (and/or CS value settings). Melatonin suppression (and/or CS value of output light) of such light fixtures can be controlled automatically (e.g., in accordance with a daily cycles or selection of one of a number of selectable daily cycles, in accordance with user input, in response to feedback of a person's biological melatonin levels, in response to one or more sensed conditions, etc.). Control signals can be received by the light fixtures in any suitable way, e.g., wirelessly or through a wired connection. The present inventive subject matter also comprises methods that comprise exposing a subject, e.g., a human, to light output from such light fixtures.

Light fixtures in accordance with the third aspect of the present inventive subject matter can comprise solid state light emitters (e.g., LEDs) or any other light sources, any of which optionally include wavelength conversion material (e.g., phosphors), to provide the capability of outputting light of different color points at different times. Such light fixtures can comprise controls for controlling the light source(s) to output light of different color points at different times (e.g., light fixtures in accordance with the third aspect of the present inventive subject matter can comprise any LED lights where individual and/or groups of LEDs with different colors (e.g., of wavelength converted colored or white LEDs and/or non-wavelength converted LEDs) are controlled to produce different mixtures of the light to provide some or all of the effects described in relation to the third aspect of the present inventive subject matter, e.g., to adjust one or more persons' circadian rhythm, to ameliorate one or more persons' circadian rhythm disorders, to adjust one or more persons' alertness, to provide a particular CS value in a subject or to bring a subject's CS value to above or below a particular CS value, and/or to provide a desired melatonin suppression or to bring melatonin suppression to above or below a particular degree of suppression).

In some embodiments of light fixtures in accordance with the third aspect of the present inventive subject matter, including some embodiments that include or do not include any of the features described herein:
the first light engine is configured to output light of a first color point,
the second light engine is configured to output light of a second color point, and
the first color point is spaced from the second color point.

In some embodiments of light fixtures in accordance with the third aspect of the present inventive subject matter, including some embodiments that include or do not include any of the features described herein, upon supplying electricity to the light fixture:
light that has x, y color coordinates which define a point on a 1931 CIE Chromaticity Diagram which is within a quadrilateral area with vertices having x, y coordinates of (0.37, 0.34), (0.35, 0.38), (0.15, 0.20), and (0.20, 0.14) (and in some embodiments, within a quadrilateral area with vertices having x, y coordinates of (0.32, 0.31), (0.30, 0.33), (0.15, 0.17), and (0.17, 0.14)) exits from the first light engine, and
light that has x, y color coordinates which define a point on a 1931 CIE Chromaticity Diagram which is within an area with vertices having x, y coordinates of (0.29, 0.32), (0.32, 0.29), (0.41, 0.36), (0.48, 0.39), (0.48, 0.43), (0.40, 0.41), and (0.35, 0.38) (and in some embodiments, within an area with vertices having x, y coordinates of (0.30, 0.34), (0.30, 0.30), (0.39, 0.36), (0.45, 0.39), (0.47, 0.43), (0.40, 0.41), and (0.35, 0.38)) exits from the second light engine.

In some embodiments of light fixtures in accordance with the third aspect of the present inventive subject matter, including some embodiments that include or do not include any of the features described herein,
the first light engine has the ability to output light that provides a CS value of at least 0.3 at an illuminance of 300 lux (or more), and
the second light engine has the ability to output light that provides a CS value of less than 0.15 at an illuminance of 200 lux (or less) (and/or the ability to output light that provides a CS value of less than 0.2 at an illuminance of 300 lux).

In some embodiments of light fixtures in accordance with the third aspect of the present inventive subject matter, including some embodiments that include or do not include any of the features described herein, there is provided a light fixture in which:
the light fixture further comprises a first sidewall,
the first sidewall defines a space,
at least a first light exit region is at a boundary of the space,
the first light engine is positioned and oriented such that at least some light that exits the first light engine passes through at least part of the space and exits the space through the first light exit region, and
the second light engine is positioned and oriented such that at least some light that exits the second light engine exits the space through the first light exit region. In some of such embodiments, at least some light that exits from the second light engine exits from the first sidewall.

In some embodiments of light fixtures in accordance with the third aspect of the present inventive subject matter, including some embodiments that include or do not include any of the features described herein:
the second light engine comprises a first sidewall,
the first sidewall defines a space,
at least a first light exit region is at a boundary of the space,
the first light engine is positioned and oriented such that at least some light that exits the first light engine passes through at least part of the space and exits the space through the first light exit region, and
the second light engine is positioned and oriented such that at least some light that exits the second light engine exits the space through the first light exit region.

In some embodiments of light fixtures in accordance with the third aspect of the present inventive subject matter, including some embodiments that include or do not include any of the features described herein:
the light fixture further comprises at least a first control element, and
the at least a first control element controls independently at least a brightness of light exiting from the first light engine and a brightness of light exiting from the second light engine.

In some embodiments of light fixtures in accordance with the third aspect of the present inventive subject matter, including some embodiments that include or do not include any of the features described herein:
the light fixture further comprises at least a first control element, and
the at least a first control element is configured to vary the CS value of light output from the light fixture.

In some embodiments of light fixtures in accordance with the third aspect of the present inventive subject matter, including some embodiments that include or do not include any of the features described herein:

the light fixture further comprises at least a first control element, and the at least a first control element is configured to vary the CS value based on the time of day.

In some embodiments of light fixtures in accordance with the third aspect of the present inventive subject matter, including some embodiments that include or do not include any of the features described herein:

the light fixture further comprises at least a first control element, the first control element is configured to cause the light fixture to output light having a CS value of at least 0.3 at an illuminance of 300 lux during a first part of the day, and the first control element is configured to cause the light fixture to output light having a CS value of less than 0.15 at an illuminance of 200 lux (and/or to cause the light fixture to output light having a CS value of less than 0.2 at an illuminance of 300 lux) during a second part of the day.

In some embodiments of light fixtures in accordance with the third aspect of the present inventive subject matter, including some embodiments that include or do not include any of the features described herein:

the light fixture further comprises at least a first control element, the first control element is configured to vary a ratio of brightness of light output from the first light engine to brightness of light output from the second light engine.

In some of such embodiments:

the at least a first control element causes the ratio of brightness of light output from the first light engine to brightness of light output from the second light engine to be at least a first value during a first part of the day, the at least a first control element causes the ratio of brightness of light output from the first light engine to brightness of light output from the second light engine to be not greater than a second value during a second part of the day, and the first value is greater than the second value.

In some embodiments of light fixtures in accordance with the third aspect of the present inventive subject matter, including some embodiments that include or do not include any of the features described herein, the light fixture is capable of outputting light that provides a CS value of at least 0.3 at a photopic illuminance of 300 lux. In some of such embodiments, the light fixture is also capable of outputting light that provides a CS value of less than 0.15 at a photopic illuminance of 200 lux.

In some embodiments of light fixtures in accordance with the third aspect of the present inventive subject matter, including some embodiments that include or do not include any of the features described herein:

the first light engine has the ability to output light that provides a first suppression of melatonin at a first photopic illuminance, the second light engine has the ability to output light that provides a second suppression of melatonin at said first photopic illuminance, and the first suppression of melatonin differs from the second suppression of melatonin.

In some embodiments of light fixtures in accordance with the third aspect of the present inventive subject matter, including some embodiments that include or do not include any of the features described herein, the light fixtures are capable of outputting light that provides a CS value (in at least some humans) of at least 0.3 during at least a first part of the day, and outputting light that provides a CS value (in at least some humans) of less than 0.15 during at least a second part of the day, the photopic lux output during the second part of the day comprising at least 50% (and in some embodiments at least 60%, 70%, 80% or 90%) of the photopic lux output during the first part of the day.

Some embodiments of light fixtures in accordance with the first aspect or the second aspect of the present inventive subject matter are particularly well suited to being used to affect a person's biological melatonin levels in a desired way. In some of such embodiments, for example, the light fixture (artificial skylight) comprises one or more light engines (e.g., the first light engine, which resembles the sky) that output light that provides strong suppression of melatonin, as well as one or more light engines (e.g., the second light engine, which has one or more characteristics that resemble that (or those) of at least a portion of light emitted by (and received from) the sun) that output light that provides less suppression of melatonin. In other words, a light fixture in accordance with the third aspect of the present inventive subject matter can comprise features described herein in connection with the first and/or the second aspect of the present inventive subject matter. In some of these embodiments, controls are provided to adjust the light output by the light fixture to adjust a predicted degree of melatonin suppression provided to a person subjected to the light output by the light fixture (and/or to provide a specific CS value or a CS value greater than or less than a specific value). For example, light fixtures can have multiple predicted melatonin suppression settings (and/or CS value settings or range settings), incremental predicted melatonin suppression settings (and/or CS value settings or range settings), or a substantially continuous range of predicted melatonin suppression capabilities (and/or CS value settings). Predicted melatonin suppression of such light fixtures (and/or CS values) can be controlled automatically (e.g., in accordance with a daily cycles or selection of one of a number of selectable daily cycles, in accordance with user input, in response to feedback of a person's biological melatonin levels, in response to one or more sensed conditions, etc.). Control signals can be received by the light fixtures in any suitable way, e.g., wirelessly or through a wired connection.

In accordance with a fourth aspect of the present inventive subject matter, there is provided a light fixture comprising:

at least a first light engine, and at least a first surface, the light fixture configured such that upon supplying electricity to the light fixture:

light having a first color point is incident on at least a portion of the first surface, and light exiting the light fixture has a cumulative color of a second color point, the first color point spaced from the second color point.

Light fixtures in accordance with the fourth aspect of the present inventive subject matter are capable of providing a phenomenon in which a person (e.g., a person in a room in which such a light fixture is installed) can see light of a first color point incident on a surface (i.e., the first surface) of the light fixture (e.g., a sidewall as discussed herein) and feel the sensation of perceiving the light from the light fixture to have such color point, while the actual cumulative light output from the light fixture is of a different color point ("cumulative light output from the light fixture" meaning a mixture of all of the light output from the light fixture, or substantially all of such light, or at least 90% of such light). Such a light fixture can thus achieve such a phenomenon where desired, e.g., in some instances it can be advantageous to provide to a person a sensation that a light fixture is outputting light that is of an aesthetically more pleasing color point when the light fixture is actually outputting (in aggregate, or cumulatively) light that is of an aesthetically less pleasing color point. In a representative example, light output from a light fixture having a cumulative color temperature (or correlated color temperature) of 5300K is frequently considered not aesthetically pleasing, and in accordance with a light fixture described in the present paragraph (and the paragraph preceding the present paragraph), a person's vision can be "tricked" into thinking that the light output from the light fixture is of a more pleasing color temperature (i.e., a lower color temperature, providing a sensation of "warmer" light) by having at least a first surface of the light fixture on which light of such more pleasing color temperature is incident (and typically a large portion of such light is reflected by the first surface). The phenomenon described in the present paragraph can be enhanced where the light that is incident on the at least a first surface is of comparatively high luminosity, i.e., is of wavelength (or wavelengths and/or wavelength ranges) for which human visual perception of brightness is comparatively high; as is well known by persons of skill in the art, the photopic luminosity function (also known as luminous efficiency function) describes the average spectral sensitivity of human visual perception of brightness, based on subjective judgments of which of a pair of different-colored lights is brighter, to describe relative sensitivity to light of different wavelengths. The color temperatures that are typically considered more pleasant are typically of higher luminosity, thereby further enhancing the phenomenon described in the present paragraph where light of an aesthetically pleasing color temperature that also has high luminosity is incident on the at least a first surface.

As noted above, in accordance with the fourth aspect of the present inventive subject matter, there is provided a light fixture comprising:
  at least a first light engine, and
  at least a first surface,
  the light fixture configured such that upon supplying electricity to the light fixture:
  light having a first color point is incident on at least a portion of the first surface, and
  light exiting the light fixture has a cumulative color of a second color point,
  the first color point spaced from the second color point.

In some embodiments of light fixtures in accordance with the fourth aspect of the present inventive subject matter, including some embodiments that include or do not include any of the features described herein:
  said first color point is of a first correlated color temperature,
  said second color point is of a second correlated color temperature, and
  said first correlated color temperature is lower than said second correlated color temperature.

In some embodiments of light fixtures in accordance with the fourth aspect of the present inventive subject matter, including some embodiments that include or do not include any of the features described herein:
  the light fixture further comprises at least a first sidewall, and
  the first surface is on the first sidewall.

In some embodiments of light fixtures in accordance with the fourth aspect of the present inventive subject matter, including some embodiments that include or do not include any of the features described herein:
  the light fixture further comprises a second light engine,
  said light incident on the first surface has a first ratio (which can be as high as infinity) of light output from the second light engine to light output from the first light engine,
  said light exiting the light fixture has a second ratio (which can be as low as zero) of light output from the second light engine to light output from the first light engine, and
  said first ratio is larger than said second ratio.

In some embodiments in accordance with the third aspect of the present inventive subject matter, there are provided light fixtures that comprise at least some of the features described above in connection with the first aspect of the present invention, e.g., light fixtures (artificial skylights), in which at least a portion of a first light engine resembles a sky (e.g., a surface of the first light engine looks like the sky to a viewer), and light exiting from a second light engine has one or more characteristics that resemble that (or those) of at least a portion of light emitted by (and received from) the sun. In some of such embodiments, as discussed above in accordance with the first aspect of the present inventive subject matter:
  the light fixture comprises at least a first light engine and a second light engine;
  light exiting the first light engine (i.e., upon supplying electricity to a light source of the first light engine) has x, y color coordinates which define a point on a 1931 CIE Chromaticity Diagram which is within a quadrilateral area with vertices having x, y coordinates of (0.37, 0.34), (0.35, 0.38), (0.15, 0.20), and (0.20, 0.14) (FIG. 1 is a plot, on a 1931 CIE Chromaticity Diagram, of a region 11 defined as such, i.e., the quadrilateral area with vertices having such x, y coordinates (and in some embodiments, light exiting the first light engine has x, y color coordinates which define a point which is within a quadrilateral area with vertices having x, y coordinates of (0.32, 0.31), (0.30, 0.33), (0.15, 0.17), and (0.17, 0.14));
  light exiting the second light engine (i.e., upon supplying electricity to a light source of the second light engine) has x, y color coordinates which define a point on a 1931 CIE Chromaticity Diagram which is within an area with vertices having x, y coordinates of (0.29, 0.32), (0.32, 0.29), (0.41, 0.36), (0.48, 0.39), (0.48, 0.43), (0.40, 0.41), and (0.35, 0.38) (FIG. 2 is a plot, on a 1931 CIE Chromaticity Diagram, of a region 21 defined as such, i.e., the area with vertices having such x, y coordinates) (and in some embodiments, within an area with vertices having x, y coordinates of (0.30, 0.34), (0.30, 0.30), (0.39, 0.36), (0.45, 0.39), (0.47, 0.43), (0.40, 0.41), and (0.35, 0.38)); and
  the color point (i.e., the combination of x, y color coordinates) of the light exiting the first light engine may be but typically is not the same as the color point of the light exiting the second light engine.

In accordance with a fifth aspect in accordance with the present inventive subject matter, there is provided a light fixture comprising:
  at least first and second light engines,
  the first light engine configured to output light of a first color point,
  the second light engine configured to output light of a second color point,
  the first color point spaced from the second color point, light distribution characteristics of the first and second light engines different from each other.

In some embodiments of light fixtures in accordance with the fifth aspect of the present inventive subject matter, including some embodiments that include or do not include any of the features described herein:
the first light engine comprises at least one light emitter, and/or
the second light engine comprises at least one light emitter.

In some embodiments of light fixtures in accordance with the fifth aspect of the present inventive subject matter, including some embodiments that include or do not include any of the features described herein:
the first light engine comprises at least one LED, and/or
the second light engine comprises at least one LED.

In some embodiments of light fixtures in accordance with the fifth aspect of the present inventive subject matter, including some embodiments that include or do not include any of the features described herein:
the first light engine comprises at least two light emitters, and/or
the second light engine comprises at least two light emitters.

In some embodiments of light fixtures in accordance with the fifth aspect of the present inventive subject matter, including some embodiments that include or do not include any of the features described herein:
the first light engine comprises at least two LEDs, and/or
the second light engine comprises at least two LEDs.

In some embodiments of light fixtures in accordance with the fifth aspect of the present inventive subject matter, including some embodiments that include or do not include any of the features described herein, the first light engine is spaced from the second light engine laterally and/or vertically relative to the second light engine. The expression "first light engine spaced laterally relative to the second light engine" means that the first light engine is spaced from the second light engine in a plane perpendicular to an axis of light distribution of the second light engine. The expression "first light engine spaced vertically relative to the second light engine" means that the first light engine is spaced from the second light engine in a direction along the axis of light distribution of the second light engine. Accordingly, the expression "the first light engine is spaced from the second light engine laterally and/or vertically relative to the second light engine" means that the first light engine is [1] spaced from the second light engine in a plane perpendicular to an axis of light distribution of the second light engine, [2] spaced from the second light engine along the axis of light distribution of the second light engine, or [3] spaced from the second light engine along a line spaced from and parallel to the axis of light distribution of the second light engine. For instance, in some of such embodiments, there can be provided a plurality of light engines (in which at least two of such light engines are configured to output light of respective differing color points), in which a first of such light engines is in a first location and others of such light engines are spaced laterally around the first light engine (e.g., the first light engine has a generally square surface through which output light exits the first light engine, and other light engines are positioned as a ring around the first light engine)(i.e., as an example where a first light engine is spaced from a second light engine, and from other light engines, laterally.

In some embodiments of light fixtures in accordance with the fifth aspect of the present inventive subject matter, including some embodiments that include or do not include any of the features described herein, the light fixture further comprises at least a third light engine.

In some embodiments of light fixtures in accordance with the fifth aspect of the present inventive subject matter, including some embodiments that include or do not include any of the features described herein:
the first light engine is configured to output light that has a first axis of light distribution,
the second light engine is configured to output light that has a second axis of light distribution, and
the first axis of light distribution differs from the second axis of light distribution. In some of such embodiments, an angle of the first axis of light distribution relative to a first plane differs from an angle of the second axis of light distribution relative to the first plane, and in some of those embodiments, the first and second light engines are configured and oriented such that the first plane is defined by a region through which at least some light output from the first light engine and at least some light output from the second light engine exits the light fixture.

In some embodiments of light fixtures in accordance with the fifth aspect of the present inventive subject matter, including some embodiments that include or do not include any of the features described herein:
the first light engine is configured to output light that has a first peak intensity angle relative to a first plane,
the second light engine is configured to output light that has a second peak intensity angle relative to the first plane, and
the first peak intensity angle differs from the second peak intensity angle. In some of such embodiments, the first and second light engines are configured and oriented such that the first plane is defined by a region through which at least some light output from the first light engine and at least some light output from the second light engine exits the light fixture.

In some embodiments of light fixtures in accordance with the fifth aspect of the present inventive subject matter, including some embodiments that include or do not include any of the features described herein:
the light fixture further comprises at least a first control element,
the at least a first control element controls independently at least a brightness of light exiting from the first light engine and a brightness of light exiting from the second light engine.

In some embodiments of light fixtures in accordance with the fifth aspect of the present inventive subject matter, including some embodiments that include or do not include any of the features described herein:
the light fixture further comprises at least a first control element,
the at least a first control element controls at least a brightness of light exiting from the first light engine and a brightness of light exiting from the second light engine. In some of such embodiments:
the first control element controls the brightness of light exiting from the second light engine based on the brightness of light exiting from the first light engine; or
the first control element controls the brightness of light exiting from at least one of the first light engine and the second light engine based on a parameter selected from among (1) a color point of a mixture of light exiting from the light fixture, (2) a brightness of light exiting from the light fixture, (3) a time of day and (4) a melatonin suppression setting.

In some embodiments of light fixtures in accordance with the fifth aspect of the present inventive subject matter, including some embodiments that include or do not include any of the features described herein, the light fixture further comprises at least a first light extraction element that affects light distribution characteristics of light exiting from at least one of the first and second light engines.

In some embodiments of light fixtures in accordance with the fifth aspect of the present inventive subject matter, including some embodiments that include or do not include any of the features described herein, the light fixture further comprises at least a first diffuser that affects light distribution characteristics of light exiting from at least one of the first and second light engines.

In accordance with a sixth aspect in accordance with the present inventive subject matter, there is provided a light fixture comprising:
 at least a first light engine and a second light engine; and
 a first sidewall,
 the first light engine comprising at least a first light exit surface,
 the first sidewall defining a space,
 at least a first light exit region at a boundary of the space,
 the first light engine positioned and oriented such that at least some light that exits the first light exit surface passes through at least part of the space and exits the space through the first light exit region, and
 the second light engine positioned and oriented such that at least some light that exits the second light engine exits the space through the first light exit region.

In some embodiments of light fixtures in accordance with the sixth aspect of the present inventive subject matter, including some embodiments that include or do not include any of the features described herein:
 the first light engine is configured to output light of a first color point,
 the second light engine is configured to output light of a second color point, and
 the first color point is spaced from the second color point.

In some embodiments of light fixtures in accordance with the sixth aspect of the present inventive subject matter, including some embodiments that include or do not include any of the features described herein:
 light incident on the first sidewall has a first ratio (which can be as high as infinity) of light output from the second light engine to light output from the first light engine,
 light output from the light fixture has a second ratio (which can be as low as zero) of light output from the second light engine to light output from the first light engine, and
 the first ratio is larger than the second ratio.

In some embodiments of light fixtures in accordance with the sixth aspect of the present inventive subject matter, including some embodiments that include or do not include any of the features described herein, the second light engine is movable relative to the first light engine and the first sidewall. In some of such embodiments:
 movement of the second light engine relative to the first light engine corresponds to passage of time,
 a first position of the second light engine relative to the first light engine is substantially the same at a first time of day on at least two consecutive days,
 a second position of the second light engine relative to the first light engine is substantially the same at a second time of day on said at least two consecutive days, said first position differs from said second position, and said first time of day differs from said second time of day.

In some embodiments of light fixtures in accordance with the sixth aspect of the present inventive subject matter, including some embodiments that include or do not include any of the features described herein:
 the first sidewall has at least a first sidewall aperture, and
 at least some light that exits the second light engine enters the space through the first sidewall aperture. In some of such embodiments:
 the light fixture further comprises at least a first screen; and
 at least some light that exits the second light engine passes through the first screen.

In some embodiments of light fixtures in accordance with the sixth aspect of the present inventive subject matter, including some embodiments that include or do not include any of the features described herein, the second light engine is in the space.

In some embodiments of light fixtures in accordance with the sixth aspect of the present inventive subject matter, including some embodiments that include or do not include any of the features described herein:
 the first sidewall comprises at least a second light exit surface, and
 upon supplying electricity to the light fixture, light exits the second light exit surface. In some of such embodiments, at least one of [A], [B], [C] or [D] (below) is satisfied:
 [A] the first sidewall comprises at least a first light emitter, the first sidewall comprises at least one light-transporting structure, and/or the first sidewall comprises at least one light-transmitting structure, or
 [B] the light fixture further comprises at least a first control element, the at least a first control element controls independently at least a brightness of light exiting from the first light exit surface and a brightness of light exiting from the second light exit surface, or
 [C] the light fixture further comprises at least a first control element, the at least a first control element controls independently at least a color point of light exiting from the first light exit surface and a color point of light exiting from the second light exit surface, or
 [D] the light fixture further comprises at least a first control element, the at least a first control element controls at least one of:
  a brightness of light exiting from at least a first portion of the sidewall,
  a color point of light exiting from the first light engine, and
  a color point of light exiting from the second light engine.

In accordance with a seventh aspect in accordance with the present inventive subject matter, there is provided a light fixture comprising:
 a first sidewall; and
 at least a first control element,
 the first sidewall defining a space,
 at least a first light exit region at a boundary of the space,
 a first light engine positioned and oriented such that at least some light that exits the first light engine passes through the first sidewall into the space,
 the at least a first control element:
 (1) independently controls a brightness of light exiting from a first portion of the sidewall and a brightness of light exiting from a second portion of the sidewall, and/or (2) independently controls a color point of light exiting from a first portion of the sidewall and a color point of light exiting from a second portion of the sidewall.

In some embodiments of light fixtures in accordance with the seventh aspect of the present inventive subject matter, including some embodiments that include or do not include any of the features described herein, the first control element is configured to adjust the brightness of light exiting from a first portion of the sidewall and a brightness of light exiting from a second portion of the sidewall based on the time of day (e.g., according to a repeating 24-hour cycle).

In some embodiments of light fixtures in accordance with the seventh aspect of the present inventive subject matter, including some embodiments that include or do not include any of the features described herein, the first control element is configured to adjust the color point of light exiting from a first portion of the sidewall and the color point of light exiting from a second portion of the sidewall based on the time of day (e.g., according to a repeating 24-hour cycle), and (1) the color point of light exiting from the first portion of the sidewall at a first time of day differs from the color point of light exiting from the first portion of the sidewall at a second time of day, (2) the color point of light exiting from the second portion of the sidewall at the first time of day differs from the color point of light exiting from the second portion of the sidewall at the second time of day, and (3) the color point of light exiting from the first portion of the sidewall at the first time of day differs from the color point of light exiting from the second portion of the sidewall at the first time of day.

In some embodiments of light fixtures in accordance with the seventh aspect of the present inventive subject matter, including some embodiments that include or do not include any of the features described herein, the first control element is configured to adjust the brightness and the color point of light exiting from a first portion of the sidewall, and the brightness and the color point of light exiting from a second portion of the sidewall based on the time of day (e.g., according to a repeating 24-hour cycle).

In some embodiments of light fixtures in accordance with the seventh aspect of the present inventive subject matter, including some embodiments that include or do not include any of the features described herein:

the first sidewall has at least a first sidewall aperture, and at least some light that exits the first light engine enters the space through the first sidewall aperture. In some of such embodiments:

the light fixture further comprises at least a first screen; and at least some light that exits the first light engine passes through the first screen.

In some embodiments of light fixtures in accordance with the seventh aspect of the present inventive subject matter, including some embodiments that include or do not include any of the features described herein:

the first sidewall comprises at least said first light engine,
the first sidewall comprises at least one light-transporting structure, and/or
the first sidewall comprises at least one light-transmitting structure.

An eighth aspect of the present inventive subject matter is directed to a method of supplying light, comprising:

supplying electricity to a light fixture, the light fixture comprising:

at least a first light engine and a second light engine; and
a first sidewall, the first light engine comprising at least a first light exit surface, whereby:

light that has x, y color coordinates which define a point on a 1931 CIE Chromaticity Diagram which is within a quadrilateral area with vertices having x, y coordinates of (0.37, 0.34), (0.35, 0.38), (0.15, 0.20), and (0.20, 0.14) (and in some embodiments, within a quadrilateral area with vertices having x, y coordinates of (0.32, 0.31), (0.30, 0.33), (0.15, 0.17), and (0.17, 0.14)) exits the first light engine through the first light exit surface, and light that has x, y color coordinates which define a point on a 1931 CIE Chromaticity Diagram which is within an area with vertices having x, y coordinates of (0.29, 0.32), (0.32, 0.29), (0.41, 0.36), (0.48, 0.39), (0.48, 0.43), (0.40, 0.41), and (0.35, 0.38) (and in some embodiments, within an area with vertices having x, y coordinates of (0.30, 0.34), (0.30, 0.30), (0.39, 0.36), (0.45, 0.39), (0.47, 0.43), (0.40, 0.41), and (0.35, 0.38)) exits the second light engine, the first sidewall defining a space, at least a first light exit region at a boundary of the space, the first light engine positioned and oriented such that at least some light that exits the first light exit surface passes through at least part of the space and exits the space through the first light exit region, and the second light engine positioned and oriented such that at least some light that exits the second light engine exits the space through the first light exit region.

In some embodiments of methods in accordance with the eighth aspect of the present inventive subject matter, including some embodiments that include or do not include any of the features described herein, the method can optionally further comprise adjusting the brightness of light output from the first light engine and/or adjusting the brightness of light output from the second light engine so that a subject receives light that provides a CS value of at least 0.3 at an illuminance of 300 lux during a first part of the day, and a CS value of less than 0.15 at an illuminance of 200 lux (and/or a CS value of less than 0.2 at an illuminance of 300 lux) during a second part of the day.

A ninth aspect of the present inventive subject matter is directed to a method of supplying light, comprising:

moving a second light engine relative to a first light engine, the first light engine comprising at least a first light exit surface, outputting light that has x, y color coordinates which define a point on a 1931 CIE Chromaticity Diagram which is within a quadrilateral area with vertices having x, y coordinates of (0.37, 0.34), (0.35, 0.38), (0.15, 0.20), and (0.20, 0.14) (and in some embodiments, within a quadrilateral area with vertices having x, y coordinates of (0.32, 0.31), (0.30, 0.33), (0.15, 0.17), and (0.17, 0.14)) from the first light engine through the first light exit surface, and outputting light that has x, y color coordinates which define a point on a 1931 CIE Chromaticity Diagram which is within an area with vertices having x, y coordinates of (0.29, 0.32), (0.32, 0.29), (0.41, 0.36), (0.48, 0.39), (0.48, 0.43), (0.40, 0.41), and (0.35, 0.38) (and in some embodiments, within an area with vertices having x, y coordinates of (0.30, 0.34), (0.30, 0.30), (0.39, 0.36), (0.45, 0.39), (0.47, 0.43), (0.40, 0.41), and (0.35, 0.38)) from the second light engine, at least some light that exits the first light exit surface passing through at least part of a space and exiting the space through a first light exit region, and at least some light that exits the second light engine exiting the space through the first light exit region.

In some embodiments of methods in accordance with the ninth aspect of the present inventive subject matter, including some embodiments that include or do not include any of the features described herein:

the first light engine and the second light engine are in a light fixture that further comprises a first sidewall that defines said space.

A tenth aspect of the present inventive subject matter is directed to a method of supplying light, comprising:

outputting light from at least a first light engine and a second light engine, at least the first light engine and the second light engine in a light fixture, light output from the first light engine providing a first CS value at a given illuminance, light output from the second light engine providing a second CS value at the same illuminance, the first CS value different from the second CS value.

In some embodiments of methods in accordance with the tenth aspect of the present inventive subject matter, including some embodiments that include or do not include any of the features described herein:

the light output from the first light engine is of a first color point, the light output from the second light engine is of a second color point, and the first color point is spaced from the second color point.

An eleventh aspect of the present inventive subject matter is directed to methods of affecting a subject's (e.g., a human's) biological melatonin levels, comprising exposing such subject to light output from a light fixture (as described herein, including but not limited to light fixtures in accordance with the first, second, fourth, fifth, sixth and seventh aspects) in accordance with the present inventive subject matter.

In some embodiments of methods in accordance with the eleventh aspect of the present inventive subject matter, including some embodiments that include or do not include any of the features described herein, the method comprises exposing a subject to light output from a light fixture (e.g., a light fixture in accordance with the present inventive subject matter) to provide a CS value in said subject of at least 0.3 at an illuminance of 300 lux.

In some embodiments of methods in accordance with the eleventh aspect of the present inventive subject matter, including some embodiments that include or do not include any of the features described herein, the method comprises exposing a subject to light output from a light fixture (e.g., a light fixture in accordance with the present inventive subject matter) to provide a CS value in said subject of at least 0.3 at an illuminance of 300 lux during part of the day, and exposing said subject to light output from said light fixture to provide a CS value in said subject of less than 0.3 during a different part of the day (e.g., at an illuminance of 300 lux, and/or a CS value of less than 0.25 (in some cases less than 0.2) at an illuminance of 200 lux).

In some embodiments of methods in accordance with the eleventh aspect of the present inventive subject matter, including some embodiments that include or do not include any of the features described herein, the method comprises exposing a subject to light output from a light fixture (e.g., a light fixture in accordance with the present inventive subject matter) to provide a CS value in said subject of at least 0.3 at an illuminance of 300 lux during part of the day, and exposing said subject to light output from said light fixture to provide a CS value in said subject of less than 0.15 at an illuminance of 200 lux (and/or less than 0.2 at an illuminance of 300 lux) during a different part of the day.

In some embodiments of methods in accordance with the eleventh aspect of the present inventive subject matter, including some embodiments that include or do not include any of the features described herein, the method comprises exposing a subject to light output from a light fixture (e.g., a light fixture in accordance with the present inventive subject matter) to provide a CS value in said subject of at least 0.3 at an illuminance of 300 lux during at least a first part of the day, and exposing said subject to light output from said light fixture to provide a CS value in said subject of less than 0.15 during at least a second part of the day, the lumens output during the second part of the day comprising at least 50% (and in some embodiments at least 60%, 70%, 80% or 90%) of the lumens output during the first part of the day.

It is well known that the CCT or color of daylight changes over the course of a day, seasons, due to weather. etc. In some of the embodiments described in the preceding two sentences, the CCT of light exiting from the first light engine (CCT1) differs from the CCT of light exiting from the second light engine (CCT2), whereby the CCT for the overall light exiting from the light fixture includes at least a contribution of CCT1 from the first light engine and a contribution of CCT2 from the second light engine. In such embodiments, change in CCT during the day can be achieved by changing the ratio of light contribution from the "sun" (second light engine) to light contribution from the "sky" (first light engine).

It is also well known that the color of the sun and the sky portions of daylight change over the course of a day, seasons, due to weather. etc. In some of the embodiments described above, the CCT of the light exiting the first light engine (CCT1) may be made adjustable by including in its fabrication at least two different color light-emitting sources whose output is independently controlled. Likewise, the CCT of the light exiting the second light engine (CCT2) may made adjustable by including in its fabrication at least two different color light-emitting sources whose output is independently controlled.

In some embodiments of light fixtures in accordance with the present inventive subject matter, including some embodiments that include or do not include any of the features described herein, the color and/or the brightness of:

light that exits from the first light engine (or any portion thereof), light that exits from the second light engine (or any portion thereof), and/or light that exits from a sidewall, can be varied over time (e.g., during the course of the day) automatically (e.g., programmed accordingly to a daily pattern, a monthly pattern, based on sensed condition, etc.) or manually by a user (e.g., by inputting commands in a control that provides signals wirelessly or through a wired connection). For instance, color-changing LED technology with programmable correlated color temperature and/or intensity settings may be employed for these purposes.

The color and/or the brightness of light that exits from one component (e.g., a first light engine) can be controlled independently of the color and/or the brightness of light that exits from another component (e.g., a second light engine or a sidewall).

In some embodiments that comprise one or more sidewall that comprises a light exit surface, light exiting various portions of the sidewall can be adjusted over the course of the day (e.g., with a box-shaped sidewall, one side can be illuminated more strongly in the morning hours and less in the late afternoon hours, and an opposite side can be illuminated less in the morning hours and more in the late afternoon hours to provide or enhance the appearance of movement of the sun during the day.

As discussed above, it is well known that light sources that emit light of respective differing hues (two or more) can be combined to generate mixtures of light that have desired hues. Any light described herein can be provided as a mixture of two or more portions of light that can be of differing color points. For example, the first light engine (and/or the second light engine, and/or any other light engine) can comprise a plurality of LEDs that emit light of two or more respective color points. A light engine that comprises two or more light emitters that emit light of two or more respective color points can be tuned over a range of color points by changing the contribution from each of the two or more light emitters that emit light of respective different color points.

Some embodiments of light fixtures in accordance with the present inventive subject matter comprise a control element (or control elements), which (or each of which) can control one or more of:

a brightness of light emitted from at least a first portion of a sidewall (if included), a brightness of light emitted from at least a second portion of a sidewall (if included), a brightness of light emitted from a first light engine, a brightness of light emitted from a second light engine (if included), a color point of light emitted from at least a first portion of a sidewall (if included), a color point of light emitted from at least a second portion of a sidewall (if included), a color point of light emitted from a first light engine, and a color point of light emitted from a second light engine (if included).

As a first representative embodiment of a light source that comprises plural light emitters, a first light engine can comprise a first LED and a second LED, in which the first LED emits light of a first color point, the second LED emits light of a second color point (different from the first color point), and the light output from the first light engine, which is a mixture of light emitted by the first LED and light emitted by the second LED, can be adjusted (to any point along a tie line extending from the first color point to the second color point) by changing the contribution from the first LED relative to the contribution from the second LED.

As a second representative embodiment of a light source that comprises plural light emitters, a first light engine can comprise a first LED, a second LED and a third LED, in which the first LED emits light of a first color point, the second LED emits light of a second color point (different from the first color point), the third LED emits light of a third color point (different from the first and second color points), and the light output from the first light engine, which is a mixture of light emitted by the first LED, light emitted by the second LED and light emitted by the third LED, can be adjusted (to any point within an area having the first, second and third color points as its vertices) by changing the contribution from the first LED, the second LED and the third LED relative to each other.

Light from two or more respective light sources can be mixed in any suitable way, e.g., light from one or more of the respective light sources can travel optionally through the same or different light transporting elements, light transmitting elements, etc.

Representative examples of light sources that comprise light emitters that emit light of two or more respective color points, and in which the respective contributions of light of the respective color points can be adjusted, include True-White technology products available from Cree, Inc., Durham, N.C.

By providing light engines that comprise light emitters that emit light of two or more respective color points, it is possible for such a light engine to emit mixtures of light of different color points, e.g., multiple points within the respective regions depicted in FIG. 1, FIG. 2 and FIG. 3, for example, some of all of the points within the respective regions depicted in FIG. 1, FIG. 2 and FIG. 3, by changing the contribution from each of the multiple light emitters in such a light engine.

A representative example of a light fixture in accordance with the first aspect or the second aspect of the present inventive subject matter comprises:

an edge-lit flat panel (e.g., an Essentia flat panel available from Cree, Inc., Durham, N.C.) with blue light-emitting LEDs (e.g., blue LEDs that emit light having a dominant wavelength of 475 nm) and white light-emitting LEDs (e.g., LEDs that emit light having a correlated color temperature of about 5000K) as the first light engine; and four sidewalls comprising back-lit light boxes according to FIG. 18 with cool-white light-emitting LEDs (e.g., LEDs that emit light having a correlated color temperature of about 6500K) and warm-white light-emitting LEDs (e.g., LEDs that emit light having a correlated color temperature of about 3000K) as the second light engine.

FIG. 28 shows the color points of light emitted by representative examples of the two types of LEDs used in the fabrication of the first light engine (the "sky"), and light emitted by the two types of LEDs used in the fabrication of the second light engine (the "sun") plotted on a portion of the CIE 1931 Chromaticity Diagram. For each LED type, multiple data points are shown in FIG. 28, each point corresponding to a different power supplied to the LEDs. Also shown in FIG. 28 are the color points for four settings of the skylight overall, wherein the power to each of the four LED types has been adjusted so that the skylight as a unit delivers a desirable brightness, color, and visual appearance. These four settings correspond to CCT values from approximately 3200K to 5200K, which are intended to provide, and do provide, the visual impression of a skylight at different times of day.

Table 1 summarizes relevant characteristics for the four skylight settings, including the electrical power supplied to each of the four LED types.

TABLE 1

| | LED string power in watts | | | | Select characteristics of light delivered by skylight | | | | | | |
|---|---|---|---|---|---|---|---|---|---|---|---|
| Preset name | Sun cool white | Sun warm white | Sky blue | Sky white | Lumens | x | Y | CCT/K | duv | CRI | R9 |
| Mid-day | 16.4 | 26.8 | 10.0 | 6.7 | 5642 | 0.3394 | 0.3318 | 5173 | −0.0080 | 85 | 80 |
| Morning | 3.1 | 34.0 | 10.0 | 6.7 | 4745 | 0.3631 | 0.3431 | 4281 | −0.0113 | 82 | 81 |
| Afternoon | 3.1 | 34.0 | 6.3 | 2.6 | 4252 | 0.3826 | 0.3586 | 3792 | −0.0094 | 86 | 91 |
| Evening | 1.8 | 19.7 | 0.0 | 2.6 | 2538 | 0.4209 | 0.3900 | 3171 | −0.0034 | 94 | 68 |

Results in Table 1 and FIG. 28 were measured in an integrating sphere.

As shown in FIG. 28, in this case the light delivered by the skylight has been adjusted to have a white color point slightly below the BBL (blackbody locus). In some embodiments, the color of light delivered may be above, on, or below the BBL.

Since four LED types have been used in this case, in general there are multiple solutions (i.e. sets of supplied power) that can be used to deliver light having a given color point. Thus the powers listed in Table 1 are one set of many possible sets—others may be desirable (e.g. to maximize CRI, efficiency, or blueness of the sky).

The number of presets is not limited to four. With suitable controls, the number of possible color points within the color gamut defined by the four LED types is virtually unlimited.

In other embodiments, the number of LED types may be greater than four.

In a preferred embodiment, the sun light engine can comprise three (or more) LED types such that the light emitted by the sun light engine may be precisely controlled a in two-dimensional color space (e.g. to stay on the BBL at any achievable CCT value.)

In other embodiments, the color gamut of the selected LED types may be larger than shown in FIG. 28 so that the achievable CCT/color range is correspondingly larger. In particular, the choice of warm white LEDs in the sun light engine, including but not limited to BSY+BSY+RDO combinations such as are found in Cree True White fixtures ("BSY" and "RDO" are defined below). For example, it may be desirable for a skylight fixture to be able to deliver light having a similar color point to natural light around sunset, which can have a very low CCT (<2700K).

"BSY" is defined as light that has x, y color coordinates (on a 1931 CIE Chromaticity Diagram) which define a point that is within either or both of:

a first area on the 1931 CIE Chromaticity Diagram enclosed by first, second, third, fourth and fifth line segments, the first line segment connecting a first point to a second point, the second line segment connecting the second point to a third point, the third line segment connecting the third point to a fourth point, the fourth line segment connecting the fourth point to a fifth point, and the fifth line segment connecting the fifth point to the first point, the first point having x, y coordinates of 0.32, 0.40, the second point having x, y coordinates of 0.36, 0.48, the third point having x, y coordinates of 0.43, 0.45, the fourth point having x, y coordinates of 0.42, 0.42, and the fifth point having x, y coordinates of 0.36, 0.38; and a second area on the 1931 CIE Chromaticity Diagram enclosed by sixth, seventh, eighth, ninth and tenth line segments, the fifth line segment connecting a fifth point to a sixth point, the seventh line segment connecting the seventh point to an eighth point, the eighth line segment connecting the eighth point to a ninth point, the ninth line segment connecting the ninth point to a tenth point, and the tenth line segment connecting the tenth point to the sixth point, the sixth point having x, y coordinates of 0.29, 0.36, the seventh point having x, y coordinates of 0.32, 0.35, the eighth point having x, y coordinates of 0.41, 0.43, the ninth point having x, y coordinates of 0.44, 0.49, and the tenth point having x, y coordinates of 0.38, 0.53 (in the 1976 CIE Chromaticity Diagram, the sixth point has u', v' coordinates of 0.17, 0.48, the seventh point has u', v' coordinates of 0.20, 0.48, the eighth point has u', v' coordinates of 0.22, 0.53, the ninth point has u', v' coordinates of 0.22, 0.55, and the tenth point has u', v' coordinates of 0.18, 0.55.

"RDO" is defined as red-orange, corresponding to light emitted with a dominant wavelength between 600 nm and 630 nm.

As noted above, FIG. 29 is a photo of an embodiment of an artificial skylight in accordance with the present inventive subject matter, where the sky ("first light engine") has color point (0.3135, 0.3237), and the sun ("second light engine") has color point (0.3451, 0.3516), and FIG. 30 is a photo of an embodiment of an artificial skylight in accordance with the present inventive subject matter, where the sky ("first light engine") has color point (0.2383, 0.2472), and the sun ("second light engine") has color point (0.3451, 0.3516). FIGS. 29 and 30 show embodiments in accordance with the present inventive subject matter that are artificial skylights (i.e., they appear to be skylights) that avoid problems with conventional skylights and that provide benefits that are provided by conventional skylights.

In each of the embodiments shown in FIGS. 29 and 30, a first light engine resembles a sky (i.e., a surface of the first light engine looks like the sky to a viewer), and light exiting from a second light engine has characteristics that resemble those of light emitted by (and received from) the sun. The artificial skylights shown in FIGS. 29 and 30 can thus provide the ability to supply light (in residential buildings, commercial buildings, other buildings and other structures) while avoiding or reducing (in comparison to other devices, such as conventional skylights) water leakage, providing lower heat loss, providing light on overcast or stormy days, simplifying installation, providing the ability for installation (e.g., in locations where installation of a skylight would be problematic or impossible, e.g., in the first story of a multi-story structure, or in a building in which the roof is spaced a large distance from a ceiling), providing the ability to control light exiting from the device into an office, a room or any other space (e.g., controlling the brightness and/or the color of light exiting from the light fixture). In addition, the artificial skylights shown in FIGS. 29 and 30 can simplify cleaning (e.g., in comparison to conventional skylights, the skylights shown in FIGS. 29 and 30 can be more easily accessed, and/or can be removed from a structure on which they are mounted).

Any light fixture disclosed herein can, if desired, comprise one or more luminescent materials. A luminescent material is a material that emits a responsive radiation (e.g., visible light) when excited by a source of exciting radiation. In many instances, the responsive radiation has a wavelength (or hue) that is different from the wavelength (or hue) of the exciting radiation. Persons of skill in the art are familiar with, and have ready access to, a variety of luminescent materials that emit light having a desired peak emission wavelength and/or dominant emission wavelength, or a desired hue, and any of such luminescent materials, or any combinations of such luminescent materials, can be employed, if desired.

One type of luminescent material are phosphors, which are readily available and well known to persons of skill in the art. Other examples of luminescent materials include scintillators, day glow tapes and inks that glow in the visible spectrum upon illumination with ultraviolet light.

Persons of skill in the art are familiar with, and have ready access to, a variety of luminescent materials that emit light having a emission wavelengths (dominant or peak) in well known ranges, and any of such luminescent materials, and any desired combinations of such luminescent materials, can be employed in accordance with the present inventive subject matter.

Several non-limiting representative examples of luminescent materials that can be employed in the present inventive subject matter include cerium-doped yttrium aluminum garnet (aka "YAG:Ce" or "YAG"), $CaAlSiN:Eu^{2+}$ (aka "CASN" or "BR01"), BOSE, quantum dots, nitride phosphors (such as $(Sr, Ca)SiAlN_3:Eu^{2+}$) and narrow band phosphors (such as $K_2SiF_6:Mn^{4+}$).

Luminescent materials, if included, can be in any suitable form. For example, the luminescent element can be embedded in a resin (i.e., a polymeric matrix), such as a silicone material, an epoxy material, a glass material or a metal oxide material, and/or can be applied to one or more surfaces of a resin.

As noted above, in accordance with a first aspect of the present inventive subject matter, there are provided light fixtures (artificial skylights), in which at least a portion of a first light engine resembles a sky (e.g., a surface of the first light engine looks like the sky to a viewer), and light exiting from a second light engine has one or more characteristics that resemble that (or those) of at least a portion of light emitted by (and received from) the sun.

Characteristics of light fixtures in accordance with the present inventive subject matter can be evaluated in a wide variety of ways. One example of a way to evaluate the light fixtures in accordance with the present inventive subject matter is to allow a number of test subjects ("observers", i.e., persons, e.g., ten persons, one at a time) to observe a light fixture in accordance with the present inventive subject matter (and optionally also, simultaneously or in sequence) to observe another light fixture and/or a conventional skylight, and to obtain from each test subject a score (on the respective scales identified below) for each of a number of characteristics, e.g., the following:

[A] Shadows: appearance of shadows on the wall (i) directly and (ii) cast from the test subject's hand near the wall; direct sunlight causes sharp shadows, which are a visual cue of the sun's presence; skylights with a diffuser produce a softer, more even shadow—Scale: 1 (clearly artificial); 4 (just like a skylight); 2 and 3 (between 1 and 4, with 2 more toward artificial).

[B] Sun Intensity: impression of light directionality created by brightness contrast between where the sun is hitting vs. overall ambient light, particularly when looking at the wall; direct sunlight is intense and directional, creating contrast when coming through a skylight or a window—Scale: 1 (clearly artificial); 4 (looks just like a real skylight); 2 and 3 (between 1 and 4, with 2 more toward artificial).

[C] Color Uniformity on Wall: when the skylight has two colors with different directionality, some color non-uniformity of the lit space is unavoidable; is it noticeable? objectionable? natural light typically—but not always—provides good color uniformity—Scale: 1 (clearly artificial); 4 (looks just like a real skylight); 2 and 3 (between 1 and 4, with 2 more toward artificial).

[D] Glare: gauge comfort level when looking directly at the skylight from different positions; although direct sunlight is inherently glary, a hypothesis is that less glare from the fixture is preferable and would make the skylight more widely deployable—Scale: 1 (acceptable); −1 (not acceptable).

[E] Sky Blue Depth: blue color appearance and perception of remote origin of the sky component when looking directly at the skylight; in skylights that use light from the actual sky, a vertical open space is often used and the sky color can be seen from below, even with a diffuser—Scale: 1 (not detectable); 4 (just like the natural sky); 2 and 3 (between 1 and 4, with 2 more toward not detectable).

[F] Skylight Impression $1^{st}$/delayed: first impression is important; it does not take long for someone to tell if there is a skylight in the room; however, these perceptions can change as people adapt to lighting conditions over about 30 seconds to a few minutes—Scale: 1 (clearly artificial); 4 (just like a skylight); 2 and 3 (between 1 and 4, with 2 more toward artificial).

In another test model, each observer can rate comparatively each of a number of light fixtures, for example, one light fixture per day on three separate days (to rate three different configurations, with the brightnesses for each light engine in each configuration set to a particular value, and the correlated color temperature for each light engine set to a particular value. For each test, each observer can be in the room, by herself or himself, for about ten minutes, and after that time period, the observer can rank each of a number of characteristics of that configuration, and on the third day, each observer can review his or her rankings for all three configurations and make any desired adjustments. As a representative comparison test, for each light fixture configuration, an observer can be asked to give a rating, on a scale of 1 to 4 (1 being "clearly an artificial light, definitely not a skylight"; 2 being "looks more like an artificial light than a skylight"; 3 being "looks more like a skylight than an artificial light"; and 4 being "looks just like a real skylight"), for each of the following characteristics:

[A] How do you feel about the lighting in this room?

[B] At near the entrance, rate if the lighting resembles a skylight?

[C] Sitting on the chair and not looking up, rate whether the lighting resembles a skylight.

[D] Free to move, and look up to the light, rate if the lighting resembles a skylight.

[E] Do shadows (cast on wall or on objects) resemble those from a skylight?

[F] Does the light include light that resembles light having the sun's intensity?

[G] Does the color uniformity on walls resemble that of light from a skylight?

[H] Does the first light engine of the light fixture resemble the blue sky in its color and intensity?

For each characteristic ([A]-[H]), an average can be calculated among the observers (and/or any other statistical analysis can be performed, e.g., removing one or more high and low scores, standard deviation, etc.).

In addition, the observers can be asked to characterize the glare from the light fixtures as "acceptable" or "not acceptable".

In addition, each observer can be asked whether he or she would use the light fixture in his or her office ("Yes", "No" or "indifferent").

In addition, each observer can be asked whether he or she would use the light fixture in his or her home ("Yes", "No" or "indifferent").

In addition, each observer can be asked to state how he or she feels about the lighting in the room in comparison to other lighting in the room (e.g., whether there is any difference, whether the light is better, worse, more light a skylight, more glare, etc.).

The relationship between values recorded from such tests can be of interest. For example, a value from [D] which is much lower (e.g., 1 or more, for example 1.2 or 1.3) than the value from [C] might indicate that the blue sky from the first light engine is favorable, but directly viewing the second light engine detracts significantly from such favorable viewpoint.

Below is a table showing various combinations that each comprise a first light engine ("$1^{st}$") and a second light engine ("$2^{nd}$"), along with respective lux values for vertical illuminance ("v") and horizontal illuminance ("h"), in which brightnesses are adjusted so that the horizontal and vertical illuminances are approximately constant. Illuminance measurements were performed with Konica-Minolta T10 illuminance meter. Horizontal illuminances were measured directly below the light fixture on surface parallel to the ceiling at approximately table top height of 2.5 ft from ground. Vertical illuminances were measured on a surface perpendicular to the ceiling at height of about 5 ft from the ground. The configuration of the first and second light engines was similar to the embodiment shown in FIG. 7, mounted in an 8' high ceiling. The power supplied to the multiple LED strings in the first light engine is selected such that the first light engine emits (1) light having a correlated color temperature of 3000K (and with a vertical illuminance of 101 lux and a horizontal illuminance of 220 lux) exits, (2) light having a correlated color temperature of 4000K (and with a vertical illuminance of 98 lux and a horizontal illuminance of 210 lux) exits, (3) light having a correlated color temperature of 5000K (and with a vertical illuminance of 102 lux and a horizontal illuminance of 219 lux) exits, (4) light having a correlated color temperature of 6000K (and with a vertical illuminance of 102 lux and a horizontal illuminance of 220 lux) exits, (5) light having a correlated color temperature of 9300K (and with a vertical illuminance of 102 lux and a horizontal illuminance of 221 lux) exits, (6) light having a correlated color temperature of 17,000K (and with a vertical illuminance of 103 lux and a horizontal illuminance of 223 lux). The power supplied to the two LED strings in the second light engine is selected such that the second light engine emits (1) light having a correlated color temperature of 5000K (and with a vertical illuminance of 901 lux and a horizontal illuminance of 234 lux) exits, (2) light having a correlated color temperature of 4000K (and with a vertical illuminance of 929 lux and a horizontal illuminance of 237 lux) exits, and (3) light having a correlated color temperature of 3000K (and with a vertical illuminance of 955 lux and a horizontal illuminance of 235 lux) exits.

TABLE 2

|  | $1^{st}$ 3000 K | $1^{st}$ 4000 K | $1^{st}$ 5000 K | $1^{st}$ 6000 K | $1^{st}$ 9000 K | $1^{st}$ 17,000 K |
| --- | --- | --- | --- | --- | --- | --- |
| $2^{nd}$ 5000 K | v 1002 h 454 | v 999 h 444 | v 1003 h 453 | v 1003 h 454 | v 1003 h 455 | *v 1004 *h 457 |
| $2^{nd}$ 4000 K | v 1030 h 457 | v 1027 h 447 | v 1031 h 456 | v 1031 h 457 | *v 1031 *h 458 | *v 1032 *h 460 |
| $2^{nd}$ 3000 K | v 1056 h 455 | v 1053 h 445 | *v 1057 *h 454 | *v 1057 *h 455 | *v 1057 *h 456 | *v 1058 *h 458 |

As seen above, the favorable results, indicated in Table 2 by "*v" and "*h", tend to the lower right portion of the table, indicating that in some embodiments it is advantageous for the sky color (CCT) to be bluer (higher) than the sun color (CCT).

Representative combinations from Table 2 that provide particularly favorable results include: 17,000K first light engine and 5000K second light engine; 9000K first light engine and 3000K second light engine; 6000K first light engine and 3000K second light engine; 9000K first light engine and 4000K second light engine; 17,000K first light engine and 4000K second light engine; 5000K first light engine and 3000K second light engine; and 17,000K first light engine and 3000K second light engine.

Light fixtures in accordance with the present inventive subject matter are scalable (i.e., the size of the light fixtures, or any portion or portions thereof, can be modified by being magnified or shrunk to any degree). For example, a large (or immense) light fixture can be made by increasing the size of one or more components and/or by increasing the number of components (e.g., providing an array of direct-lit panels and an array of downlights, etc.). In view of the scalability of the present inventive subject matter, the brightness (e.g., quantity of lux and/or lumens delivered) is similarly scalable, and accordingly there are effectively no limits.

In some embodiments in accordance with the present inventive subject matter, including some embodiments that include or do not include any of the features described herein, a second light engine is movable relative to a first light engine and/or a sidewall. In some of such embodiments, the light fixture further comprises a motor that is configured to move a second light engine, and/or to change the orientation of the second light engine, relative to the first light engine and/or a sidewall (e.g., by moving and/or altering the orientation of a support that is configured to hold the second light engine), e.g., in devices in accordance with the first aspect of the present inventive subject matter to mimic changes in sunlight over the course of a day and/or seasons of the year (e.g., to alter the angle of at least some of the light that exits from the second light engine to resemble changes that occur to sunlight over the course of a day). In embodiments in which the second light engine is movable relative to the first light engine and the sidewall, such movement can be automatic and/or input manually (e.g., by a user).

In some embodiments in accordance with the present inventive subject matter, including some embodiments that include or do not include any of the features described herein, the light fixture further comprises at least a first waveguide and/or a first light guide, and a second light engine is positioned relative to the first waveguide and/or the first light guide such that light that exits from the second light engine enters the first waveguide (and/or the first light guide). In some of such embodiments, the first waveguide (and/or the first light guide) is/are movable relative to the second light engine to change the orientation and/or the position of the first waveguide (and/or the first light guide) relative to the second light engine. For example, in some embodiments, the light fixture further comprises a waveguide bracket (which is configured to hold the first waveguide) and/or a light guide bracket (which is configured to hold the first light guide) and a motor which is configured to change the orientation and/or position of the first waveguide (and/or the first light guide) relative to the second light engine.

In some embodiments in which the light fixture comprises at least a first waveguide and/or a first light guide, the first waveguide (and/or the first light guide) is configured to change the direction(s) that at least some light that exits from the second light engine travels upon changing the orientation and/or position of the first waveguide (and/or the first light guide) relative to the second light engine.

In some embodiments in which the light fixture comprises at least a first waveguide and/or a first light guide, movement (changing the orientation and/or position) of the first waveguide (and/or the first light guide) relative to the second light engine corresponds to passage of time, e.g., the direction(s) of travel (e.g., the axis of emission) of at least some light that exits from the second light engine after passing through the first waveguide (and/or the first light guide) changes over the course of the day to correlate with (or emulate) the movement of the sun over the course of the day.

In embodiments in which the light fixture comprises at least a first waveguide and/or a first light guide and the first waveguide (and/or the first light guide) is movable relative to the second light engine, such movement can be automatic and/or input manually (e.g., by a user).

Light fixtures in accordance with the present inventive subject matter can be used as skylights, and/or as wall wash lighting (e.g., light fixtures that are configured and/or oriented such that a large portion of light that exits the light fixtures illuminates one or more walls) or as accent lighting (e.g., light fixtures that are configured and/or oriented such that they throw a large amount of light on a particular area or object(s)).

Light sources in the light fixtures in accordance with the present inventive subject matter can be supplied with electricity in any suitable manner. Skilled artisans are familiar with a wide variety of apparatuses and/or components for supplying electricity to light sources, and any such apparatuses and/or components can be employed in connection with the present inventive subject matter. Light fixtures in accordance with the present inventive subject matter can be electrically connected (or selectively connected) to any suitable power source, persons of skill in the art being familiar with a variety of such power sources.

Light fixtures according to the present inventive subject matter can, as desired, include any suitable circuitry components, e.g., drive electronics for supplying and controlling current passed through any light sources in the light fixture. Persons of skill in the art are familiar with a wide variety of ways to supply and control the current passed through light sources, and any such ways can be employed in light fixtures in accordance with the present inventive subject matter. For example, such circuitry can include at least one contact, at least one leadframe, at least one current regulator, at least one power control, at least one voltage control, at least one boost, at least one capacitor and/or at least one bridge rectifier, persons of skill in the art being familiar with such components and being readily able to design appropriate circuitry to meet whatever current flow characteristics are desired.

The light fixtures according to the present inventive subject matter can further comprise any suitable electrical connector, a wide variety of which are familiar to those of skill in the art, e.g., an Edison connector (for insertion in an Edison socket), a GU24 connector, etc., or light fixtures may be directly wired to an electrical branch circuit.

Compensation circuits can be provided to help to ensure that the perceived color (including correlated color temperature) of light exiting a light engine (e.g., a first light engine or a second light engine) is accurate (e.g., within a specific tolerance). Such compensation circuits, if included, can (for example) adjust the current supplied to light sources that emit light of one color and/or separately adjust the current supplied to light sources that emit light of a different color, so as to adjust the color of mixed light, and such adjustment(s) can be (1) based on temperature sensed by one or more temperature sensors (if included), and/or (2) based on light sensed by one or more light sensors (if included) (e.g., based on one or more sensors that detect (i) the color of the light that exits from a light engine and/or a light source, and/or (ii) the brightness of the light being emitted from one or more light sources, and/or (iii) the brightness of light of one or more specific hues of color), and/or based on any other sensors (if included), factors, phenomena, etc.

A wide variety of compensation circuits are known, and any can be employed in the light fixtures according to the present inventive subject matter. For example, a compensation circuit may comprise a digital controller, an analog controller or a combination of digital and analog. For example, a compensation circuit may comprise an application specific integrated circuit (ASIC), a microprocessor, a microcontroller, a collection of discrete components or combinations thereof. In some embodiments, a compensation circuit may be programmed to control one or more light sources. In some embodiments, control of one or more light sources may be provided by the circuit design of the compensation circuit and is, therefore, fixed at the time of manufacture. In still further embodiments, aspects of the compensation circuit, such as reference voltages, resistance values or the like, may be set at the time of manufacture so as to allow adjustment of the control of the one or more light sources without the need for programming or control code.

Energy can be supplied to the at least one light source from any source or combination of sources, for example, the grid (e.g., line voltage), one or more batteries, one or more photovoltaic energy collection devices (i.e., a device that includes one or more photovoltaic cells that convert energy from the sun into electrical energy), one or more windmills, etc.

The light fixtures in accordance with the present inventive subject matter can comprise any suitable heat transfer or dissipation elements, structures, components and/or materials, and/or cooling elements, as desired or needed to comply with regulations and/or to assist in providing a long useful life for the light fixtures and the components therein (e.g., light emitting diodes). Persons of skill in the art are familiar with a wide variety of heat transfer or dissipation elements, structures, components and materials, and schemes for their deployments, and a wide variety of cooling elements, and schemes for their deployment, and any such heat transfer or dissipation elements, structures, components and/or materials, and/or cooling elements, and schemes, combinations and arrangements thereof can be employed in accordance with the present inventive subject matter.

Many alterations and modifications may be made by those having ordinary skill in the art, given the benefit of the present disclosure, without departing from the spirit and scope of the inventive subject matter. Therefore, it must be understood that the illustrated embodiments have been set forth only for the purposes of example, and that it should not be taken as limiting the inventive subject matter as defined by the following claims. The following claims are, therefore, to be read to include not only the combination of elements which are literally set forth but all equivalent elements for performing substantially the same function in substantially the same way to obtain substantially the same result. The claims are thus to be understood to include what is specifically illustrated and described above, what is conceptually equivalent, and also what incorporates the essential idea of the inventive subject matter.

Any two or more structural parts of the light fixtures described herein can be integrated. Any structural part of the light fixtures described herein can be provided in two or more parts (which may be held together in any known way, e.g., with adhesive, screws, bolts, rivets, staples, etc.). Similarly, any two or more functions can be conducted simultaneously, and/or any function can be conducted in a series of steps.

The invention claimed is:

1. A light fixture, comprising:
a control element;
a first light engine; and
a second light engine,
the control element configured to vary a ratio of brightness of light output from the first light engine to brightness of light output from the second light engine,
the first light engine emits light that has a x, y color coordinates which define a point on a 1931 CIE Chromacity Diagram which is within an area with vertices having x, y coordinates of (0.37, 0.34), (0.35, 0.38), (0.15, 0.20), and (0.20, 0.14); and
the second light engine emits light that has x, y color coordinates which define a point on a 1931 CIE Chromacity Diagram which is within an area with vertices having x, y coordinates of (0.29, 0.32), (0.32, 0.29), (0.41, 0.36), (0.48, 0.39), (0.48, 0.43), (0.40, 0.41), and (0.35, 0.38).

2. A control element as recited in claim 1, wherein the control element:
causes the ratio of brightness of light output from the first light engine to brightness of light output from the second light engine to be at least a first value during a first part of the day,
causes the ratio of brightness of light output from the first light engine to brightness of light output from the second light engine to be not greater than a second value during a second part of the day, and
the first value is greater than the second value.

3. A control element as recited in claim 1, wherein the control element also causes a color point of light that exits from at least a first region of the first light engine to vary based on time of day.

4. A control element as recited in claim 1, the control element configured to vary brightness of light output from a first portion of a sidewall of a light fixture and/or brightness of light output from a second portion of the sidewall of the light fixture, wherein the sidewall defines a space, and the sidewall extends around the space.

5. A control element as recited in claim 4, wherein the control element varies brightness of light output from the first portion of the sidewall and/or the brightness of light output from the second portion of the sidewall to mimic movement of the sun.

6. A control element as recited in claim 4, wherein the control element is configured to adjust brightness of light exiting from the first portion of the sidewall and brightness of light exiting from the second portion of the sidewall based on the time of day.

7. A control element as recited in claim 4, wherein the control element is configured to adjust brightness of light exiting from the first portion of the sidewall and brightness of light exiting from the second portion of the sidewall according to a repeating 24-hour cycle.

8. A control element as recited in claim 4, wherein the control element is configured to adjust brightness and color point of light exiting from the first portion of the sidewall, and brightness and color point of light exiting from the second portion of the sidewall, based on time of day.

9. A control element as recited in claim 4, wherein the control element is configured to adjust brightness and color point of light exiting from the first portion of the sidewall, and brightness and color point of light exiting from the second portion of the sidewall, according to a repeating 24-hour cycle.

10. A control element as recited in claim 4, wherein the control element adjusts brightness and color point of light output from the first portion of the sidewall, and brightness and color point of light output from the second portion of the sidewall, to mimic movement of the sun.

11. A light fixture comprising:
a control element configured to vary a color point of light exiting from a first portion of a sidewall of a light fixture and a color point of light exiting from a second portion of the sidewall of the light fixture, wherein the sidewall defines a space, and the sidewall extends around the space;
a first light engine that emits light that has x, y color coordinates which define a point on a 1931 CIE Chromaticity Diagram which is within an area with vertices having x, y coordinates of (0.37, 0.34), (0.35, 0.38), (0.15, 0.20), and (0.20, 0.14); and
said sidewall, wherein from each of the first and second portions of the sidewall, light that has x, y color coordinates which define a point on a 1931 CIE Chromaticity Diagram which is within an area with vertices having x, y coordinates of (0.29, 0.32), (0.32, 0.29), (0.41, 0.36), (0.48, 0.39), (0.48, 0.43), (0.40, 0.41), and (0.35, 0.38) exits.

12. A control element as recited in claim 11, wherein the control element is configured to vary a color point of light exiting from a first portion of a sidewall and a color point of light exiting from a second portion of the sidewall based on the time of day.

13. A control element as recited in claim 11, wherein the control element adjusts a color point of light exiting from the first portion of the sidewall and a color point of light exiting from the second portion of the sidewall to mimic movement of the sun.

14. A control element as recited in claim 11, wherein the control element is configured to vary a color point of light exiting from the first portion of the sidewall and a color point of light exiting from the second portion of the sidewall according to a repeating 24-hour cycle.

15. A light fixture comprising:
a control element configured to vary a color point of light exiting from a first portion of a sidewall and a color point of light exiting from a second portion of the sidewall based on the time of day, wherein the sidewall defines a space, and the sidewall extends around the space;
a first light engine that emits light that has x, y color coordinates which define a point on a 1931 CIE Chromaticity Diagram which is within an area with vertices having x, y coordinates of (0.37, 0.34), (0.35, 0.38), (0.15, 0.20), and (0.20, 0.14); and
said sidewall, wherein from each of the first and second portions of the sidewall, light that has x, y color coordinates which define a point on a 1931 CIE Chromaticity Diagram which is within an area with vertices having x, y coordinates of (0.29, 0.32), (0.32, 0.29), (0.41, 0.36), (0.48, 0.39), (0.48, 0.43), (0.40, 0.41), and (0.35, 0.38) exits.

16. A light fixture, comprising:
a control element;
a first light engine; and
a second light engine,
the control element configured to vary a circadian stimulus value of light exiting from a light fixture, said circadian stimulus value equal to a percentage of melatonin suppression when exposed to the light exiting from the light fixture,
the first light engine emits light that has x, v color coordinates which define a point on a 1931 CIE Chromaticity Diagram which is within an area with vertices having x, y coordinates of (0.37, 0.34), (0.35, 0.38), (0.15, 0.20), and (0.20, 0.14); and
the second light engine emits light that has x, v color coordinates which define a point on a 1931 CIE Chromaticity Diagram which is within an area with vertices having x, y coordinates of (0.29, 0.32), (0.32, 0.29), (0.41, 0.36), (0.48, 0.39), (0.48, 0.43), (0.40, 0.41), and (0.35, 0.38).

17. A control element as recited in claim 16, wherein the control element is configured to vary the circadian stimulus value of light exiting from the light fixture by varying a ratio of brightness of light exiting from a first light engine of the light fixture vs. brightness of light exiting from a second light engine of the light fixture, based on time of day.

18. A control element as recited in claim 16, wherein the control element is configured to vary the circadian stimulus value of light exiting from the light fixture by varying a ratio of brightness of light exiting from a first light engine of the light fixture vs. brightness of light exiting from a second light engine of the light fixture, according to a repeating 24-hour cycle.

19. A control element as recited in claim 16, wherein the control element comprises multiple circadian stimulus value settings, incremental circadian stimulus value settings, or a substantially continuous range of circadian stimulus value settings.

* * * * *